(12) United States Patent
Satti, III et al.

(10) Patent No.: US 12,016,558 B2
(45) Date of Patent: Jun. 25, 2024

(54) SURGICAL STAPLER WITH REMOVABLE POWER PACK

(71) Applicant: RevMedica, Inc., Durham, CT (US)

(72) Inventors: C. Robert Satti, III, Westbrook, CT (US); Jeffrey M. Ott, New Haven, CT (US); Thomas G. Wenchell, Jr., Durham, CT (US)

(73) Assignee: REVMEDICA, INC, Middletown, CT (US)

( * ) Notice: Subject to any disclaimer, the term of this patent is extended or adjusted under 35 U.S.C. 154(b) by 0 days.

(21) Appl. No.: 18/085,646

(22) Filed: Dec. 21, 2022

(65) Prior Publication Data

US 2023/0143166 A1 May 11, 2023

Related U.S. Application Data

(63) Continuation of application No. 17/206,861, filed on Mar. 19, 2021, now Pat. No. 11,540,830, which is a
(Continued)

(51) Int. Cl.
*A61B 17/072* (2006.01)
*A61B 17/00* (2006.01)
(Continued)

(52) U.S. Cl.
CPC ........ *A61B 17/07207* (2013.01); *A61B 17/00* (2013.01); *A61B 17/0682* (2013.01);
(Continued)

(58) Field of Classification Search
CPC .............. A61B 17/07207; A61B 17/00; A61B 17/0682; A61B 17/072; A61B 17/083;
(Continued)

(56) References Cited

U.S. PATENT DOCUMENTS

| 2,636,136 A | 4/1953 | Henry |
| 2,942,603 A * | 6/1960 | Geyer .................... A61B 17/43 42/106 |

(Continued)

FOREIGN PATENT DOCUMENTS

| AU | 2013/24552511/2013 | 11/2013 |
| CN | 106456172 | 9/2019 |

(Continued)

OTHER PUBLICATIONS

European Search Report (dated Mar. 3, 2022) from European Application No. EP 20766786.
(Continued)

*Primary Examiner* — Veronica Martin
(74) *Attorney, Agent, or Firm* — Neil D. Gershon

(57) ABSTRACT

A surgical fastener applier including a housing containing a compartment, an elongated member extending distally from the housing, first and second jaws and a firing mechanism positioned within the housing. The firing mechanism is movable between a first position and a second position to effect firing of fasteners into the tissue clamped between the first and second jaws. A cover on the housing is openable to access the compartment. A power pack is removably loadable into the compartment, the power pack having a motor and an engagement member removably engageable with the firing mechanism within the compartment when the power pack is loaded into the compartment to effect movement of the firing mechanism from the first position to the second firing position.

19 Claims, 32 Drawing Sheets

Related U.S. Application Data continuation of application No. 15/965,737, filed on Apr. 27, 2018, now Pat. No. 10,966,720.

(60) Provisional application No. 62/616,045, filed on Jan. 11, 2018, provisional application No. 62/553,297, filed on Sep. 1, 2017.

(51) Int. Cl.

| | | |
|---|---|---|
| *A61B 17/068* | (2006.01) | |
| *A61B 17/08* | (2006.01) | |
| *A61B 17/10* | (2006.01) | |
| *A61B 17/115* | (2006.01) | |
| *A61B 17/128* | (2006.01) | |
| *A61B 17/29* | (2006.01) | |
| *A61B 17/32* | (2006.01) | |
| *A61B 17/3201* | (2006.01) | |
| *A61B 34/30* | (2016.01) | |
| *A61B 50/30* | (2016.01) | |
| *A61B 90/00* | (2016.01) | |

(52) U.S. Cl.
CPC .......... *A61B 17/072* (2013.01); *A61B 17/083* (2013.01); *A61B 17/10* (2013.01); *A61B 17/1155* (2013.01); *A61B 17/1285* (2013.01); *A61B 17/29* (2013.01); *A61B 17/320016* (2013.01); *A61B 17/3201* (2013.01); *A61B 34/30* (2016.02); *A61B 50/30* (2016.02); *A61B 2017/00017* (2013.01); *A61B 2017/00115* (2013.01); *A61B 17/00234* (2013.01); *A61B 2017/00398* (2013.01); *A61B 2017/0046* (2013.01); *A61B 2017/00477* (2013.01); *A61B 2017/00734* (2013.01); *A61B 2017/07257* (2013.01); *A61B 2017/07271* (2013.01); *A61B 2017/2905* (2013.01); *A61B 2017/2927* (2013.01); *A61B 2017/2929* (2013.01); *A61B 2017/2948* (2013.01); *A61B 2050/3014* (2016.02); *A61B 2090/0813* (2016.02)

(58) Field of Classification Search
CPC . A61B 17/10; A61B 17/1155; A61B 17/1285; A61B 17/29; A61B 17/320016; A61B 17/3201; A61B 17/00234; A61B 34/30; A61B 2017/00734; A61B 2017/00017; A61B 2017/00115; A61B 2017/00398; A61B 2017/0046; A61B 2017/00477; A61B 2017/07257; A61B 2017/07271; A61B 2017/2905; A61B 2017/2927; A61B 2017/2929; A61B 50/30; A61B 2050/3014

See application file for complete search history.

(56) References Cited

U.S. PATENT DOCUMENTS

| | | |
|---|---|---|
| 3,442,240 A | 5/1969 | Loughman et al. |
| 3,494,799 A | 2/1970 | Pedone, Jr. |
| 3,734,207 A | 5/1973 | Fishbein |
| 3,895,636 A | 7/1975 | Schmidt |
| 4,114,484 A | 9/1978 | Feamster, III |
| 4,250,613 A | 2/1981 | Sauerwein |
| 4,705,038 A | 11/1987 | Sjostrom et al. |
| 4,728,876 A | 3/1988 | Mongeon et al. |
| 4,770,401 A | 9/1988 | Donaldson |
| 4,867,158 A | 9/1989 | Sugg |
| 4,962,681 A | 10/1990 | Yang |
| 5,207,697 A | 5/1993 | Carusillo et al. |
| 5,261,877 A | 11/1993 | Fine |
| 5,307,976 A | 5/1994 | Olsen et al. |
| 5,332,142 A | 7/1994 | Robinson et al. |
| 5,387,217 A | 2/1995 | Sefcik |
| 5,395,367 A | 3/1995 | Wilk |
| 5,422,136 A | 6/1995 | Fuisz |
| 5,431,323 A | 7/1995 | Smith et al. |
| 5,467,911 A | 11/1995 | Tsuruta et al. |
| 5,478,351 A | 12/1995 | Meade |
| 5,518,163 A | 5/1996 | Hooven |
| 5,551,622 A | 9/1996 | Yoon |
| 5,553,675 A | 9/1996 | Pitzen et al. |
| 5,626,595 A | 5/1997 | Sklar |
| 5,651,491 A | 7/1997 | Heaton et al. |
| 5,667,517 A | 9/1997 | Hooven |
| 5,680,981 A | 10/1997 | Milii et al. |
| 5,725,536 A | 3/1998 | Oberlin et al. |
| 5,814,058 A | 9/1998 | Carlson et al. |
| 5,954,259 A | 9/1999 | Viola et al. |
| 6,054,777 A | 4/2000 | Soh |
| 6,092,722 A | 7/2000 | Heinrichs |
| 6,331,181 B1 | 12/2001 | Tierney |
| 6,331,761 B1 | 12/2001 | Kumar et al. |
| 6,443,973 B1 | 9/2002 | Whitman |
| 6,512,348 B1 | 1/2003 | Wellisz et al. |
| 6,517,565 B1 | 2/2003 | Whitman et al. |
| 6,530,931 B1 | 3/2003 | Rosenberg |
| 6,533,157 B1 | 3/2003 | Whitman |
| 6,695,359 B2 | 2/2004 | Morel |
| 6,716,233 B1 | 4/2004 | Whitman |
| 6,843,303 B2 | 1/2005 | Siak et al. |
| 6,845,975 B2 | 1/2005 | Tunkers |
| 6,846,307 B2 | 1/2005 | Whitman et al. |
| 6,981,141 B1 | 12/2005 | Mahne et al. |
| 6,988,649 B2 | 1/2006 | Shelton, IV et al. |
| 7,114,642 B2 | 10/2006 | Whitman |
| 7,160,311 B2 | 1/2007 | Blatter |
| 7,224,642 B1 | 5/2007 | Tran |
| 7,380,696 B2 | 6/2008 | Shelton, IV et al. |
| 7,416,101 B2 | 8/2008 | Shelton, IV et al. |
| 7,422,136 B1 | 9/2008 | Marczyk |
| 7,422,139 B2 | 9/2008 | Shelton, IV et al. |
| 7,461,767 B2 | 12/2008 | Viola et al. |
| 7,464,847 B2 | 12/2008 | Viola et al. |
| 7,537,602 B2 | 5/2009 | Whitman |
| 7,568,603 B2 | 8/2009 | Shelton, IV et al. |
| 7,699,855 B2 | 4/2010 | Anderson |
| 7,717,312 B2 | 5/2010 | Beetel |
| 7,735,813 B2 | 6/2010 | Geier |
| 7,766,210 B2 | 8/2010 | Shelton, IV et al. |
| 7,793,812 B2 | 9/2010 | Moore et al. |
| 7,815,092 B2 | 10/2010 | Whitman et al. |
| 7,845,538 B2 | 12/2010 | Whitman |
| 7,922,063 B2 | 4/2011 | Zemlok et al. |
| 7,947,034 B2 | 5/2011 | Whitman |
| 7,950,560 B2 | 5/2011 | Zemlok et al. |
| 7,959,050 B2 | 6/2011 | Smith et al. |
| 7,963,433 B2 | 6/2011 | Whitman et al. |
| 8,006,885 B2 | 8/2011 | Marczyk |
| 8,011,551 B2 | 9/2011 | Marczyk et al. |
| 8,012,170 B2 | 9/2011 | Whitman et al. |
| 8,016,855 B2 | 9/2011 | Whitman et al. |
| 8,016,858 B2 | 9/2011 | Whitman |
| 8,021,373 B2 | 9/2011 | Whitman et al. |
| 8,056,786 B2 | 11/2011 | Whitman et al. |
| 8,056,791 B2 | 11/2011 | Whitman |
| 8,062,311 B2 | 11/2011 | Litscher et al. |
| 8,074,858 B2 | 12/2011 | Marczyk |
| 8,142,447 B2 | 3/2012 | Cooper |
| 8,142,473 B2 | 3/2012 | Cunningham |
| 8,157,150 B2 | 4/2012 | Viola et al. |
| 8,181,839 B2 | 5/2012 | Beetel |
| 8,186,555 B2 | 5/2012 | Shelton, IV et al. |
| 8,205,779 B2 | 6/2012 | Ma et al. |
| 8,240,536 B2 | 8/2012 | Marczyk |
| 8,240,537 B2 | 8/2012 | Marczyk |
| 8,241,322 B2 | 8/2012 | Whitman et al. |
| 8,245,899 B2 | 8/2012 | Swensgard et al. |
| 8,251,994 B2 | 8/2012 | McKenna et al. |
| 8,257,387 B2 | 9/2012 | Cunningham |
| 8,276,801 B2 | 10/2012 | Zemlok et al. |

(56) References Cited

U.S. PATENT DOCUMENTS

| | | |
|---|---|---|
| 8,277,473 B2 | 10/2012 | Sunaoshi |
| 8,342,377 B2 | 1/2013 | Milliman et al. |
| 8,342,378 B2 | 1/2013 | Marczyk et al. |
| 8,353,440 B2 | 1/2013 | Whitman et al. |
| 8,357,174 B2 | 1/2013 | Roth |
| 8,382,782 B2 | 2/2013 | Robertson |
| 8,409,175 B2 | 4/2013 | Lee et al. |
| 8,409,222 B2 | 4/2013 | Whitfield et al. |
| 8,444,036 B2 | 5/2013 | Shelton, IV |
| 8,453,907 B2 | 6/2013 | Laurent et al. |
| 8,453,914 B2 | 6/2013 | Laurent et al. |
| 8,459,521 B2 | 6/2013 | Zemlok et al. |
| 8,459,525 B2 | 6/2013 | Yates et al. |
| 8,479,969 B2 | 7/2013 | Shelton, IV |
| 8,499,992 B2 | 8/2013 | Whitman et al. |
| 8,517,241 B2 | 8/2013 | Nicholas et al. |
| 8,551,025 B2 | 10/2013 | Soltz |
| 8,556,151 B2 | 10/2013 | Viola |
| 8,573,462 B2 | 11/2013 | Smith et al. |
| 8,573,463 B2 | 11/2013 | Scirica et al. |
| 8,602,287 B2 | 12/2013 | Yates et al. |
| 8,602,288 B2 | 12/2013 | Shelton, IV et al. |
| 8,608,045 B2 | 12/2013 | Smith et al. |
| 8,622,274 B2 | 1/2014 | Yates et al. |
| 8,631,988 B2 | 1/2014 | Viola |
| 8,631,998 B1 | 1/2014 | Viola |
| 8,636,736 B2 | 1/2014 | Yates et al. |
| 8,636,766 B2 | 1/2014 | Milliman et al. |
| 8,657,174 B2 | 2/2014 | Yates et al. |
| 8,657,177 B2 | 2/2014 | Scirica et al. |
| 8,662,371 B2 | 3/2014 | Viola |
| 8,672,206 B2 | 3/2014 | Aranyi et al. |
| 8,690,913 B2 | 4/2014 | Whitman |
| 8,708,213 B2 | 4/2014 | Shelton, IV et al. |
| 8,733,614 B2 | 5/2014 | Ross et al. |
| 8,752,748 B2 | 6/2014 | Whitman et al. |
| 8,764,749 B2 | 7/2014 | Mckenna et al. |
| 8,777,945 B2 | 7/2014 | Floume et al. |
| 8,795,313 B2 | 8/2014 | Liang et al. |
| 8,800,837 B2 | 8/2014 | Zemlok |
| 8,820,603 B2 | 9/2014 | Shelton, IV et al. |
| 8,821,514 B2 | 9/2014 | Aranyi |
| 8,827,134 B2 | 9/2014 | Viola et al. |
| 8,834,466 B2 | 9/2014 | Cummings et al. |
| 8,851,355 B2 | 10/2014 | Aranyi et al. |
| 8,864,753 B2 | 10/2014 | Nau, Jr. et al. |
| 8,875,973 B2 | 11/2014 | Whitman |
| 8,899,462 B2 | 12/2014 | Kostrzewski et al. |
| 8,911,471 B2 | 12/2014 | Spivey et al. |
| 8,955,732 B2 | 2/2015 | Zemlok et al. |
| 8,960,520 B2 | 2/2015 | McCuen |
| 8,967,443 B2 | 3/2015 | McCuen |
| 8,968,276 B2 | 3/2015 | Zemlok et al. |
| 8,968,285 B2 | 3/2015 | Twomey et al. |
| 8,991,677 B2 | 3/2015 | Moore et al. |
| 8,998,058 B2 | 4/2015 | Moore et al. |
| 9,017,355 B2 | 4/2015 | Smith et al. |
| 9,028,478 B2 | 5/2015 | Mueller |
| 9,072,523 B2 | 7/2015 | Houser et al. |
| 9,084,601 B2 | 7/2015 | Moore et al. |
| 9,095,339 B2 | 8/2015 | Moore et al. |
| 9,101,358 B2 | 8/2015 | Kerr et al. |
| 9,113,874 B2 | 8/2015 | Shelton, IV et al. |
| 9,113,880 B2 | 8/2015 | Zemlok et al. |
| 9,113,901 B2 | 8/2015 | Allen, IV et al. |
| 9,186,143 B2 | 11/2015 | Timm et al. |
| 9,192,381 B2 | 11/2015 | Marczyk |
| 9,241,716 B2 | 1/2016 | Whitman |
| 9,265,585 B2 | 2/2016 | Wingardner et al. |
| 9,301,772 B2 | 4/2016 | Kimball et al. |
| 9,320,520 B2 | 4/2016 | Shelton, IV et al. |
| 9,326,769 B2 | 5/2016 | Shelton, IV et al. |
| 9,326,770 B2 | 5/2016 | Shelton, IV et al. |
| 9,326,812 B2 * | 5/2016 | Waaler ............... A61B 18/1442 |
| 9,351,727 B2 | 5/2016 | Leimbach et al. |
| 9,364,220 B2 | 6/2016 | Williams |
| 9,364,224 B2 | 6/2016 | Nicholas et al. |
| 9,370,360 B2 | 6/2016 | Marczyk |
| 9,370,364 B2 | 6/2016 | Smith et al. |
| 9,393,015 B2 | 7/2016 | Laurent et al. |
| 9,398,911 B2 | 7/2016 | Auld |
| 9,402,604 B2 | 8/2016 | Williams et al. |
| 9,414,818 B2 | 8/2016 | Azarbarzin et al. |
| 9,421,003 B2 | 8/2016 | Williams et al. |
| 9,421,014 B2 | 8/2016 | Ingmanson et al. |
| 9,433,415 B2 | 9/2016 | Marczyk et al. |
| 9,451,958 B2 | 9/2016 | Shelton, IV et al. |
| 9,468,454 B2 | 10/2016 | Johnson et al. |
| 9,474,513 B2 | 10/2016 | Ishida |
| 9,474,528 B2 | 10/2016 | Marczyk |
| 9,484,657 B2 | 11/2016 | Martin et al. |
| 9,486,214 B2 | 11/2016 | Shelton, IV |
| 9,492,167 B2 | 11/2016 | Shelton, IV et al. |
| 9,504,520 B2 | 11/2016 | Worell et al. |
| 9,517,068 B2 | 12/2016 | Shelton, IV et al. |
| 9,539,006 B2 | 1/2017 | Collings et al. |
| 9,549,750 B2 | 1/2017 | Shelton, IV et al. |
| 9,554,803 B2 | 1/2017 | Smith et al. |
| 9,561,031 B2 | 2/2017 | Heinrich et al. |
| 9,585,672 B2 | 3/2017 | Bastia |
| 9,592,056 B2 | 3/2017 | Mozdzierz et al. |
| 9,597,081 B2 | 3/2017 | Swayze et al. |
| 9,615,828 B2 | 4/2017 | Scirica |
| 9,622,744 B2 | 4/2017 | Smith et al. |
| 9,636,091 B2 | 5/2017 | Beardsley et al. |
| 9,649,110 B2 | 5/2017 | Parilhar et al. |
| 9,655,614 B2 | 5/2017 | Swensgard et al. |
| 9,662,110 B2 | 5/2017 | Huang et al. |
| 9,675,348 B2 | 6/2017 | Smith et al. |
| 9,685,281 B2 | 6/2017 | Wang et al. |
| 9,687,230 B2 | 6/2017 | Leimbach et al. |
| 9,687,234 B2 | 6/2017 | Smith et al. |
| 9,687,236 B2 | 6/2017 | Leimbach et al. |
| 9,687,253 B2 | 6/2017 | Detry et al. |
| 9,700,310 B2 | 7/2017 | Moragan et al. |
| 9,700,318 B2 | 7/2017 | Scirica et al. |
| 9,743,928 B2 | 8/2017 | Shelton, IV et al. |
| 9,750,499 B2 | 9/2017 | Leimbach et al. |
| 9,775,610 B2 | 10/2017 | Nicholas et al. |
| 9,782,172 B2 | 10/2017 | Whitman |
| 9,782,187 B2 | 10/2017 | Zergiebal et al. |
| 9,788,836 B2 | 10/2017 | Overmyer et al. |
| 9,797,486 B2 | 10/2017 | Zergiebal et al. |
| 9,801,626 B2 | 10/2017 | Parilhar et al. |
| 9,826,976 B2 | 11/2017 | Parihar et al. |
| 9,833,235 B2 | 12/2017 | Penna et al. |
| 9,844,368 B2 | 12/2017 | Boudreanx et al. |
| 9,844,375 B2 | 12/2017 | Overmyer et al. |
| 9,867,612 B2 | 1/2018 | Parilhar et al. |
| 9,877,720 B2 | 1/2018 | Worrell et al. |
| 9,901,344 B2 | 2/2018 | Moore et al. |
| 9,901,346 B2 | 2/2018 | Moore et al. |
| 9,907,552 B2 | 3/2018 | Measamer et al. |
| 9,924,942 B2 | 3/2018 | Swayze et al. |
| 9,924,964 B2 | 3/2018 | Karasti |
| 9,936,949 B2 | 4/2018 | Measamer et al. |
| 9,936,951 B2 | 4/2018 | Hufnagel et al. |
| 9,937,626 B2 | 4/2018 | Rockrohr |
| 9,949,737 B2 | 4/2018 | Zergiebel et al. |
| 9,955,965 B2 | 5/2018 | Chen et al. |
| 9,955,966 B2 | 5/2018 | Zergiebel |
| 9,962,157 B2 | 5/2018 | Sapre |
| 9,962,159 B2 | 5/2018 | Heunrich et al. |
| 9,974,539 B2 | 5/2018 | Yates et al. |
| 9,980,729 B2 | 5/2018 | Moore et al. |
| 9,991,069 B2 | 6/2018 | Nicholas et al. |
| 10,004,498 B2 | 6/2018 | Morgan et al. |
| 10,041,822 B2 | 8/2018 | Zemlok |
| 10,045,778 B2 | 8/2018 | Yates |
| 10,052,100 B2 | 8/2018 | Morgan et al. |
| 10,064,621 B2 | 9/2018 | Kerr et al. |
| 10,070,861 B2 | 9/2018 | Spivey et al. |
| 10,076,379 B2 | 9/2018 | Boudreaux |
| 10,085,752 B2 | 10/2018 | Williams et al. |

(56) References Cited

U.S. PATENT DOCUMENTS

| | | |
|---|---|---|
| 10,111,662 B2 | 10/2018 | Zemlok et al. |
| 10,111,665 B2 | 10/2018 | Aranyi et al. |
| 10,117,654 B2 | 11/2018 | Ingmanson et al. |
| 10,136,887 B2 | 11/2018 | Shelton, IV et al. |
| 10,143,472 B2 | 12/2018 | Williams |
| 10,149,683 B2 | 12/2018 | Smith et al. |
| 10,172,612 B2 | 1/2019 | Frushour |
| 10,178,992 B2 | 1/2019 | Wise et al. |
| 10,180,463 B2 | 1/2019 | Beckman et al. |
| 10,182,816 B2 | 1/2019 | Shelton, IV |
| 10,190,888 B2 | 1/2019 | Hryb et al. |
| 10,220,522 B2 | 3/2019 | Rockrohr |
| 10,226,249 B2 | 3/2019 | Jaworek et al. |
| 10,226,250 B2 | 3/2019 | Beckman et al. |
| 10,245,033 B2 | 4/2019 | Overmyer et al. |
| 10,426,468 B2 | 10/2019 | Contini |
| 10,443,918 B2 | 10/2019 | Li et al. |
| 10,194,907 B2 | 12/2019 | Marczyk et al. |
| 10,507,034 B2 | 12/2019 | Timm |
| 10,524,787 B2 | 1/2020 | Shelton, IV et al. |
| 10,568,651 B2 | 2/2020 | Kostrzewski |
| 10,617,415 B2 | 4/2020 | Wenchell et al. |
| 10,625,384 B2 | 4/2020 | Park |
| 10,695,060 B2 | 6/2020 | Satti, III |
| 10,709,512 B2 | 7/2020 | Bajo et al. |
| 10,722,312 B2 | 7/2020 | Marshall et al. |
| 10,736,706 B2 | 8/2020 | Scheib |
| 10,743,849 B2 | 8/2020 | Shelton, IV et al. |
| 10,765,486 B2 | 9/2020 | Bajo et al. |
| 10,779,822 B2 | 9/2020 | Yates |
| 10,779,901 B2 | 9/2020 | Zietlow et al. |
| 10,780,539 B2 | 9/2020 | Shelton, IV |
| 10,806,449 B2 | 10/2020 | Shelton, IV et al. |
| 10,821,046 B2 | 11/2020 | Hares et al. |
| 10,863,983 B2 | 12/2020 | Kobayashi |
| 10,874,391 B2 | 12/2020 | Shelton, IV |
| 10,881,404 B2 | 1/2021 | Viola et al. |
| 10,905,422 B2 | 2/2021 | Bakos et al. |
| 10,959,806 B2 * | 3/2021 | Hibner ............... A61B 90/98 |
| 11,020,112 B2 | 6/2021 | Shelton, IV |
| 11,078,945 B2 | 8/2021 | Grout |
| 11,197,672 B2 | 12/2021 | Dunki-Jacobs |
| 11,278,281 B2 | 3/2022 | Shelton, IV et al. |
| 11,278,283 B2 | 3/2022 | Park |
| 11,350,893 B2 | 6/2022 | Averbuch et al. |
| 11,510,669 B2 | 11/2022 | Nicholas |
| 11,523,509 B2 | 12/2022 | Seow |
| 2002/0096341 A1 | 7/2002 | Hagan |
| 2002/0143346 A1 | 10/2002 | McGuckin, Jr. et al. |
| 2002/0190455 A1 | 12/2002 | Sawdon |
| 2003/0105475 A1 * | 6/2003 | Sancoff ............ A61B 17/064 606/139 |
| 2003/0105488 A1 | 6/2003 | Chu |
| 2003/0149424 A1 | 8/2003 | Barlev |
| 2004/0087970 A1 | 5/2004 | Chu |
| 2004/0144395 A1 | 7/2004 | Evans |
| 2004/0231870 A1 | 11/2004 | McCormick |
| 2005/0014994 A1 | 1/2005 | Fowler |
| 2005/0021018 A1 | 1/2005 | Anderson et al. |
| 2005/0033352 A1 | 2/2005 | Zepf |
| 2005/0107809 A1 | 5/2005 | Litscher et al. |
| 2005/0187576 A1 | 8/2005 | Whitman |
| 2006/0017210 A1 | 1/2006 | Sato |
| 2006/0037766 A1 | 2/2006 | Gass |
| 2006/0235436 A1 | 10/2006 | Anderson |
| 2007/0023477 A1 | 2/2007 | Whitman |
| 2007/0112364 A1 | 5/2007 | Gerbi |
| 2007/0118163 A1 | 5/2007 | Boudreaux et al. |
| 2007/0139915 A1 | 6/2007 | Walters |
| 2008/0039884 A1 | 2/2008 | Nohilly |
| 2008/0077149 A1 | 3/2008 | Hoegerle |
| 2008/0203135 A1 | 8/2008 | Viola et al. |
| 2008/0223904 A1 | 9/2008 | Marczyk |
| 2008/0255597 A1 | 10/2008 | Pravong et al. |
| 2008/0281353 A1 | 11/2008 | Aranyi et al. |
| 2008/0296346 A1 | 12/2008 | Shelton, IV |
| 2009/0001122 A1 | 1/2009 | Prommersberger |
| 2009/0012520 A1 | 1/2009 | Hixson |
| 2009/0095790 A1 | 4/2009 | Whitman |
| 2009/0108048 A1 | 4/2009 | Zemlok |
| 2009/0110533 A1 | 4/2009 | Jinno |
| 2009/0171243 A1 | 7/2009 | Hibner |
| 2009/0182193 A1 | 7/2009 | Whitman |
| 2009/0209979 A1 | 8/2009 | Yates et al. |
| 2009/0250501 A1 | 10/2009 | Sonnenschein |
| 2009/0312603 A1 | 12/2009 | Lam et al. |
| 2010/0069833 A1 | 3/2010 | Wenderow et al. |
| 2010/0137681 A1 | 6/2010 | Ewers et al. |
| 2010/0152758 A1 | 6/2010 | Mark et al. |
| 2010/0170931 A1 | 7/2010 | Viola |
| 2010/0198220 A1 | 8/2010 | Boudreaux |
| 2010/0213240 A1 | 8/2010 | Kostrzewski |
| 2010/0258327 A1 | 10/2010 | Esenwein |
| 2010/0276471 A1 | 11/2010 | Whitman |
| 2010/0320252 A1 | 12/2010 | Viola |
| 2011/0011915 A1 | 1/2011 | Shelton, IV |
| 2011/0012446 A1 | 1/2011 | Maute |
| 2011/0017801 A1 | 1/2011 | Zemlok |
| 2011/0022032 A1 | 1/2011 | Zemlok et al. |
| 2011/0082471 A1 | 4/2011 | Holcomb et al. |
| 2011/0112434 A1 | 5/2011 | Ghabrial |
| 2011/0125138 A1 | 5/2011 | Malinouskas |
| 2011/0125176 A1 | 5/2011 | Yates et al. |
| 2011/0155785 A1 | 6/2011 | Laurent |
| 2011/0166585 A1 | 7/2011 | Roth |
| 2011/0220381 A1 | 9/2011 | Friese |
| 2011/0264129 A1 | 10/2011 | Holdgate |
| 2011/0282381 A1 | 11/2011 | Cronin et al. |
| 2011/0290855 A1 | 12/2011 | Moore |
| 2011/0295242 A1 | 12/2011 | Spivey et al. |
| 2012/0061446 A1 | 3/2012 | Knodel |
| 2012/0074198 A1 | 3/2012 | Huitema |
| 2012/0080489 A1 | 4/2012 | Shelton, IV |
| 2012/0110810 A1 | 5/2012 | Houser et al. |
| 2012/0116263 A1 | 5/2012 | Houser |
| 2012/0116391 A1 | 5/2012 | Houser |
| 2012/0116394 A1 * | 5/2012 | Timm ............... H01M 10/46 606/41 |
| 2012/0172924 A1 | 7/2012 | Allen, IV |
| 2012/0199632 A1 | 8/2012 | Spivey |
| 2012/0223121 A1 | 9/2012 | Viola |
| 2012/0286021 A1 | 11/2012 | Kostrzewski |
| 2012/0292367 A1 | 11/2012 | Morgan |
| 2012/0298719 A1 | 11/2012 | Shelton, IV |
| 2013/0032627 A1 | 2/2013 | Viola |
| 2013/0098968 A1 | 4/2013 | Aranyi |
| 2013/0153633 A1 | 6/2013 | Casasanta, Jr. |
| 2013/0168435 A1 | 7/2013 | Haung |
| 2013/0181029 A1 | 7/2013 | Milliman |
| 2013/0181033 A1 | 7/2013 | Shelton, IV et al. |
| 2013/0184704 A1 | 7/2013 | Beardsley |
| 2013/0193188 A1 | 8/2013 | Shelton, IV |
| 2013/0193189 A1 | 8/2013 | Swensgard |
| 2013/0206814 A1 | 8/2013 | Morgan |
| 2013/0214030 A1 | 8/2013 | Aronhalt |
| 2013/0240604 A1 | 9/2013 | Knobel |
| 2013/0274657 A1 | 10/2013 | Zirps et al. |
| 2013/0296886 A1 | 11/2013 | Green |
| 2013/0331847 A1 | 12/2013 | Smith |
| 2014/0001235 A1 | 1/2014 | Shelton, IV |
| 2014/0005718 A1 | 1/2014 | Shelton, IV et al. |
| 2014/0012289 A1 | 1/2014 | Snow et al. |
| 2014/0058363 A1 | 2/2014 | Berkelaar |
| 2014/0114334 A1 | 4/2014 | Olson |
| 2014/0166023 A1 | 6/2014 | Kishi |
| 2014/0175150 A1 | 6/2014 | Shelton, IV |
| 2014/0207125 A1 | 7/2014 | Applegate et al. |
| 2014/0213848 A1 | 7/2014 | Moskowitz et al. |
| 2014/0246471 A1 | 9/2014 | Jaworek |
| 2014/0246474 A1 | 9/2014 | Hall |
| 2014/0257252 A1 | 9/2014 | Ishida |
| 2014/0276471 A1 | 9/2014 | Emery |
| 2014/0277334 A1 | 9/2014 | Yu |
| 2014/0291378 A1 | 10/2014 | Shelton, IV et al. |

(56) References Cited

U.S. PATENT DOCUMENTS

| | | |
|---|---|---|
| 2014/0291383 A1 | 10/2014 | Spivey |
| 2014/0305987 A1 | 10/2014 | Parihar |
| 2014/0305992 A1 | 10/2014 | Kimsey |
| 2014/0305995 A1 | 10/2014 | Shelton, IV et al. |
| 2014/0309665 A1 | 10/2014 | Parihar |
| 2014/0309666 A1 | 10/2014 | Shelton, IV |
| 2014/0364890 A1 | 12/2014 | Moody |
| 2015/0053737 A1 | 2/2015 | Leimbach |
| 2015/0053749 A1 | 2/2015 | Shelton, IV |
| 2015/0090760 A1 | 4/2015 | Giordano et al. |
| 2015/0126977 A1 | 5/2015 | Azarbarzin et al. |
| 2015/0133979 A1 | 5/2015 | Johnson |
| 2015/0150547 A1 | 6/2015 | Ingmanson |
| 2015/0173789 A1 | 6/2015 | Baxter, III |
| 2015/0209035 A1 | 7/2015 | Zemlok |
| 2015/0257783 A1 | 9/2015 | Levine et al. |
| 2015/0272575 A1 | 10/2015 | Leimbach |
| 2016/0058443 A1 | 3/2016 | Yates et al. |
| 2016/0095585 A1 | 4/2016 | Zergiebel et al. |
| 2016/0106401 A1* | 4/2016 | Beardsley .............. A61B 17/02 606/1 |
| 2016/0118201 A1 | 4/2016 | Nicholas |
| 2016/0175062 A1 | 6/2016 | Limon |
| 2016/0213436 A1 | 7/2016 | Inoue |
| 2016/0220247 A1 | 8/2016 | Timm et al. |
| 2016/0220268 A1 | 8/2016 | Shelton, IV et al. |
| 2016/0249922 A1 | 9/2016 | Morgan et al. |
| 2016/0249945 A1 | 9/2016 | Shelton, IV |
| 2016/0270780 A1 | 9/2016 | Hall |
| 2016/0310134 A1* | 10/2016 | Contini .............. A61B 17/0686 |
| 2016/0361131 A1 | 12/2016 | Dachs, II |
| 2016/0374666 A1 | 12/2016 | DiNardo et al. |
| 2017/0007254 A1 | 1/2017 | Jaworek |
| 2017/0007255 A1 | 1/2017 | Jaworek et al. |
| 2017/0035421 A1 | 2/2017 | Marczyk |
| 2017/0066119 A1 | 3/2017 | Fu |
| 2017/0079640 A1 | 3/2017 | Overmyer et al. |
| 2017/0079642 A1 | 3/2017 | Overmyer et al. |
| 2017/0128071 A1 | 5/2017 | Holsten et al. |
| 2017/0135711 A1 | 5/2017 | Overmyer |
| 2017/0135717 A1 | 5/2017 | Boudreaux |
| 2017/0164945 A1 | 6/2017 | Chowaniec |
| 2017/0172574 A1 | 6/2017 | Zemlok et al. |
| 2017/0189020 A1 | 7/2017 | Harris et al. |
| 2017/0202595 A1 | 7/2017 | Shelton, IV |
| 2017/0202605 A1 | 7/2017 | Shelton. , IV |
| 2017/0202607 A1 | 7/2017 | Shelton, IV |
| 2017/0207467 A1 | 7/2017 | Shelton, IV |
| 2017/0281167 A1 | 10/2017 | Shelton, IV et al. |
| 2017/0281218 A1 | 10/2017 | Timm |
| 2017/0290583 A1 | 10/2017 | Reed et al. |
| 2017/0296176 A1 | 10/2017 | Contini et al. |
| 2018/0000483 A1 | 1/2018 | Leimbach et al. |
| 2018/0049795 A1 | 2/2018 | Swayze |
| 2018/0049836 A1 | 2/2018 | Shelton, IV et al. |
| 2018/0056496 A1 | 3/2018 | Rubens |
| 2018/0110519 A1 | 4/2018 | Lytle, IV et al. |
| 2018/0133883 A1 | 5/2018 | Nicholas et al. |
| 2018/0250002 A1 | 9/2018 | Eschbach |
| 2018/0271604 A1 | 9/2018 | Grout |
| 2018/0317964 A1 | 11/2018 | Evans et al. |
| 2018/0340806 A1 | 11/2018 | Zemlok |
| 2018/0360486 A1 | 12/2018 | Beaupre |
| 2018/0368822 A1 | 12/2018 | Shelton et al. |
| 2018/0369922 A1* | 12/2018 | Cucchi .................. B23B 13/128 |
| 2019/0000448 A1 | 1/2019 | Shelton, IV |
| 2019/0000577 A1 | 1/2019 | Shelton |
| 2019/0008512 A1 | 1/2019 | Nicholas et al. |
| 2019/0038283 A1 | 2/2019 | Shelton, IV |
| 2019/0053796 A1 | 2/2019 | Miller et al. |
| 2019/0059900 A1 | 2/2019 | Shelton, IV et al. |
| 2019/0059923 A1 | 2/2019 | Tillman |
| 2019/0069887 A1 | 3/2019 | Satti, III et al. |
| 2019/0069895 A1 | 3/2019 | Satti, III et al. |
| 2019/0069896 A1 | 3/2019 | Satti, III et al. |
| 2019/0069917 A1 | 3/2019 | Sholev |
| 2019/0117222 A1 | 4/2019 | Shelton, IV et al. |
| 2019/0125324 A1 | 5/2019 | Scheib |
| 2019/0142421 A1 | 5/2019 | Shelton, IV |
| 2019/0142423 A1 | 5/2019 | Satti, III |
| 2019/0183594 A1 | 6/2019 | Shelton, IV et al. |
| 2019/0206565 A1 | 7/2019 | Shelton, IV |
| 2019/0239966 A1 | 8/2019 | Xu |
| 2019/0261991 A1 | 8/2019 | Beckman |
| 2020/0205817 A1 | 7/2020 | Nielsen et al. |
| 2020/0315725 A1 | 10/2020 | Graves et al. |
| 2020/0315730 A1 | 10/2020 | Zemlok et al. |
| 2020/0405307 A1 | 12/2020 | Shelton. , IV |
| 2021/0204944 A1 | 7/2021 | Satti, III et al. |
| 2021/0220001 A1 | 7/2021 | Heiliger |
| 2021/0322007 A1 | 10/2021 | Satti, III |
| 2022/0061836 A1 | 3/2022 | Parihar |
| 2022/0167982 A1 | 6/2022 | Shelton, IV |
| 2022/0346784 A1 | 11/2022 | Shelton, IV |
| 2023/0000495 A1 | 1/2023 | Barrera |
| 2023/0038169 A1 | 2/2023 | Prema Mohanasundaram |

FOREIGN PATENT DOCUMENTS

| | | |
|---|---|---|
| EP | 0685203 | 12/1995 |
| EP | 0699418 | 3/1996 |
| EP | 0705571 | 4/1996 |
| EP | 1889576 | 2/2008 |
| EP | 206253705/2009 | 5/2009 |
| EP | 2243432 | 10/2010 |
| EP | 2243433 | 10/2010 |
| EP | 2792306 | 10/2014 |
| EP | 3005954 | 4/2016 |
| EP | 3078334 | 10/2016 |
| EP | 3154186 | 4/2017 |
| EP | 3178413 | 6/2017 |
| EP | 3189790 | 7/2017 |
| EP | 2792316 | 1/2018 |
| JP | 5415704 B2 | 11/2013 |
| JP | 2016512055 | 4/2016 |
| WO | WO 2006/112849 | 10/2006 |
| WO | WO 2010/006057 | 1/2010 |
| WO | WO 2017/154007 | 9/2017 |
| WO | WO 2019/045995 | 3/2019 |
| WO | WO 2019/046132 | 3/2019 |
| WO | WO 2021/016006 | 1/2021 |

OTHER PUBLICATIONS

International search report and written opinion for international application PCT/US2018/048020 dated Oct. 30, 2018.

International search report for international application PCT/US2018/046370 dated Nov. 6, 2018.

International search report and written opinion for international application PCT/US2020/018714 dated Aug. 4, 2020.

International Search Report and Written Opinion dated Nov. 13, 2020 for International Application No. PCT/US2020/042033.

International search report and written opinion for international application PCT/US2022/016892 dated May 13, 2022.

Search Report For European Application EP 18849700 dated Jun. 8, 2021.

European Search Report (Sep. 22, 2023) from European Application No. EP 18760198.4.

\* cited by examiner

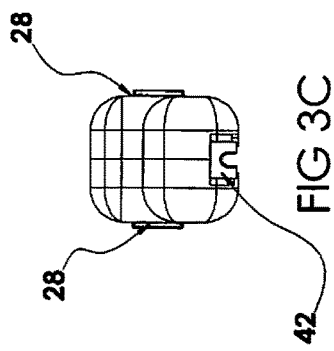
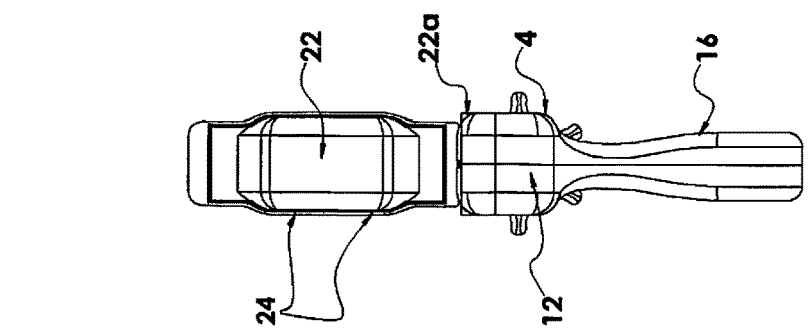
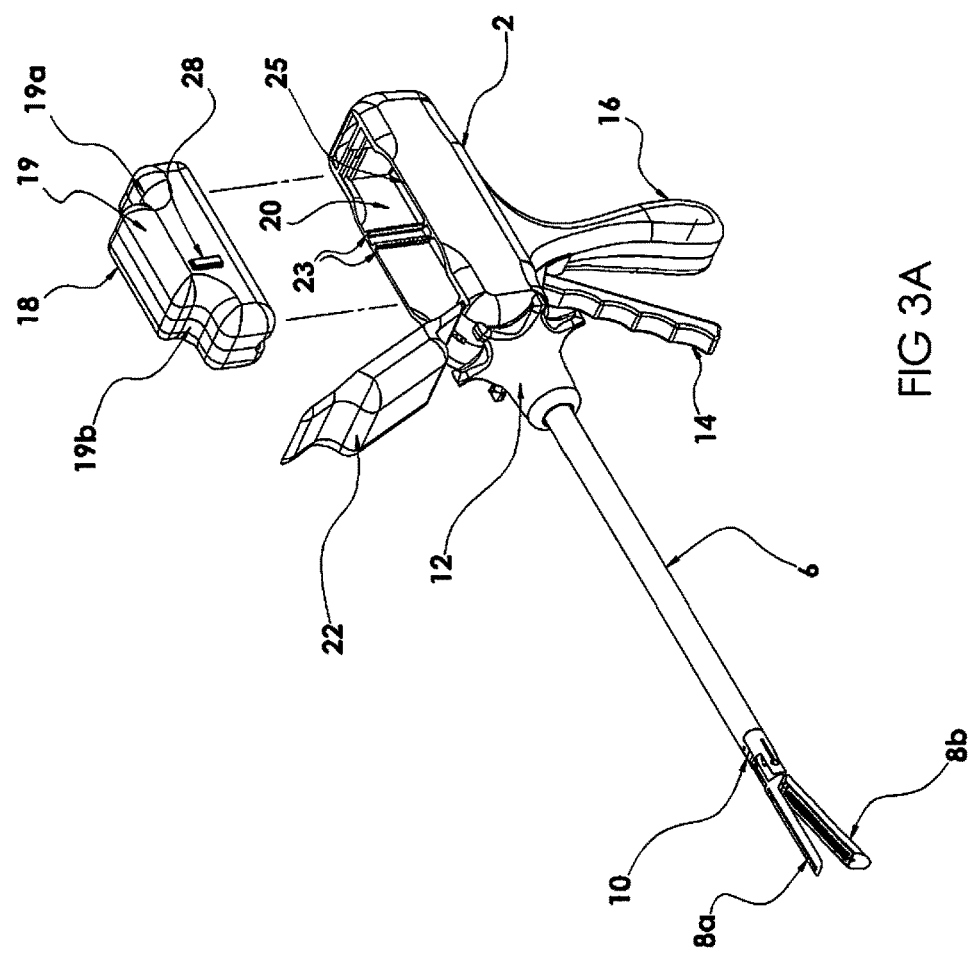

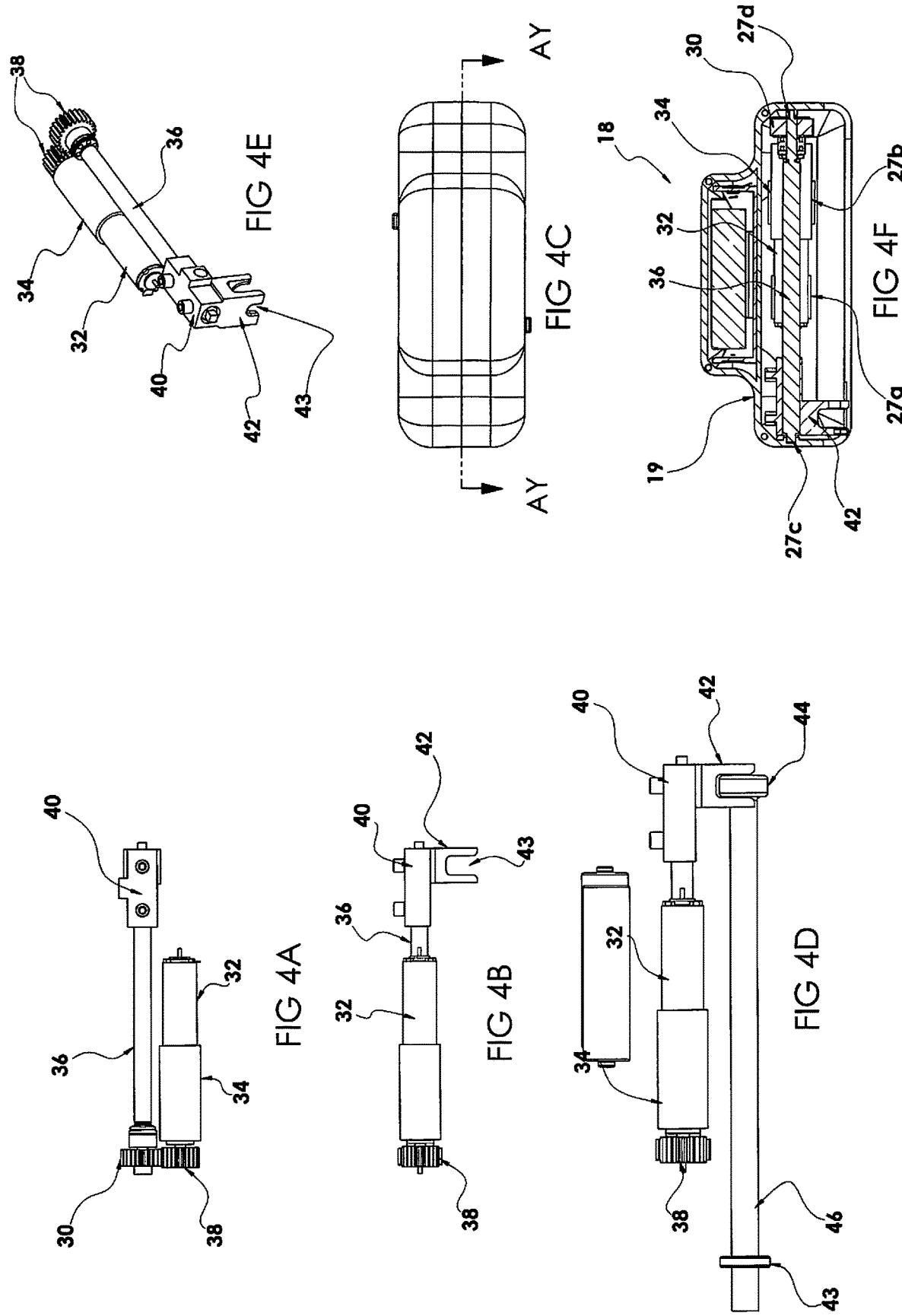

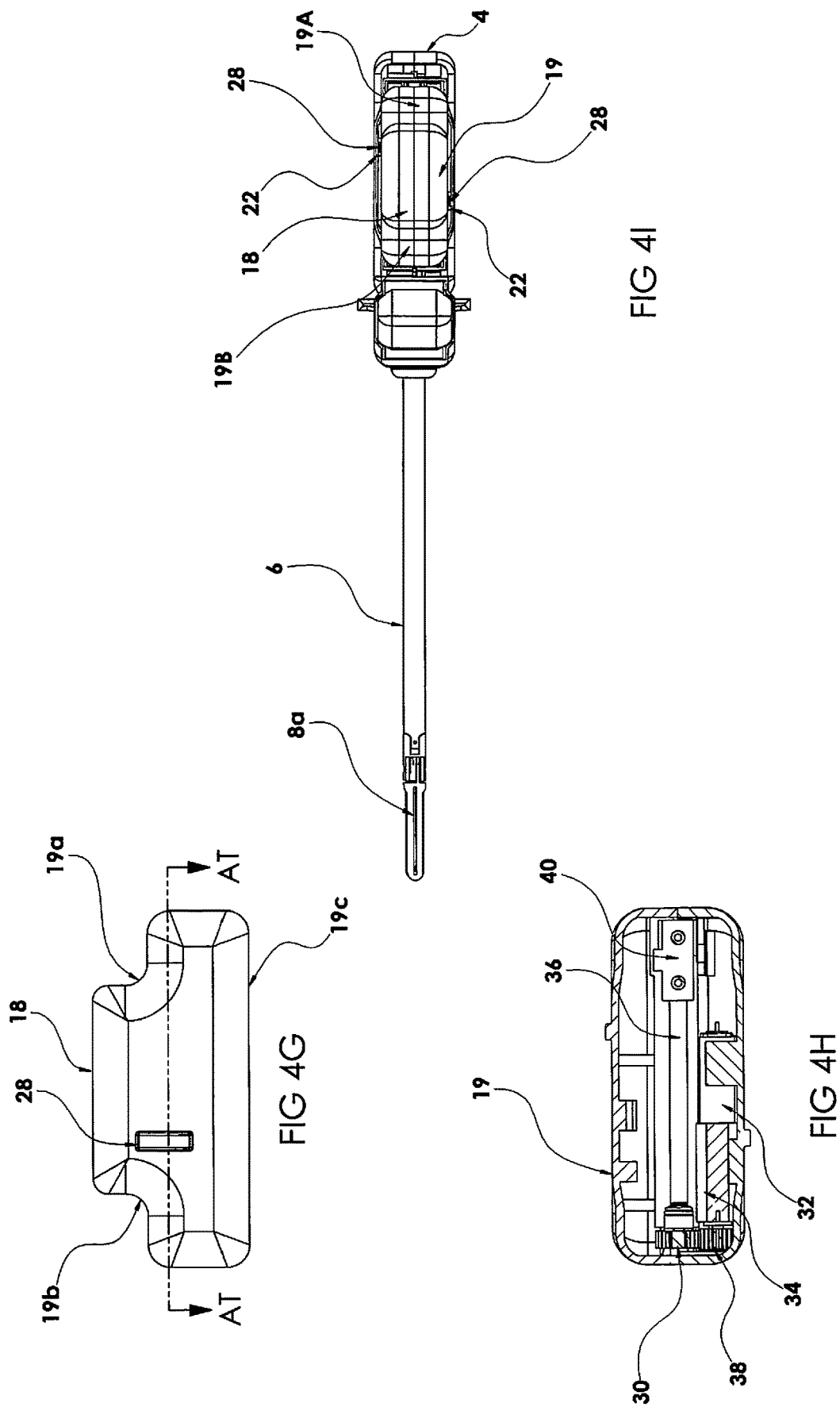

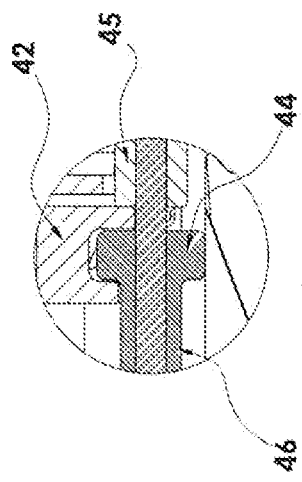
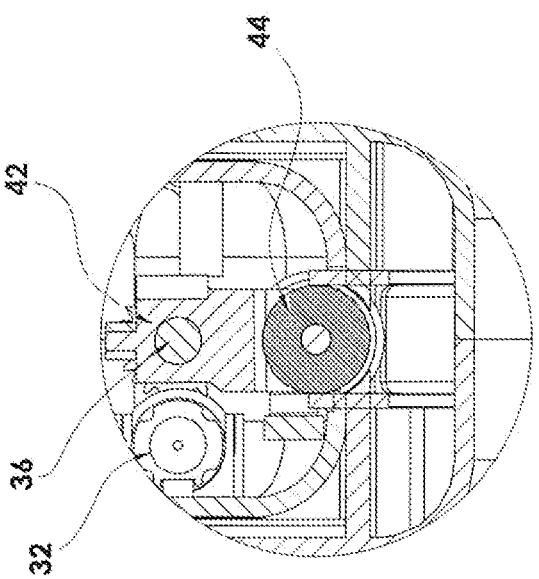
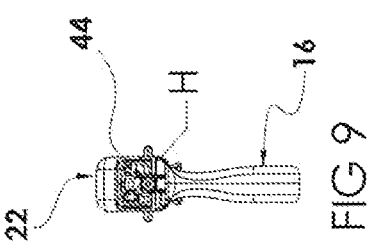
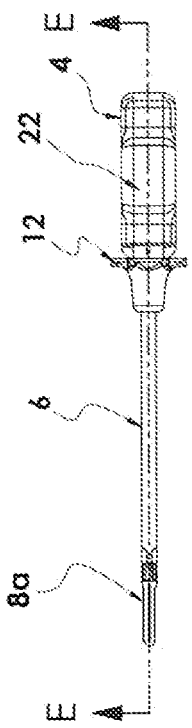
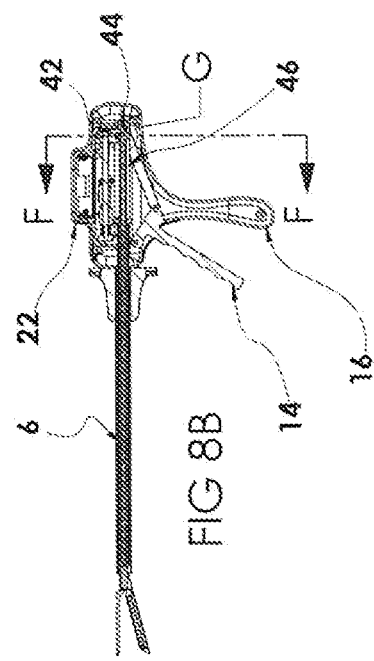

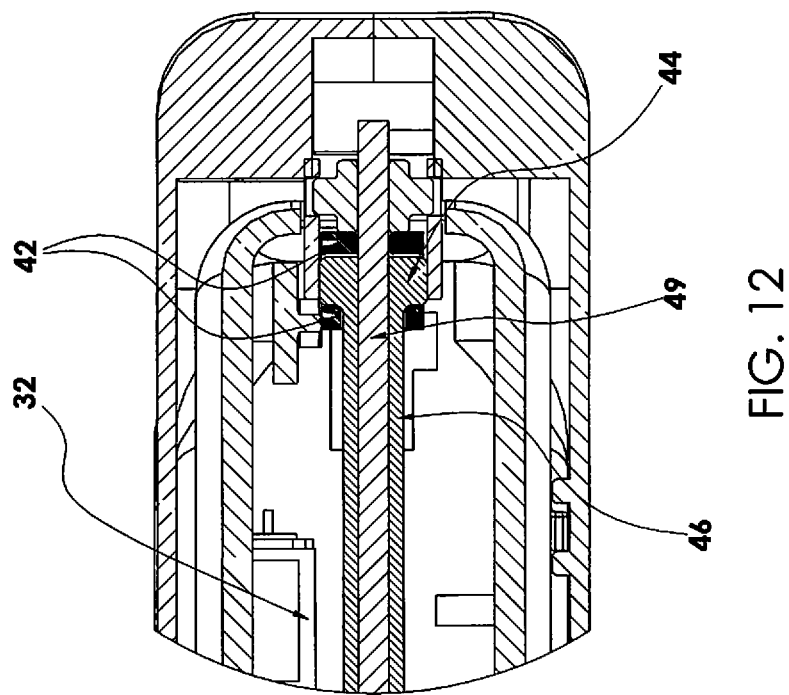
FIG. 12
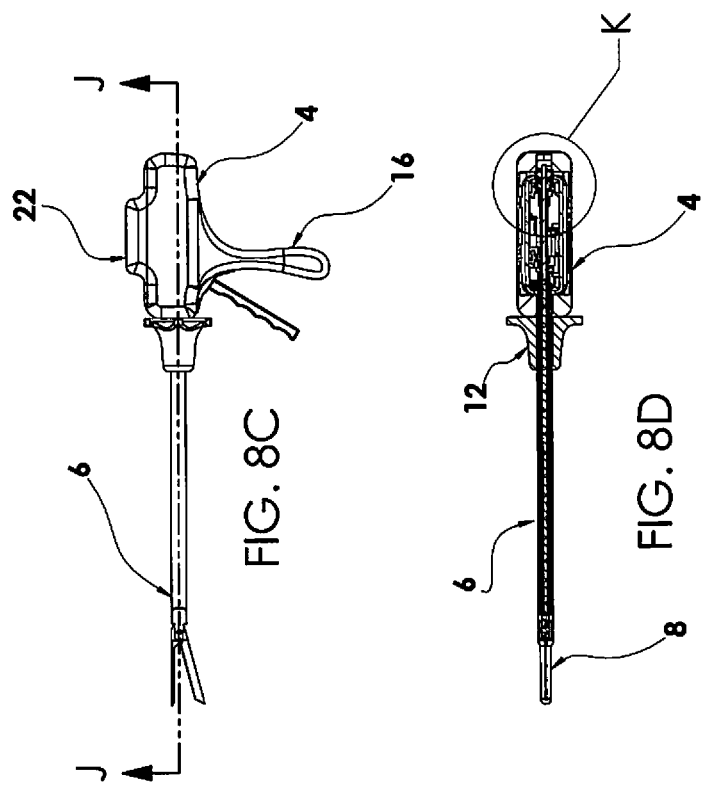
FIG. 8C
FIG. 8D

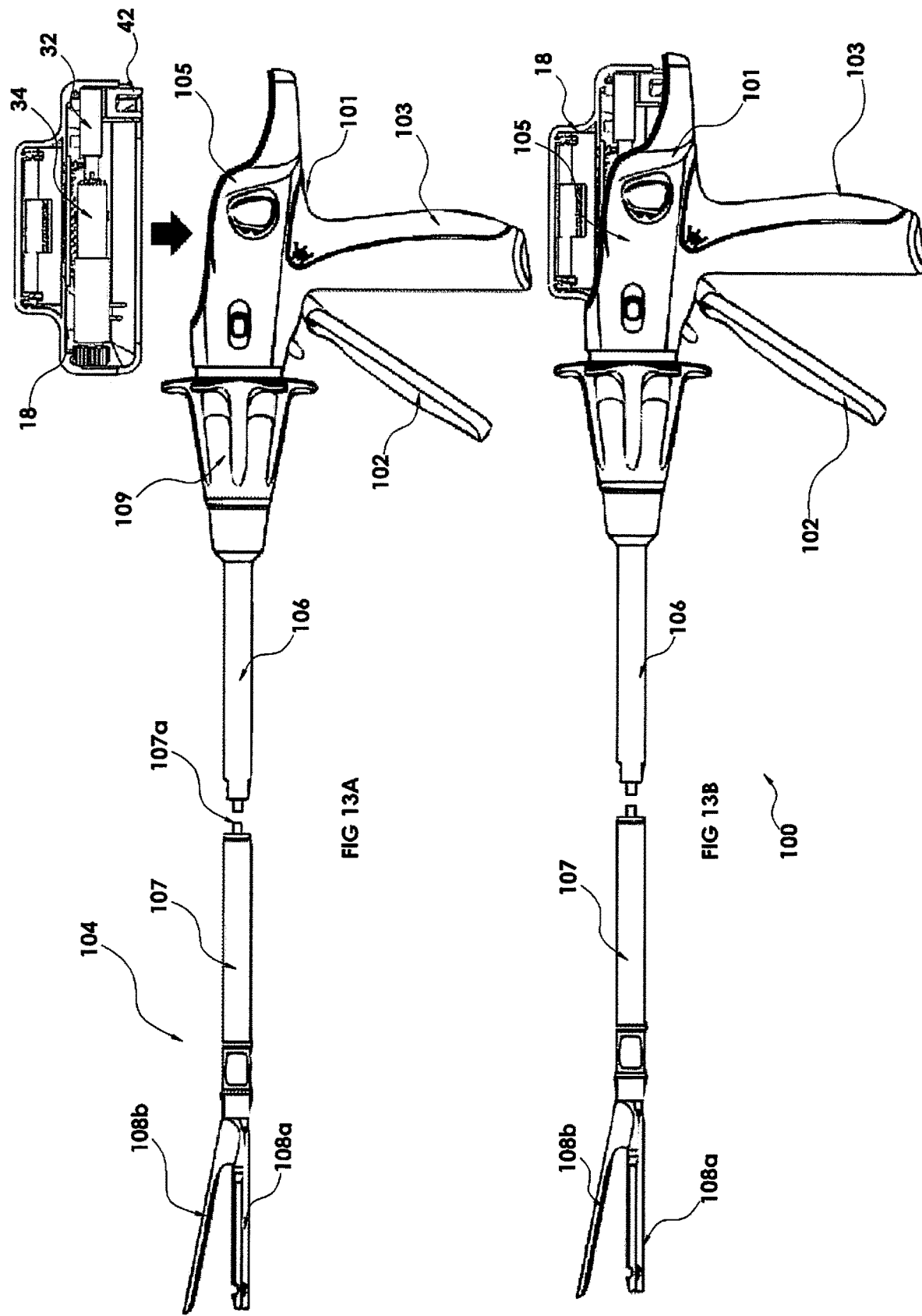

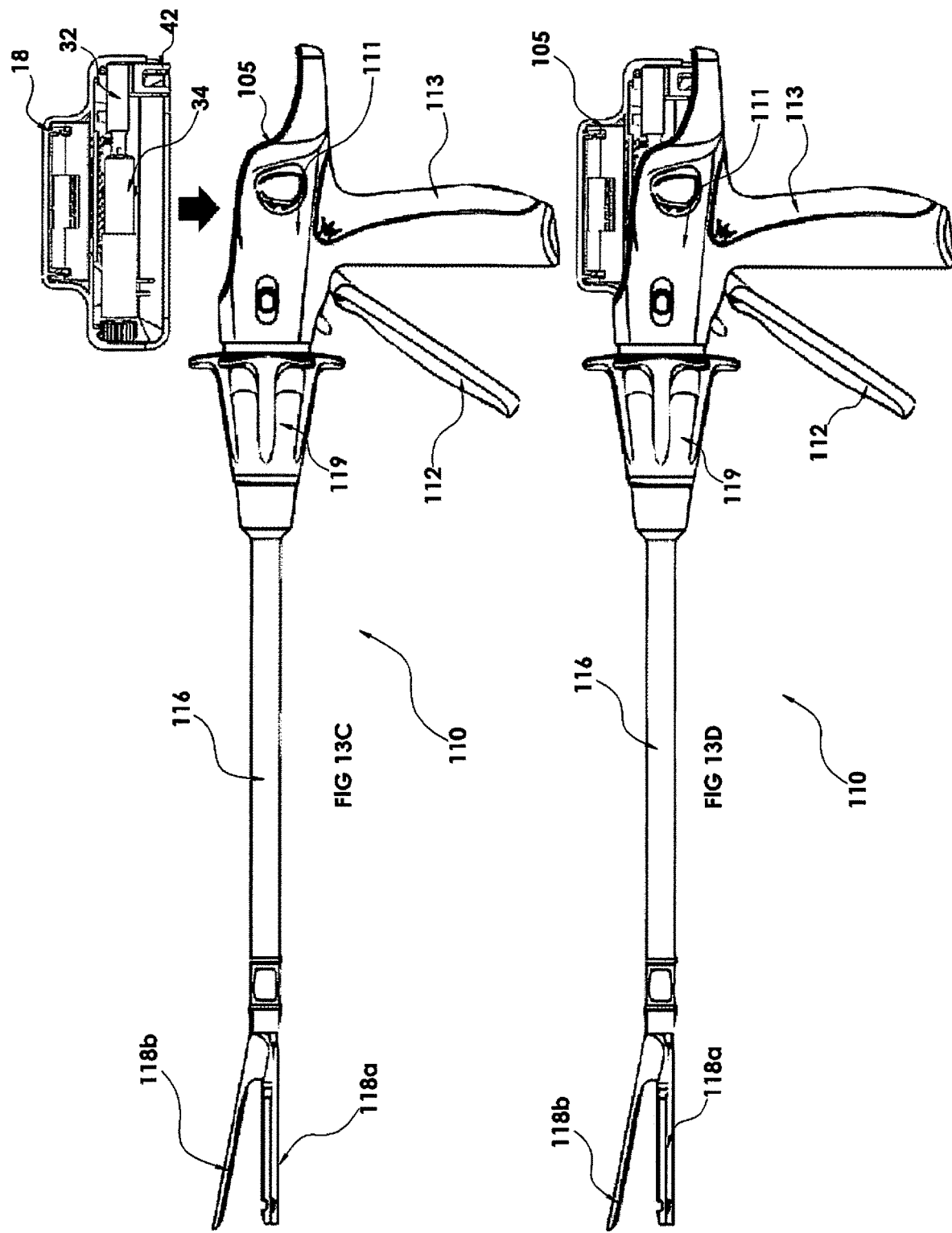

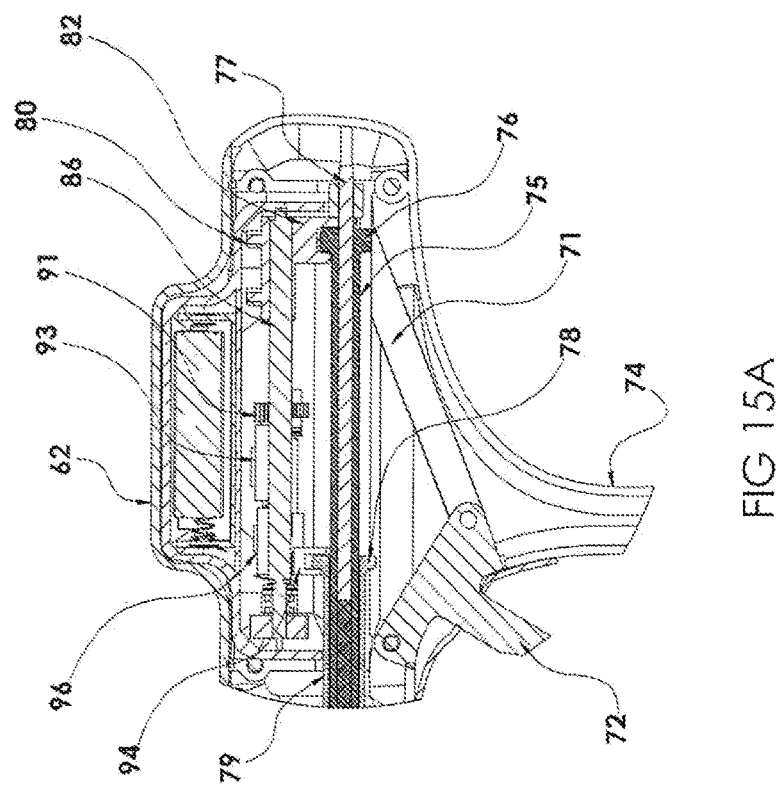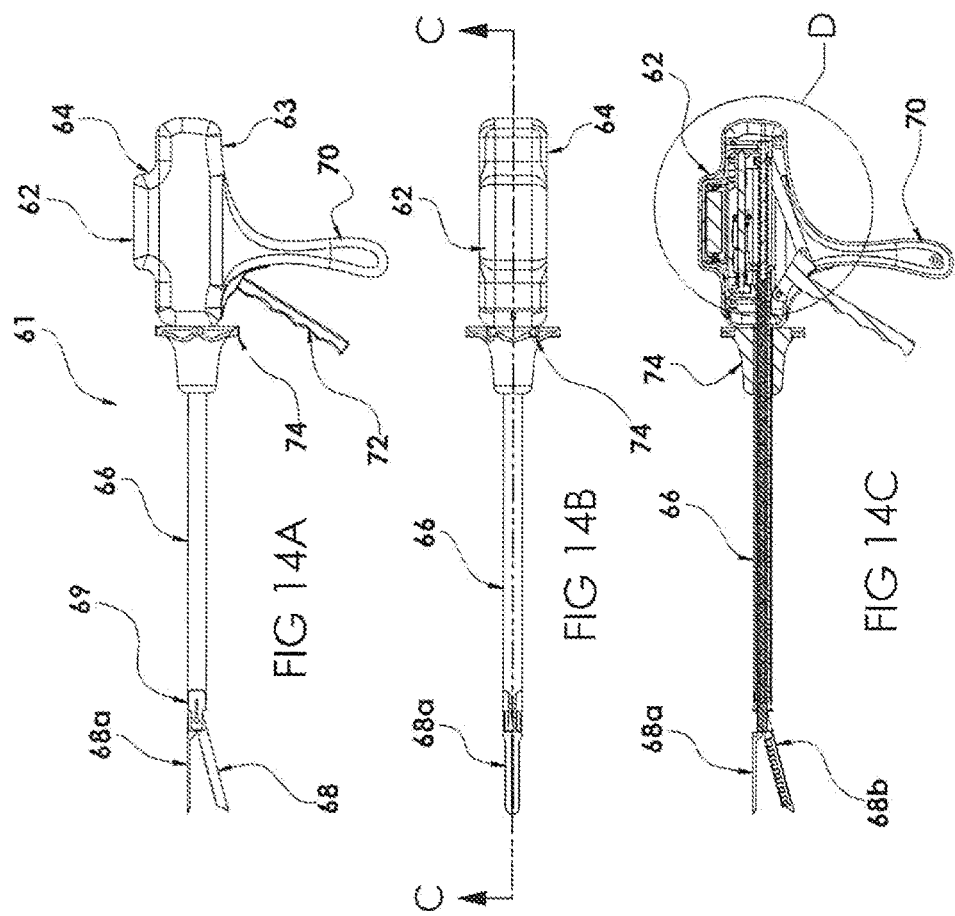

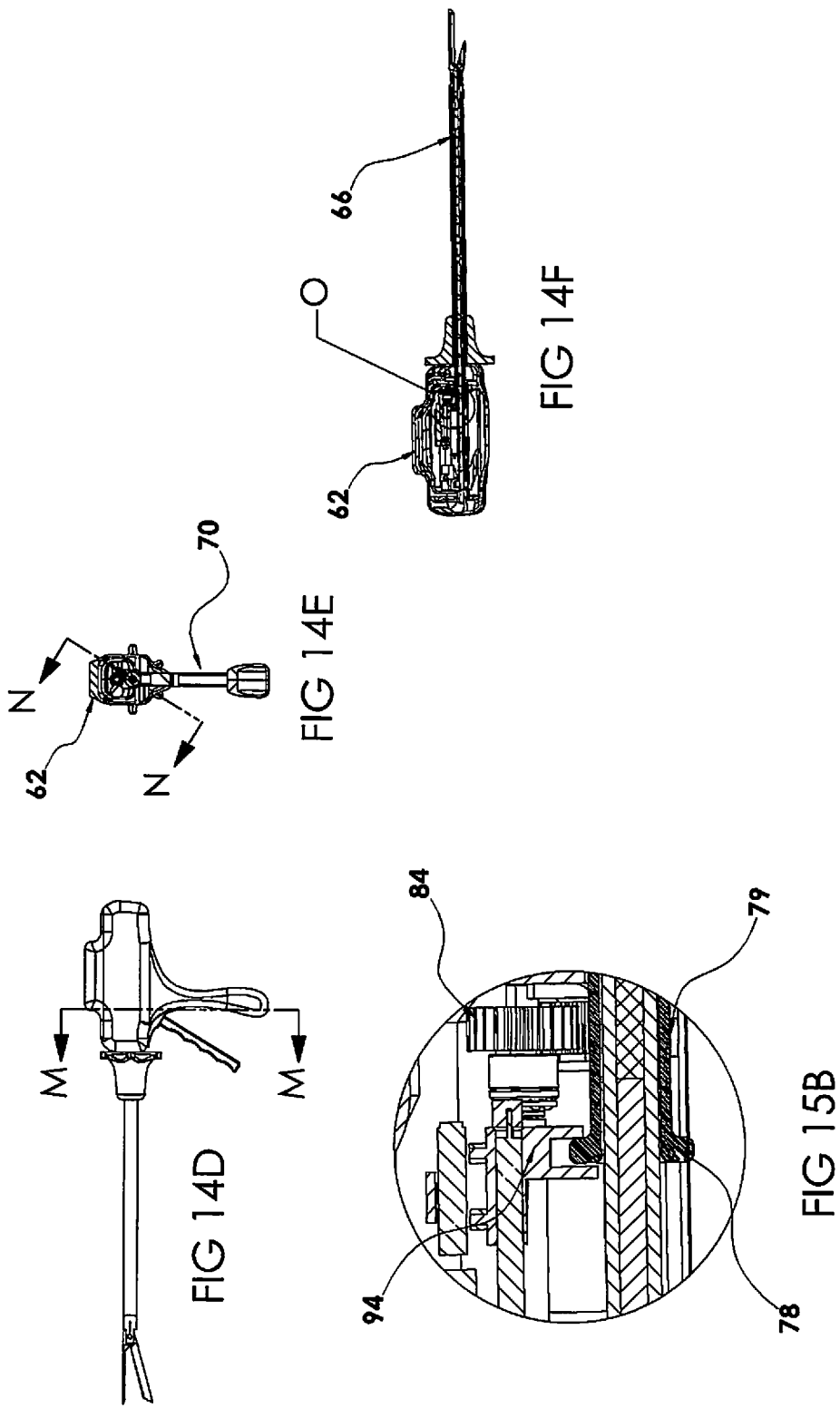

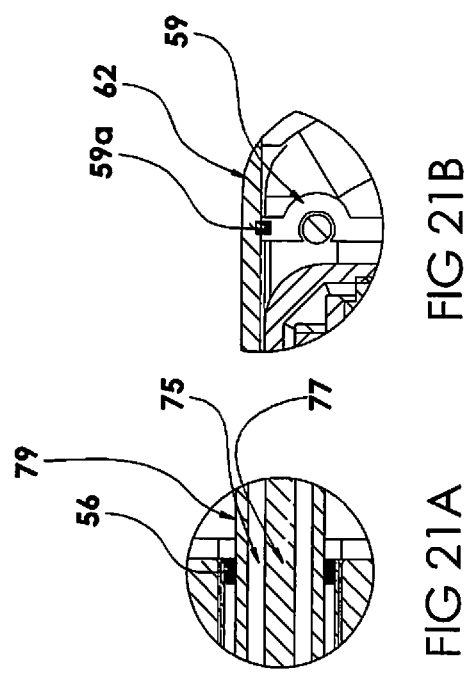
FIG 21A
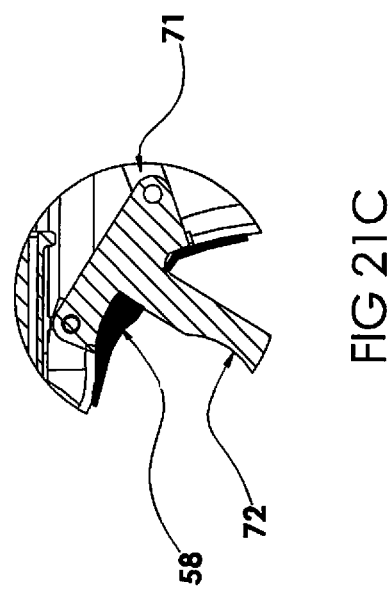
FIG 21B
FIG 21C
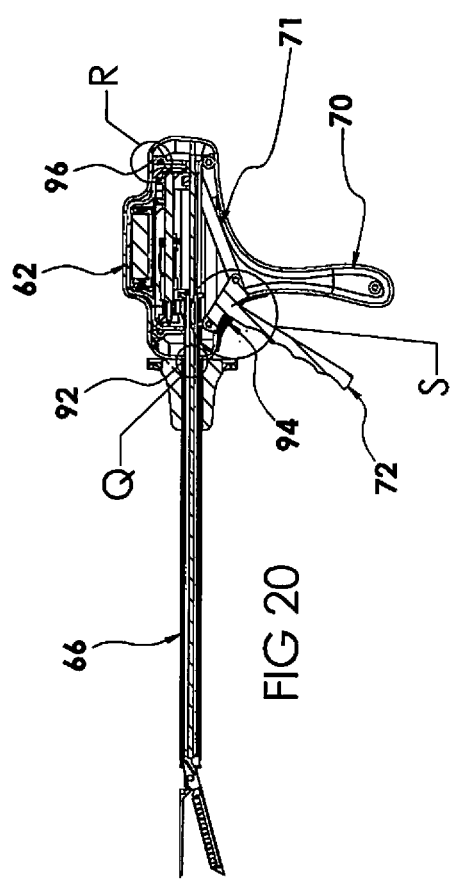
FIG 20

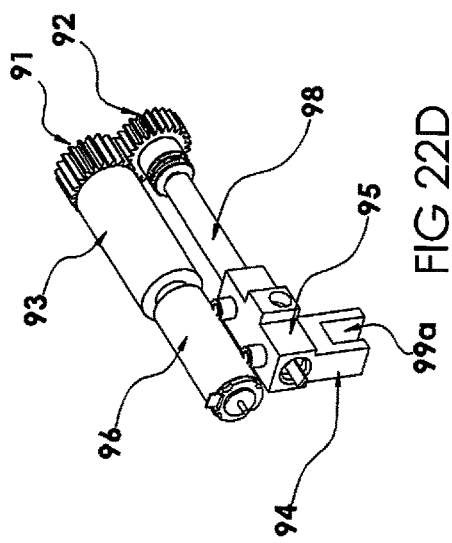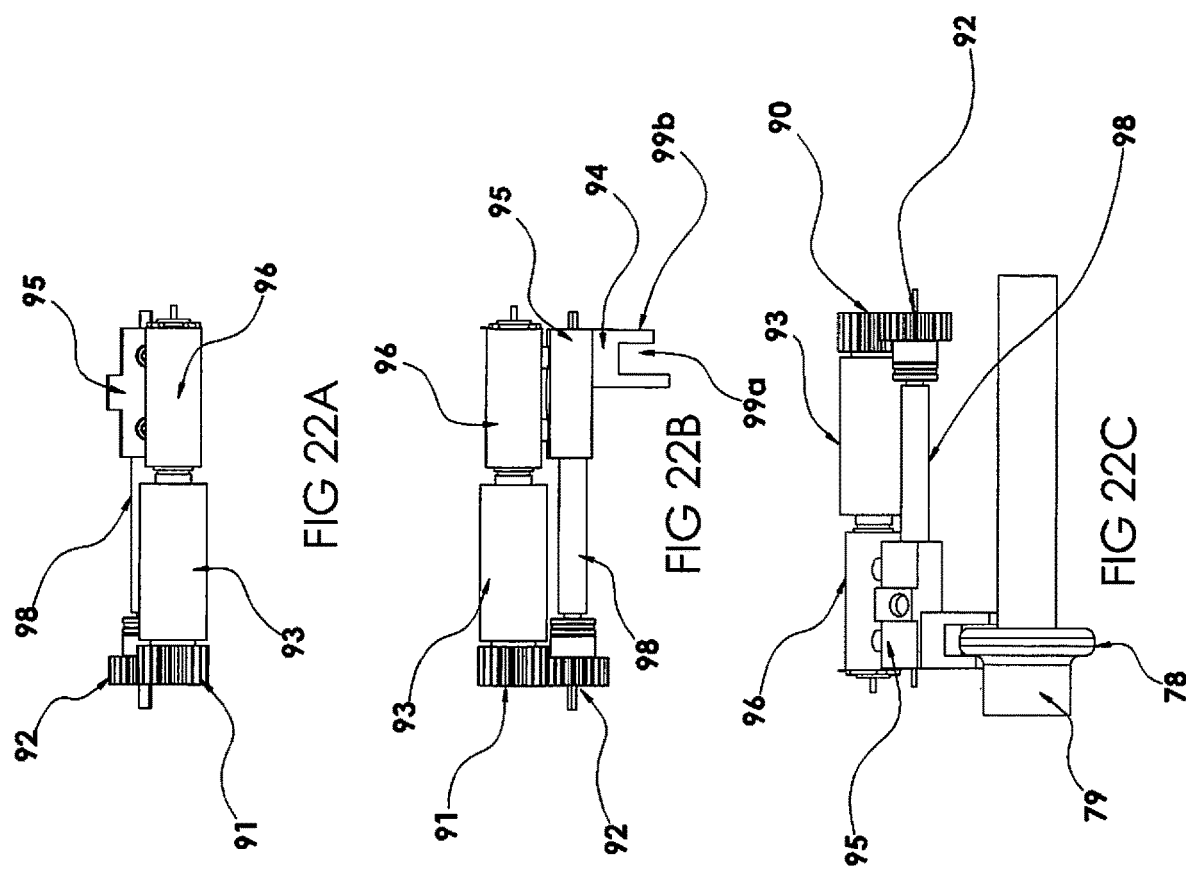

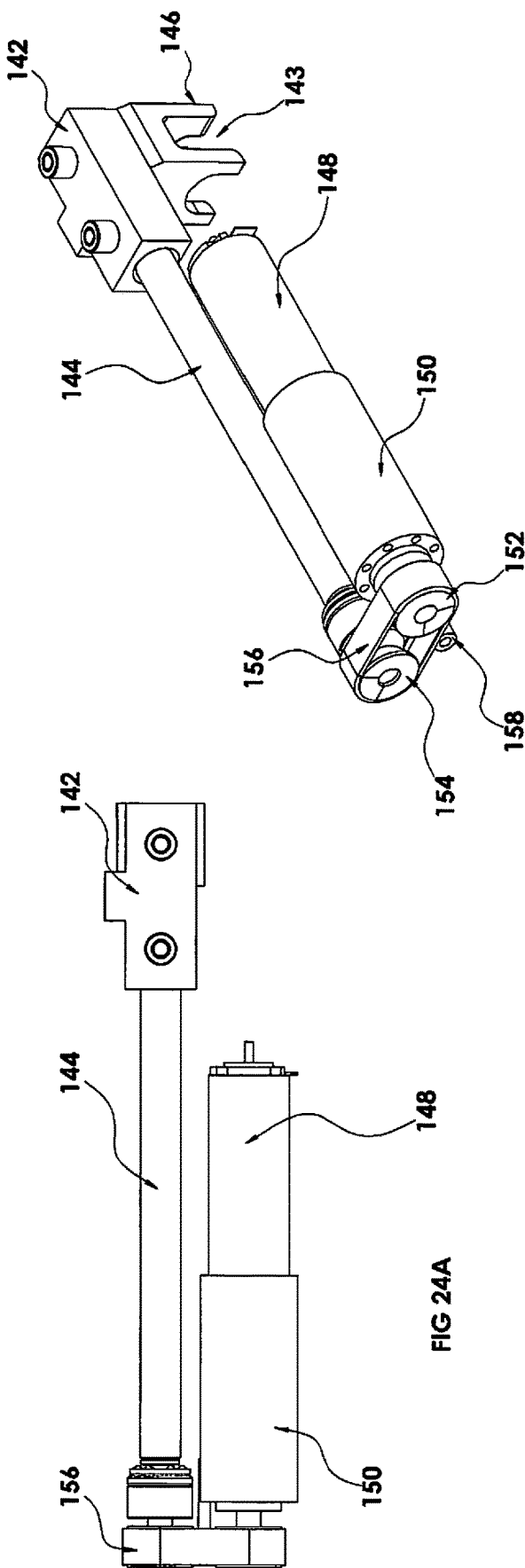
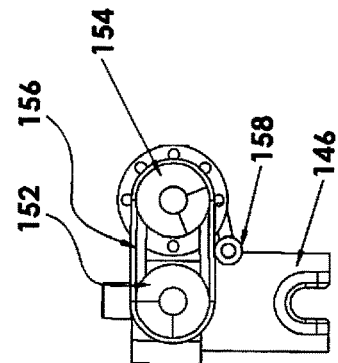
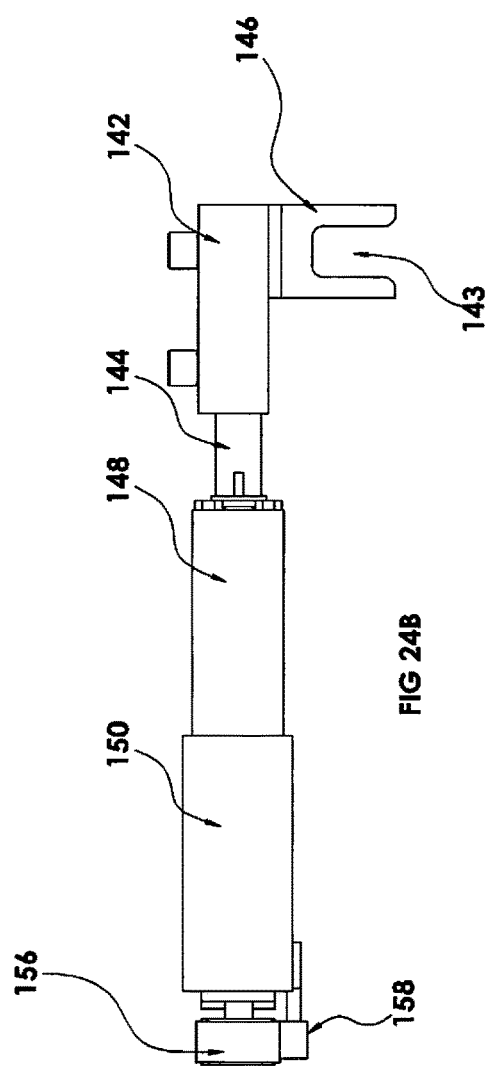
FIG 24A
FIG 24B
FIG 24C
FIG 24D

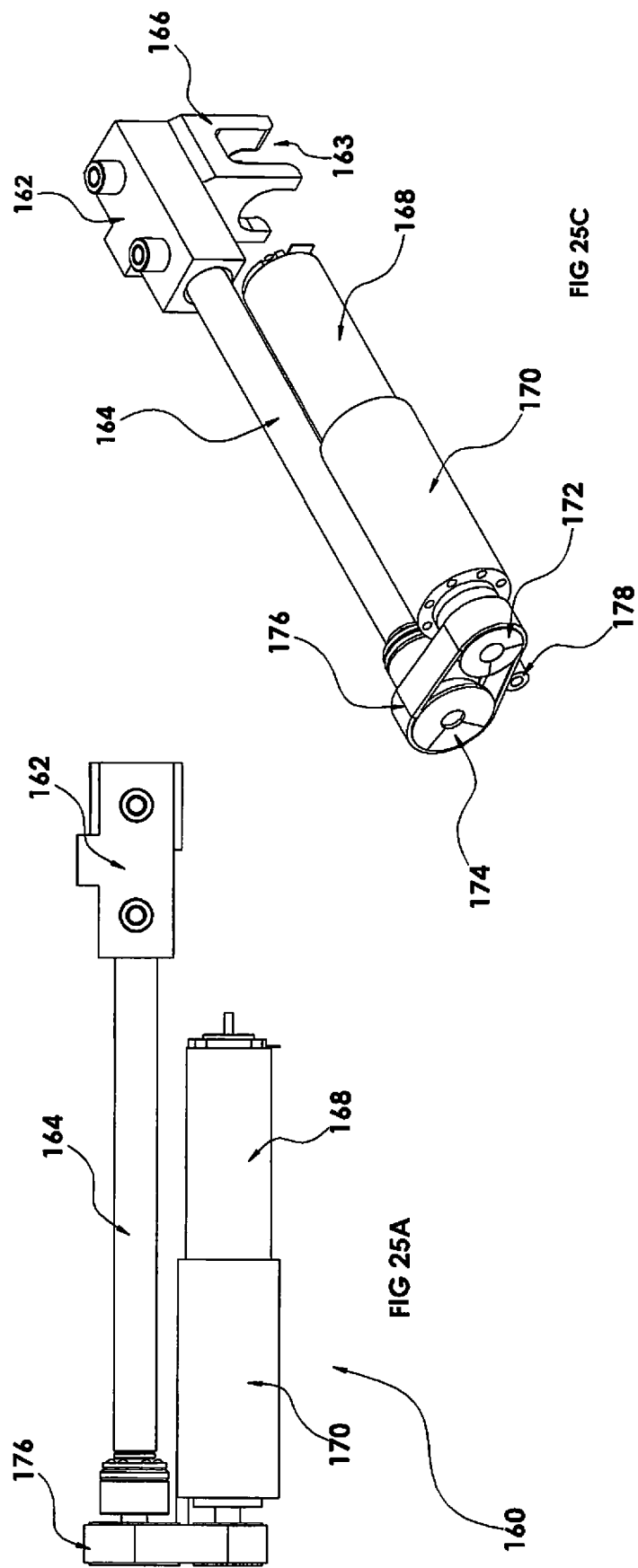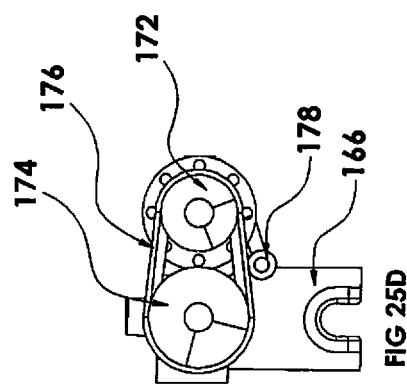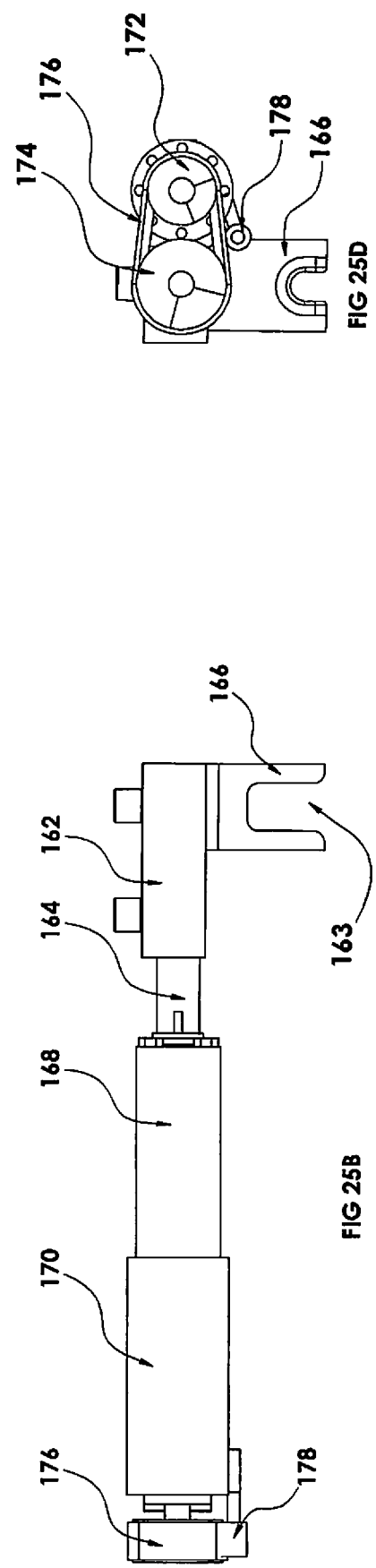

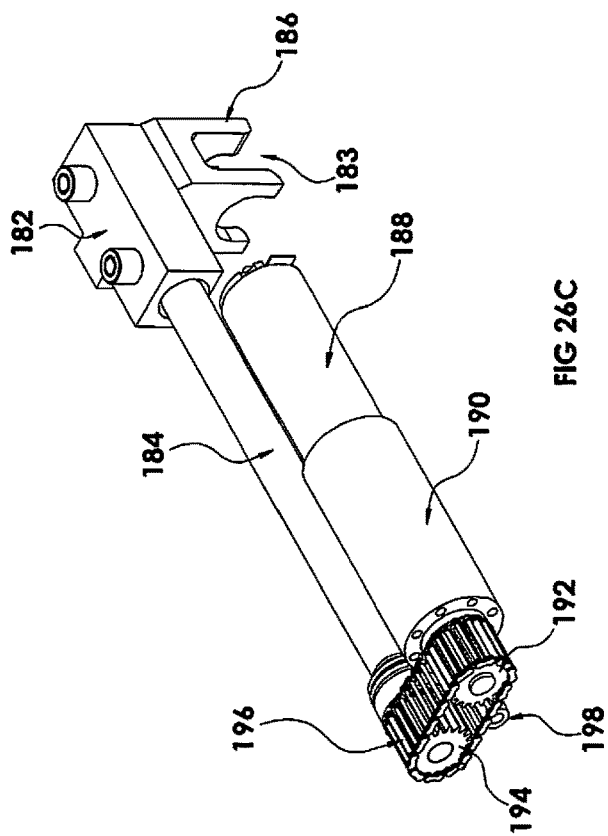
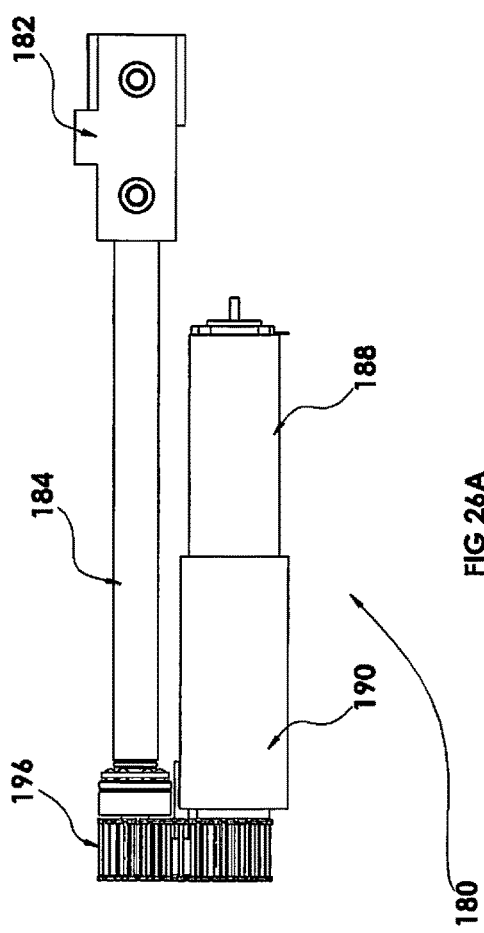
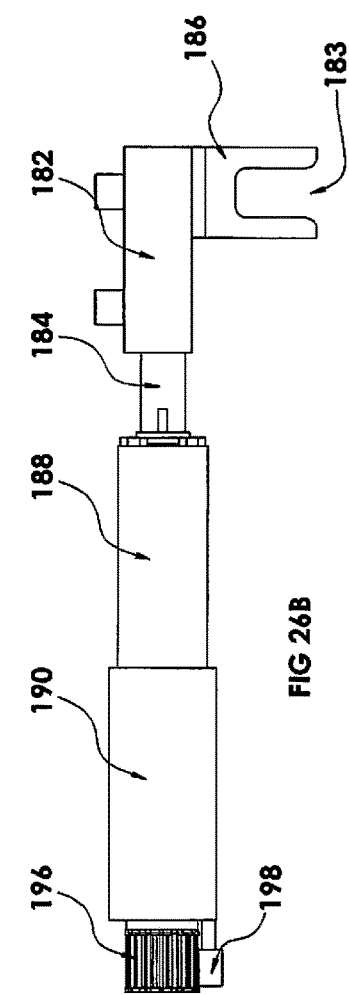
FIG 26C
FIG 26D
FIG 26A
FIG 26B

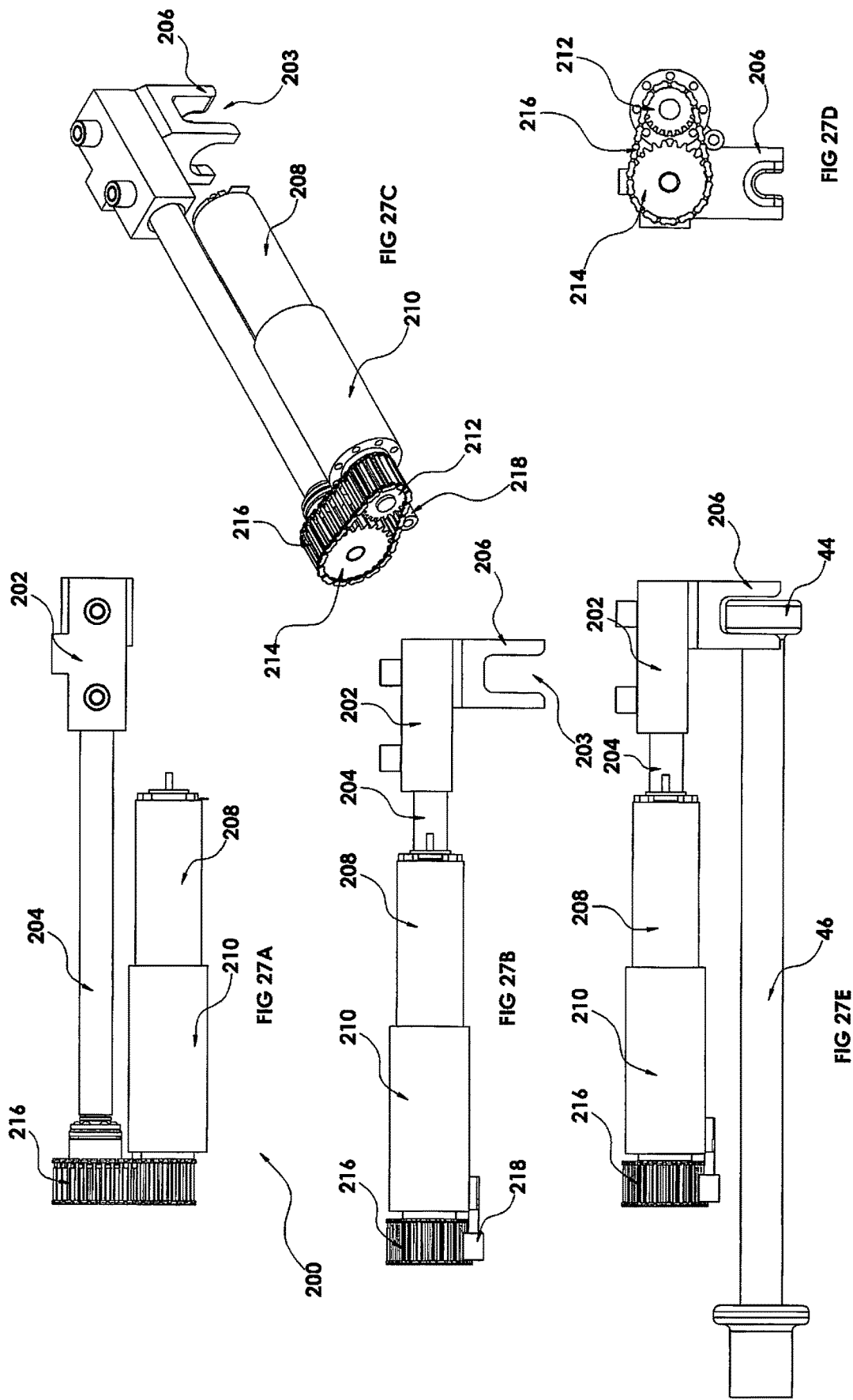

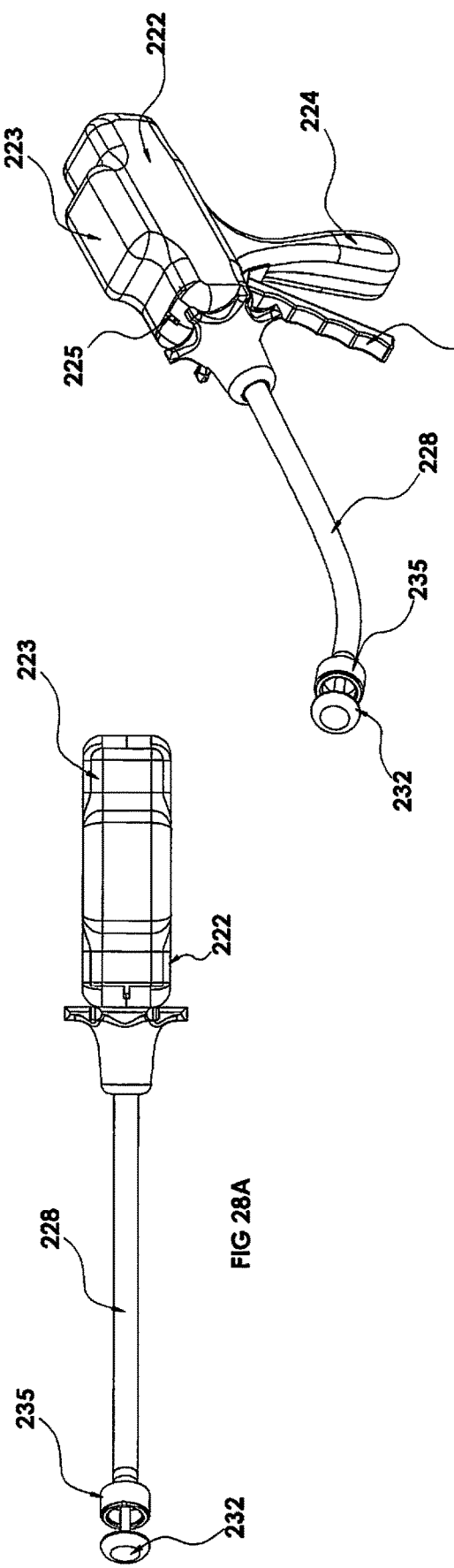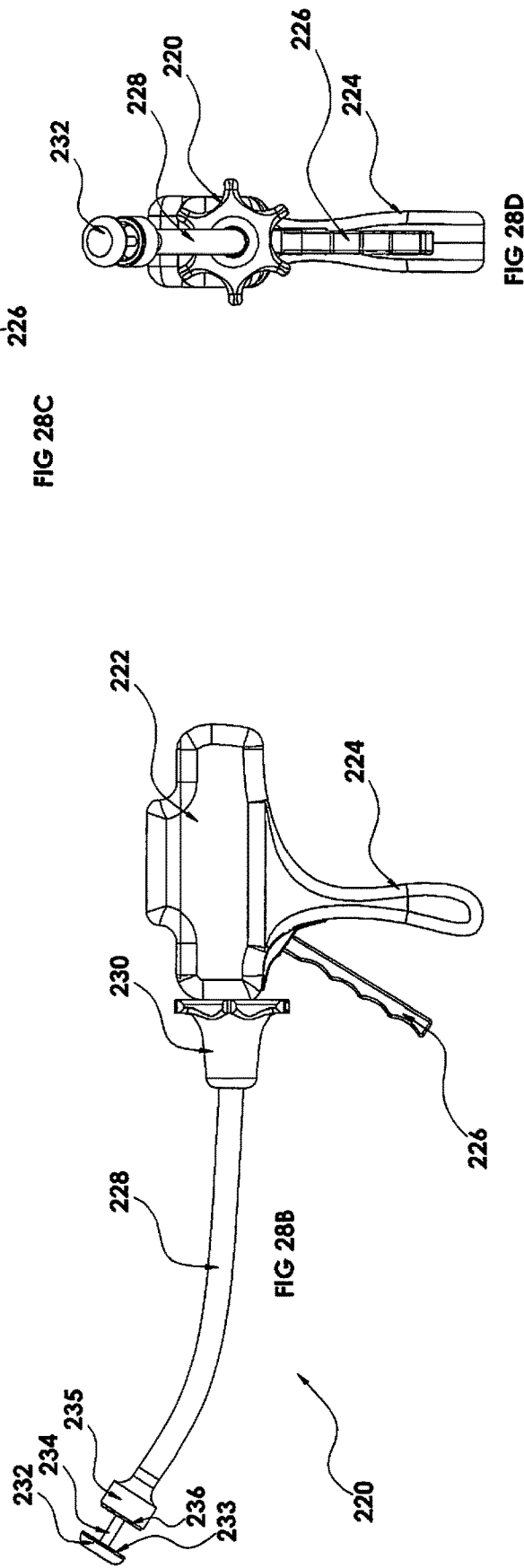

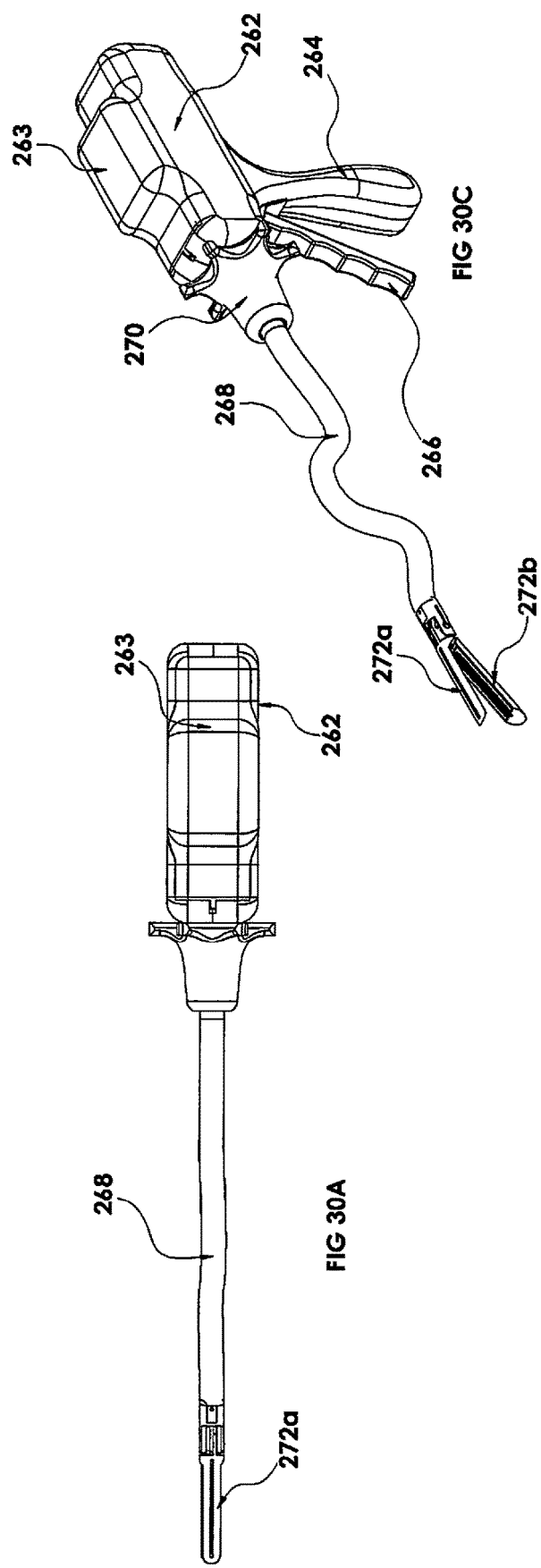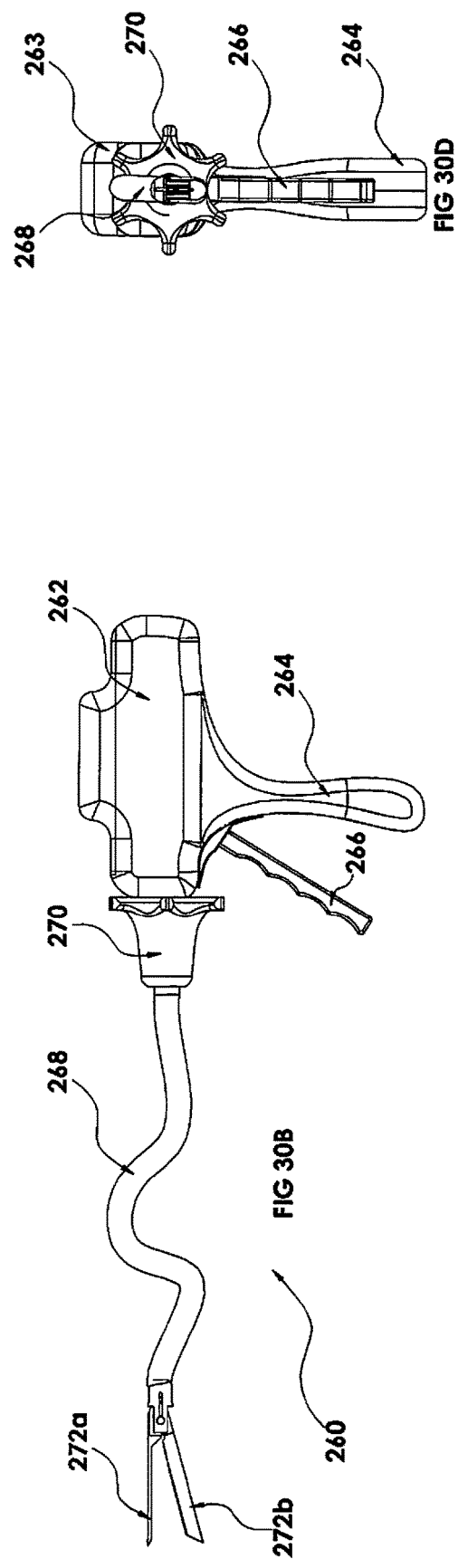

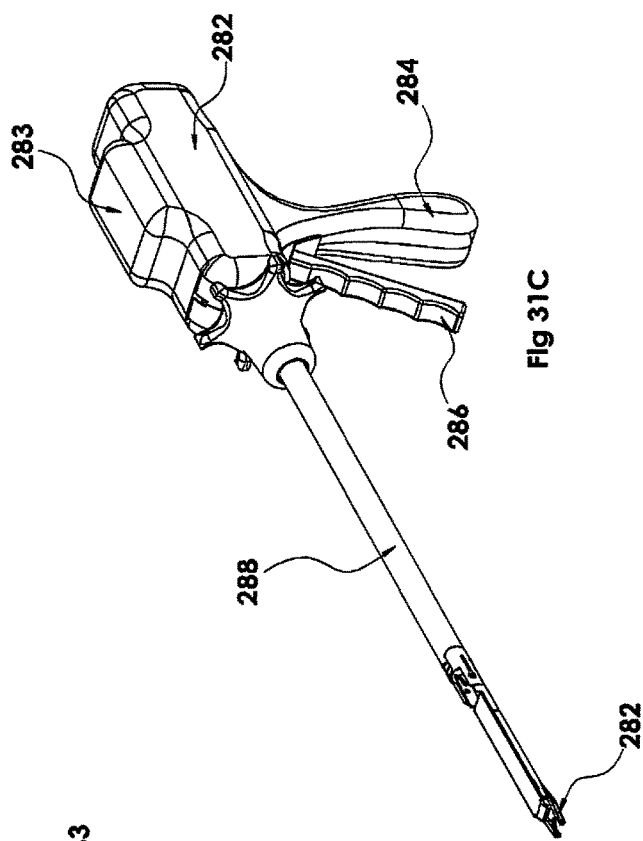
Fig 31C
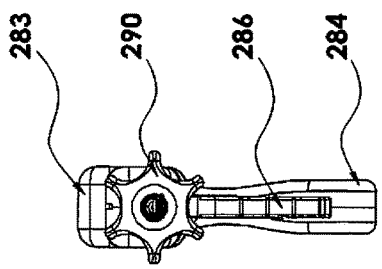
FIG 31D
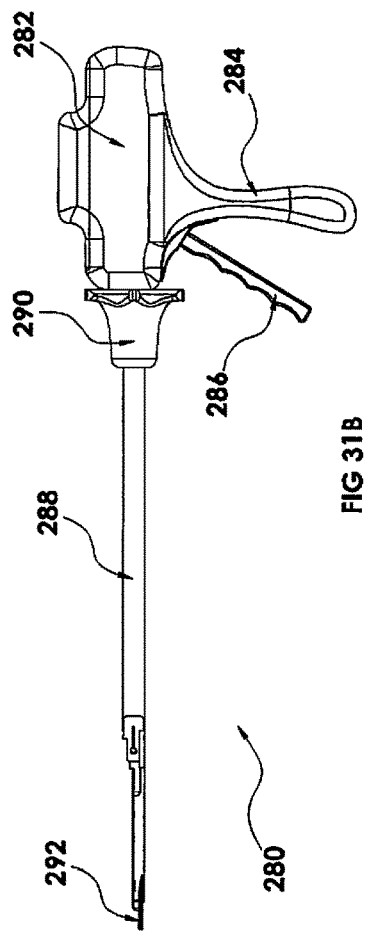
FIG 31A
FIG 31B

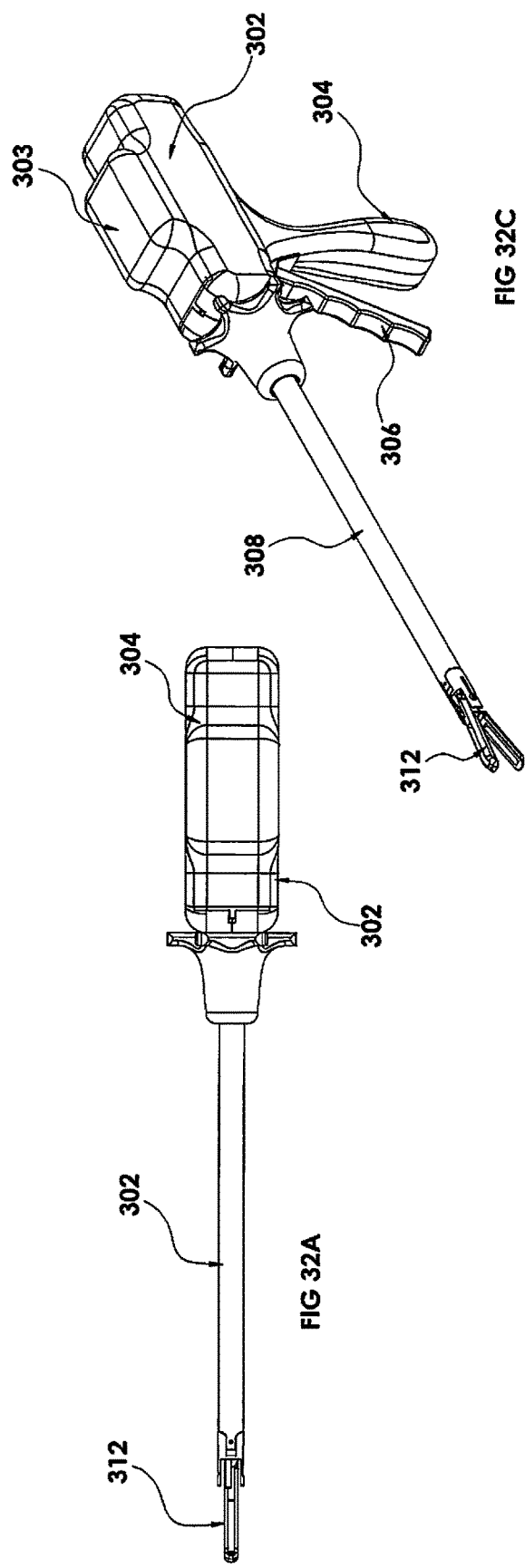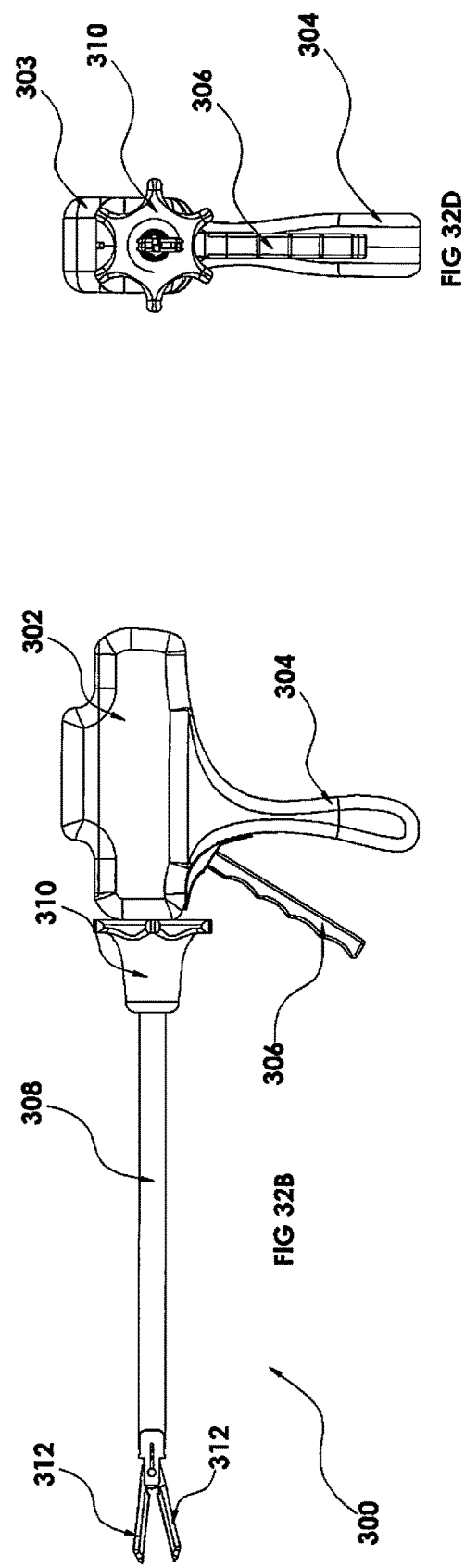

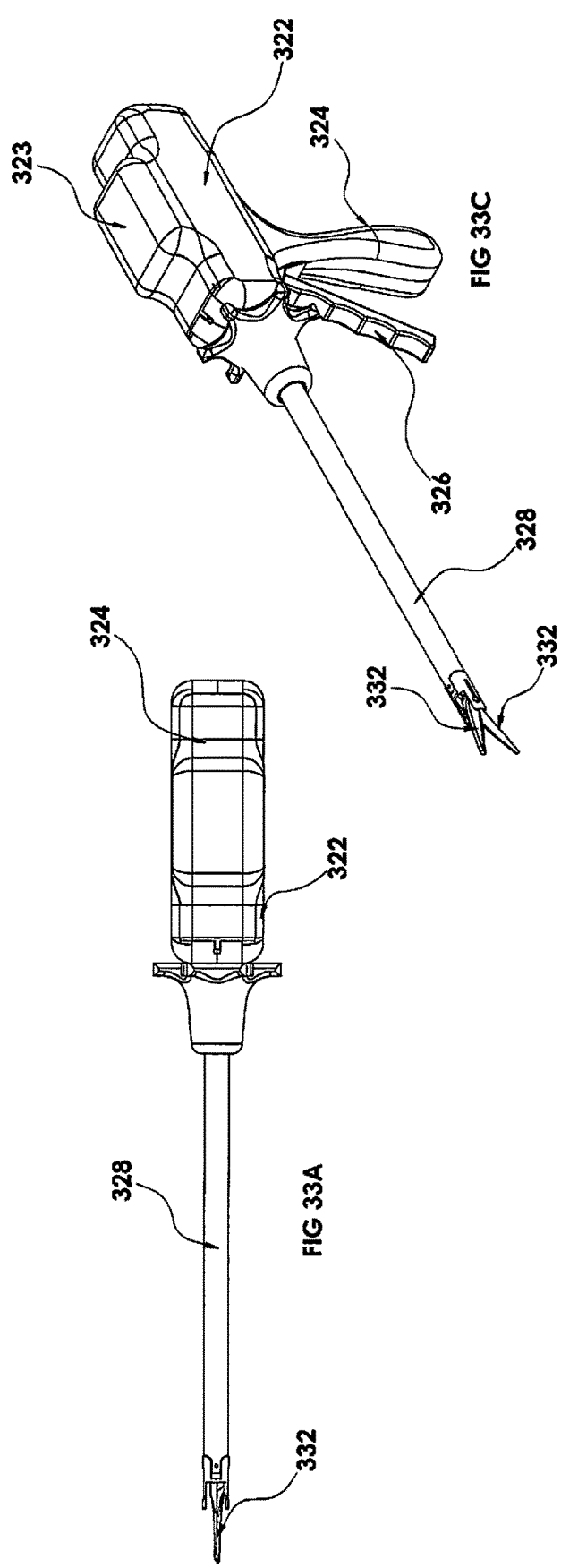

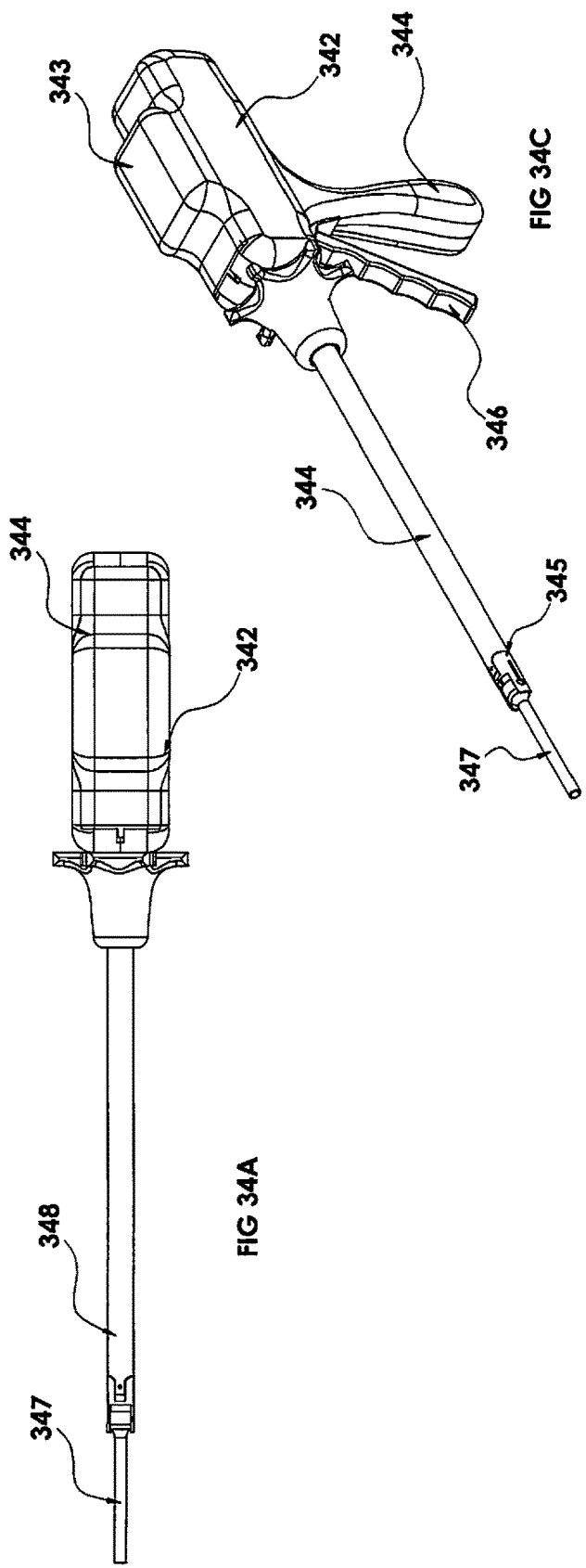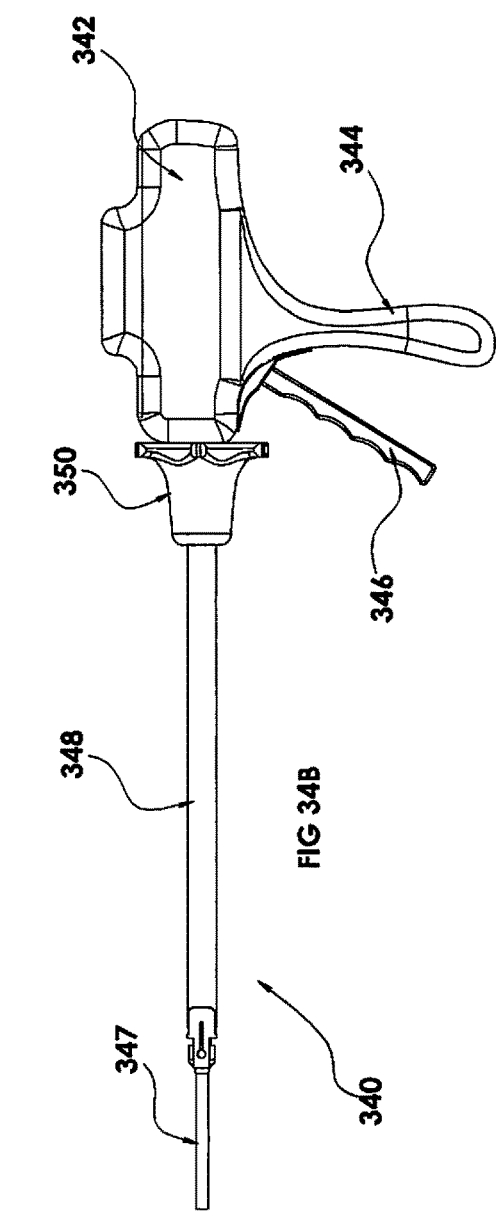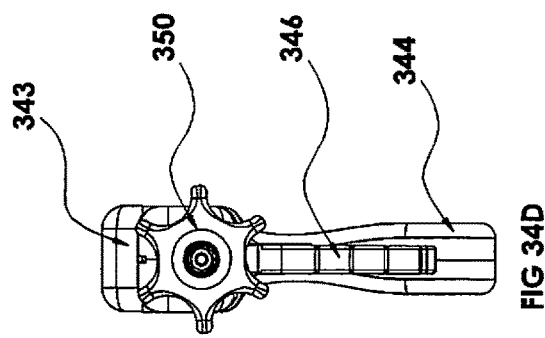

SURGICAL STAPLER WITH REMOVABLE POWER PACK

BACKGROUND OF THE INVENTION

This application is a continuation of application Ser. No. 17/206,861, filed Mar. 19, 2021, which is a continuation of application Ser. No. 15/965,737, filed Apr. 27, 2018, now U.S. Pat. No. 10,966,720, which claims priority from provisional application Ser. No. 62/553,297, filed Sep. 1, 2017 and from provisional application Ser. No. 62/616,045, filed Jan. 11, 2018. The entire contents of each of these applications are incorporated herein by reference.

1. Field of the Invention

This application relates to surgical staplers, and more particularly, to surgical staplers having removable power packs to effect firing of the staples.

2. Background

Surgical staplers are used in various medical applications where a device is needed to join and dissect anatomical tissue. However, there are drawbacks and costs associated with use of surgical staplers. Currently staplers are either fully disposable, reusable or partially reusable. Due to contamination during the surgical procedure, e.g., exposure to the patient's body fluids, the staplers are required to be sterilized after use, a time consuming and expensive process, with possible risks of infection if not properly sterilized as contaminants adhered to the surgical stapler from a previous use could be transferred to another patient. To avoid the risks of resterilization, some surgical staplers are disposed after use in the surgical procedure. These staplers can be reloaded to fire multiple cartridges of staples, but after the procedure, the staplers are discarded. However, the practice of using single use disposable surgical staplers is costly.

In certain procedures, high forces are required to fire the staples through tissue into contact with the anvil for formation This is compounded when multiple rows of staples are fired either simultaneously or sequentially from the stapler. Therefore, powered staplers have been introduced to reduce the force requirements of the user. Such powered staplers have motor driven mechanisms (assemblies) to advance components within the stapler to fire the staples from the cartridge through tissue. Such powered staplers, if reusable, are subject to the same aforementioned costs and risk of resterilization. However they suffer from additional drawbacks since the sterilization process and/or heat or chemicals used in the sterilization process can damage the electronic components of the drive assemblies, which may shorten the lifespan of the surgical stapler or adversely affect its function if resterilization compromises the function of the motor or drive assembly. If the stapler is disposable, the stapler becomes more costly since the electronic components, which add to the cost of the stapler, are also discarded with the stapler.

It would be advantageous to provide a cost effective, efficient, simple to use and advanced assemblies for powering surgical instruments which overcome the drawbacks of manual actuation without suffering from the disadvantages of current power driven staplers.

SUMMARY

The present invention overcomes the deficiencies and disadvantages of the prior art. The present invention advantageously provides surgical staplers that overcome the drawbacks discussed above by having a fully enclosed and removable power pack. The surgical staplers according to the present disclosure may be used multiple times without the need to sterilize the power pack between uses because the power pack is fully enclosed and sealed by the surgical stapler handle assembly or housing, thereby preventing contact between the power pack and the patient and/or patient's bodily fluids or the like. Thus, the surgical staplers of the present disclosure advantageously reduce the time, resources and/or costs for preparing the surgical stapler for its next use. The present disclosure also provides power packs that are cost effective, efficient and easily loadable into surgical staplers where they engage structure in the housing to effect varied functions of the stapler.

In accordance with one aspect of the present disclosure, a surgical fastener applier is provided comprising a housing containing a compartment therein and an elongated member extending distally from the housing. A first jaw and a second jaw are positioned at a distal portion of the elongated member, wherein at least the first jaw is movable with respect to the second jaw to clamp tissue between the first and second jaws. A firing mechanism is positioned within the housing and is movable between a first position and a second firing position, wherein in the second position, the firing mechanism effects firing of fasteners into the tissue clamped between the first and second jaws. A cover on the housing is openable to access the compartment within the housing and a power pack is removably loadable into the compartment, the power pack having a motor and an engagement member removably engageable with the firing mechanism within the compartment when the power pack is loaded into the compartment to effect movement of the firing mechanism from the first position to the second firing position.

In some embodiments, a first seal to seal about the cover in the closed position is provided to protect the power pack positioned within the housing and/or the apparatus includes a second seal to block passage of body fluids from the elongated member into the compartment.

In some embodiments, the power pack has a housing and one of the housing or the compartment has at least one external rib and another of the housing or the compartment has at least one groove to receive the rib to guide the power pack within the compartment. Other guide structures could alternatively be provided.

In some embodiments, the power pack includes a second engagement member removably engageable with an articulating mechanism of the surgical fastener applier to effect articulation of the first and second jaws from a linear position to a position angled with respect to a longitudinal axis of the elongated member. The power pack can include a second motor and the second motor can effect linear movement of the articulation mechanism of the surgical fastener applier.

In some embodiments, the power pack includes a gear mechanism powered by the motor, wherein rotation of a motor shaft of the motor effects rotation of the gear mechanism which effects linear movement of the firing mechanism of the surgical fastener applier. In other embodiments, the power pack includes a drive belt powered by the motor, wherein rotation of a motor shaft of the motor effects rotation of a first disc which moves the drive belt to effect linear movement of the firing mechanism of the surgical fastener applier.

In accordance with another aspect of the present disclosure, a surgical fastener applier is provided comprising a housing containing a compartment therein, an elongated member extending distally from the housing and a jaw assembly including a first jaw and a second jaw at a distal portion of the elongated member wherein at least the first jaw is movable with respect to the second jaw. A jaw clamping mechanism is movable between a first position and second position to move at least the first jaw toward the second jaw to clamp tissue between the first and second jaws. A firing mechanism is movable between a first position and a second firing position to fire fasteners into the tissue clamped between the first and second jaws. An articulation mechanism is movable between a first position and a second position to articulate the jaw assembly from a linear position to a second position angled with respect to a longitudinal axis of the elongated member. A cover on the housing is movable from a closed position to an open position to access the compartment. A power pack is loadable into the compartment, the power pack having a motor and an engagement member engageable with the articulation mechanism to effect movement of the articulation mechanism from the first position to the second position.

In some embodiments, the power pack includes a gear mechanism for moving a drive mechanism linearly to move the articulation mechanism linearly to articulate the jaw assembly. In other embodiments, the power pack includes a drive belt for moving a drive mechanism linearly to move the articulation mechanism linearly to articulate the jaw assembly.

In accordance with another aspect of the present disclosure, a method for powering a surgical stapler is provided comprising the steps of:
providing a surgical stapler having a housing containing a compartment and a cover movable between a closed position and an open position;
loading a power pack having a drive mechanism into the compartment when the cover is in the open position, wherein the step of loading the power pack releasably engages the drive mechanism with a firing mechanism in the housing;
closing the cover to seal the compartment from an external environment;
actuating the motor to move the drive mechanism linearly to thereby move the firing mechanism linearly to advance a plurality of staples into body tissue; and
after advancing the staples, opening the cover and removing the power pack from the compartment to release the engagement of the drive mechanism from the firing mechanism.

In some embodiments, the surgical stapler has first and second jaws movable from an open position to a closed by position by manual movement of a handle.

In some embodiments, the step of loading a power pack into the compartment releasably engages a second drive mechanism of the power pack with an articulation mechanism in the housing.

In accordance with another aspect of the present invention, a power pack is provided removably loadable into a housing of a surgical instrument, the power pack comprising a motor having a motor shaft, a rotatable disc operably connected to the motor shaft, a drive mechanism operably connected to the rotatable disc, and an engagement member linearly movable by the drive mechanism. The engagement member is configured to removably engage an axially movable member in the housing of the surgical instrument, wherein actuation of the motor causes linear movement of the engagement member to effect movement of the axially movable member in an axial direction.

In some embodiments, the rotatable disc is engageable with a drive belt to move the drive mechanism in an axial direction. In some embodiments, the rotatable disc is a gear for moving the drive mechanism axially.

In some embodiments, a second engagement member is provided which is configured to engage a second axially movable member in the housing of the surgical instrument. A second motor and second rotatable disk can be provided for moving the second engagement member axially.

In some embodiments, the first motor is configured to drive a plurality of staples through tissue and the second motor is configured to articulate jaws of the surgical instrument to an angled position with respect to the instrument. In some embodiments, the first motor is configured to move the jaws of the surgical instrument between an open and closed position.

In accordance with another aspect of the present disclosure, a surgical instrument is provided comprising a housing containing a compartment therein, an elongated member extending distally from the housing, and a first jaw and a second jaw at a distal portion of the elongated member, at least the first jaw movable with respect to the second jaw. An advancing mechanism is positioned within the housing and is movable between a first position and a second position. A cover on the housing is openable to access the compartment within the housing. A power pack is loadable into the compartment, the power pack having a motor and an engagement member engageable with the advancing mechanism within the compartment when the power pack is loaded into the compartment to effect movement of the advancing mechanism from the first position to the second position.

In some embodiments, the advancing mechanism is operably connected to at least one of the first and second jaws, wherein movement of the jaw advancing mechanism effects closing of the first and second jaws. In other embodiments, movement of the advancing mechanism effects firing of at least one fastener into the tissue clamped between the first and second jaws.

In some embodiments, the power pack has a second motor and a second engagement member engageable with a second advancing mechanism positioned within the housing of the instrument when the power pack is loaded into the compartment to effect movement of the second advancing mechanism from the first position to the second position.

In accordance with another aspect of the present disclosure, a surgical instrument is provided comprising a housing containing a compartment therein configured to receive a power pack, an elongated member extending distally from the housing and a first jaw and a second jaw at a distal portion of the elongated member, at least the first jaw movable with respect to the second jaw to clamp tissue between the first and second jaws. A firing mechanism is positioned within the housing, the firing mechanism movable between a first position and a second firing position, wherein in the second position, the firing mechanism effects firing of at least one fastener into the tissue clamped between the first and second jaws. A cover is mounted on the housing movable from a closed position to an open position to access the compartment within the housing, the cover in the closed position sealing the compartment from the external environment to protect a power pack when loaded therein. A first seal is provided to prevent flow of body fluids into the compartment from the elongated member to protect the power pack when loaded in the compartment.

In some embodiments, the housing contains a firing rod positioned therein to removably receive an engagement member of the power pack when loaded therein for motorized advancement of the firing rod to effect firing of at least one fastener supported in the instrument.

BRIEF DESCRIPTION OF THE DRAWINGS

So that those having ordinary skill in the art to which the subject invention appertains will more readily understand how to make and use the surgical apparatus disclosed herein, preferred embodiments thereof will be described in detail hereinbelow with reference to the drawings, wherein:

FIG. 3A is a perspective view of the surgical stapler of FIG. 1 showing the handle compartment cover in the open position and further showing the power pack prior to insertion into the handle compartment;

FIG. 3B is front view of the surgical stapler of FIG. 3A showing the handle compartment cover in the open position;

FIG. 3C is a front view of the power pack of FIG. 3A;

FIG. 4A is a top view of the motor and drive mechanism (assembly) of the power pack of FIG. 3A;

FIG. 4B is a side view of the motor and drive mechanism of the power pack of FIG. 4A;

FIG. 4C is a top view of the power pack of FIG. 3A;

FIG. 4D is a side view of the motor and drive mechanism of FIG. 4A shown engaged with the rod of the firing assembly of the surgical stapler of FIG. 1;

FIG. 4E is a perspective view of the motor and drive mechanism of the power pack of FIG. 3A;

FIG. 4F is a cross-sectional view taken along line AY-AY of FIG. 4C showing the power pack engaging the firing rod of the surgical stapler of FIG. 1;

FIG. 4G is a side view of the power pack of FIG. 3A;

FIG. 4H is a cross-sectional view taken along line AT-AT of FIG. 4G;

FIG. 4I is a top view of the surgical stapler of FIG. 1;

FIG. 8A is a top view of the surgical stapler of FIG. 1 showing the power pack fully inserted and the cover of the handle compartment in the closed position, the view the same as FIG. 7A but having section line E-E;

FIG. 8B is a cross-sectional view taken along line E-E of FIG. 8A, the view being the same as FIG. 7B but having section lines F-F and identified area of detail B;

FIG. 8C is a side view of the surgical stapler of FIG. 1 showing the power pack fully inserted in the handle compartment and the compartment cover closed;

FIG. 8D is a cross-sectional view taken along line J-J of FIG. 8C;

FIG. 9 is a cross-sectional view taken along line F-F of FIG. 8B;

FIG. 10 is a close up view of the area of detail G of FIG. 8B;

FIG. 11 is a close up view of the area of detail H of FIG. 9;

FIG. 12 is a close up view of the detail K of FIG. 8D;

FIG. 13A is a side view of an alternate embodiment of the surgical stapler showing the power pack of FIG. 3A prior to insertion into the handle compartment;

FIG. 13B is a side view similar to FIG. 13A showing the power pack of FIG. 3A inserted into the handle compartment;

FIG. 13C is a side view of another alternate embodiment of the surgical stapler showing the power pack of FIG. 3A prior to insertion into the handle compartment;

FIG. 13D is a side view similar to FIG. 13C showing the power pack of FIG. 3A inserted into the handle compartment;

FIG. 14A is a side view illustrating an alternate embodiment having a power pack for effecting both firing and articulation of the surgical stapler, the power pack shown fully inserted into the compartment of the handle of the surgical stapler and the compartment cover shown in the closed position;

FIG. 14B is a top view of the surgical stapler of FIG. 14A;

FIG. 14C is a cross-sectional view taken along line C-C FIG. 14B;

FIG. 14D is a side view of the surgical stapler of FIG. 14A, the view being the same as FIG. 14A but having section line M-M;

FIG. 14E is cross-sectional view taken along line M-M of FIG. 14D;

FIG. 14F is a cross-sectional view taken along line N-N of FIG. 14D;

FIG. 15A is a close up view of the area of detail D of FIG. 14C;

FIG. 15B is a close up view of the area of detail O of FIG. 14E:

FIG. 20 is a cross-sectional side view of the surgical stapler of FIG. 14A, the view being the same as FIG. 14C but having identified areas of detail Q, R and S;

FIG. 21A is an enlarged view of the area of detail Q of FIG. 20;

FIG. 21B is an enlarged view of the area of detail R of FIG. 19A;

FIG. 21C is an enlarged view of the area of detail S of FIG. 19A;

FIG. 22A is a top view of the motor and drive mechanism (assembly) of the power pack of FIG. 14A for effecting staple firing and articulation;

FIG. 22B is a side view of the motor and drive mechanism of the power pack of FIG. 14A;

FIG. 22C is a side view of the motor and drive mechanism of FIG. 14A shown engaged with the articulation rod of the articulation assembly of the surgical stapler of FIG. 14A;

FIG. 22D is a perspective view of the motor and drive mechanism (assembly) of the power pack of FIG. 14A;

FIG. 24A is a top view of the motor and drive mechanism (assembly) of the power pack of an alternate embodiment having a belt drive;

FIG. 24B is a side view of the motor and drive mechanism of FIG. 24A;

FIG. 24C is a perspective view of the motor and drive mechanism of FIG. 24A;

FIG. 24D is a front view of the motor and drive mechanism of FIG. 24A;

FIG. 25A is a top view of the motor and drive mechanism (assembly) of the power pack of an another alternate embodiment having a belt drive;

FIG. 25B is a side view of the motor and drive mechanism of FIG. 25A;

FIG. 25C is a perspective view of the motor and drive mechanism of FIG. 25A;

FIG. 25D is a front view of the motor and drive mechanism of FIG. 25A;

FIG. 26A is a top view of the motor and drive mechanism (assembly) of the power pack of another alternate embodiment having a belt drive;

FIG. 26B is a side view of the motor and drive mechanism of FIG. 26A;

FIG. 26C is a perspective view of the motor and drive mechanism of FIG. 26A;

FIG. 26D is a front view of the motor and drive mechanism of FIG. 26A;

FIG. 27A is a top view of the motor and drive mechanism (assembly) of the power pack of an alternate embodiment having a belt drive;

FIG. 27B is a side view of the motor and drive mechanism of FIG. 27A;

FIG. 27C is a perspective view of the motor and drive mechanism of FIG. 27A;

FIG. 27D is a front view of the motor and drive mechanism of FIG. 27A;

FIG. 27E is a view similar to FIG. 27B showing engagement with the stapler firing rod;

FIG. 28A is a top view of an alternate embodiment of the surgical instrument containing the power pack of FIG. 3A within the handle compartment, the surgical instrument being a circular stapler;

FIG. 28B is a side view of the circular stapler of FIG. 28A;

FIG. 28C is a perspective view of the circular stapler of FIG. 28A;

FIG. 28D is a front view of the circular stapler of FIG. 28A;

FIG. 30A is a top view of an alternate embodiment of the surgical instrument containing the power pack of FIG. 3A within the handle compartment, the surgical instrument being a flexible endoscopic linear stapler;

FIG. 30B is a side view of the linear stapler of FIG. 30A;

FIG. 30C is a perspective view of the linear stapler of FIG. 30A;

FIG. 30D is a front view of the linear stapler of FIG. 30A;

FIG. 31A is a top view of an alternate embodiment of the surgical instrument containing the power pack of FIG. 3A within the handle compartment, the surgical instrument being an endoscopic clip applier;

FIG. 31B is a side view of the clip applier of FIG. 31A;

FIG. 31C is a perspective view of the clip applier of FIG. 31A;

FIG. 31D is a front view of the clip applier of FIG. 31A;

FIG. 32A is a top view of an alternate embodiment of the surgical instrument containing the power pack of FIG. 3A within the handle compartment, the surgical instrument being an endoscopic grasper;

FIG. 32B is a side view of the endoscopic grasper of FIG. 32A;

FIG. 32C is a perspective view of the endoscopic grasper of FIG. 32A;

FIG. 32D is a front view of the endoscopic grasper of FIG. 32A;

FIG. 33A is a top view of an alternate embodiment of the surgical instrument containing the power pack of FIG. 3A within the handle compartment, the surgical instrument being an endoscopic scissor;

FIG. 33B is a side view of the endoscopic scissor of FIG. 33A;

FIG. 33C is a perspective view of the endoscopic scissor of FIG. 33A; and

FIG. 33D is a front view of the endoscopic scissor of FIG. 33A.

FIG. 34A is a top view of an alternate embodiment of the surgical instrument containing the power pack of FIG. 3A within the handle compartment, the surgical instrument being a fastener applier;

FIG. 34B is a side view of the fastener applier of FIG. 34A;

FIG. 34C is a perspective view of the fastener applier of FIG. 34A; and

FIG. 34D is a front view of the fastener applier of FIG. 34A.

DETAILED DESCRIPTION OF PREFERRED EMBODIMENTS

Figure 1:
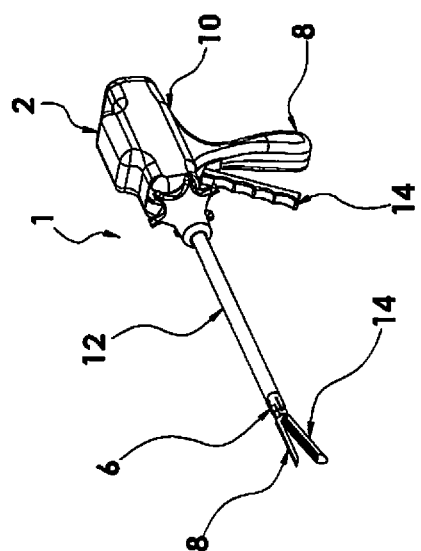
FIG. 1 is a perspective view of a first embodiment of the surgical stapler of the present disclosure having a removable power pack.
Figure 2A:
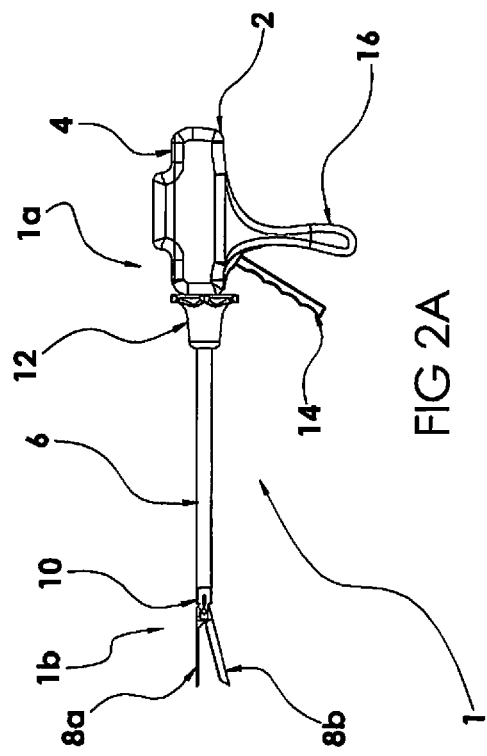
FIG. 2A is a side view of the surgical stapler of FIG. 1.
Figure 2B:
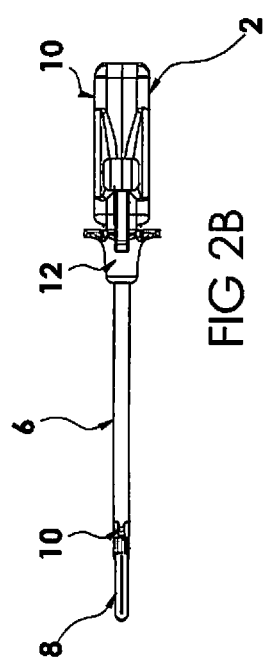
FIG. 2B is a bottom view of the surgical stapler of FIG. 1.
Figure 2C:
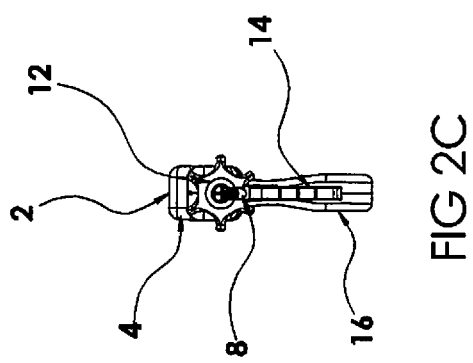
FIG. 2C is a front view of the surgical stapler of FIG. 1A.

The present disclosure provides power packs, containing a battery and power train, which are loadable into a surgical stapler to power various functions of the surgical stapler to reduce the forces exerted by the clinician otherwise required if manual force was utilized. The present disclosure also provides surgical staplers designed to receive the power pack and to interact with the power pack to effect firing of the staplers. In some instances, the power pack can be used to effect articulation of the jaw assembly of the stapler to pivot the jaw assembly with respect to the longitudinal axis of the stapler. Each of these embodiments is discussed in detail below.

The power pack can also be utilized for powering endoscopic linear staplers, other types of staplers as well as other surgical instruments. Examples of these instruments are also discussed below.

The loadable power packs of the present disclosure are mountable into the handle housing of the surgical instrument, and are maintained in a sterile environment within the surgical instrument so they can be removed and reused. This enables the power pack to be removed from the stapler and reused in another procedure and/or instrument without the complexities, time, costs and risks of resterilization of the power pack. The sealed environment of the battery and power train within the housing also enables certain features/components to be used which might not otherwise be practical if sterilization of the internal power pack was required. Thus, by preventing contact between the power pack and the patient and/or bodily fluids and the external environment, resterilization is not required. The power pack can be used with surgical instruments discarded after use (fully disposable instruments), partially disposable surgical instruments or with fully reusable/sterilizable instruments with the advantage that the power pack need not be discarded or sterilized. Thus, the surgical stapler of the present disclosure advantageously reduces the time, resources and/or costs for preparing the surgical stapler for its next use. The power packs are easily loadable in the surgical instrument, preferably the handle assembly or housing of the instrument, to easily and securely engage structure in the housing to effect movement of such structure in the instrument. The power packs are also easily disengageable from the structure for removal from the housing for subsequent reuse. The power packs can be configured so they can be loadable and engageable in various types of surgical instruments. The power pack is fully enclosed and sealed by the handle housing so there is no need to sterilize the power pack between uses.

Referring now to the drawings and particular embodiments of the present disclosure, wherein like reference numerals identify similar structural features of the devices disclosed herein, there are illustrated several embodiments of the surgical instruments and removable power pack of the present disclosure.

With reference to FIGS. 1-23B, the power pack is used with endoscopic linear staplers which are inserted through trocars and fire linear rows of surgical staples from a cartridge through tissue into contact with an anvil which forms the individual staples. The staplers include an openable compartment in the handle housing that enables easy loading of the power pack within the stapler. The staplers also provide a tight seal to protect the power pack from contaminants so that the power pack does not need to be sterilized for multiple uses.

The power pack is engageable with a staple drive (staple firing) mechanism of the surgical stapler so that once it is loaded in the stapler, actuation of the motor within the power pack effects firing of the staples through tissue. In some embodiments, the power pack is engageable with an articulation mechanism wherein actuation of the motor effects articulation of the stapler. The powered articulation can be in addition to the powered staple firing or alternatively the stapler could have powered articulation and manual staple firing. A specific embodiment of such powered articulation included with powered firing is shown in FIGS. 14A-23B and discussed in detail below.

The term "surgical fasteners" as used herein encompasses staples having legs which are deformed by an anvil, two part fasteners wherein a fastener or staple component with legs is received and retained in a second component (retainer), and other types of fasteners which are advanced through tissue of a patient in performing surgical procedures.

The term "proximal" as used herein denotes the region closer to the user and the term "distal" as used herein denotes the region further from the user. The terms "top" or "upper" and "bottom" or "lower" refer to the orientation of the instruments as shown in the orientation of the instrument in FIG. 2A, with the cover being on the top and the handle extending at the bottom.

Turning first to FIGS. 1-12, a first embodiment of the surgical stapler and removable power pack are illustrated. In this embodiment, the power pack, which contains a battery, motor, drive mechanism and stapler engagement structure, effects firing of the surgical fasteners (staples).

Figure 7A:
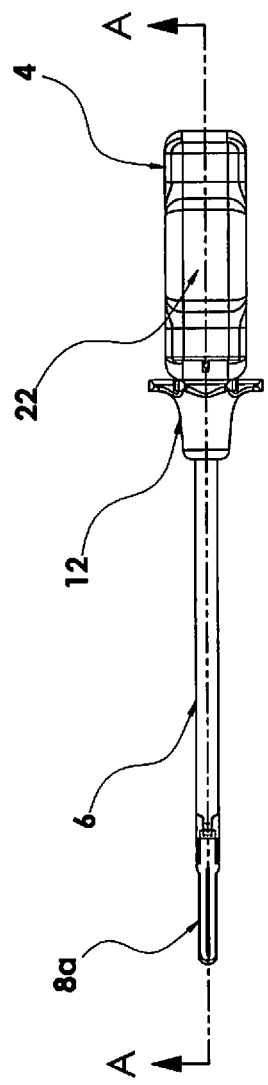
FIG. 7A is a top view of the surgical stapler of FIG. 1 with the power pack fully inserted into the compartment in the handle and the cover in the closed position.
Figure 7C:
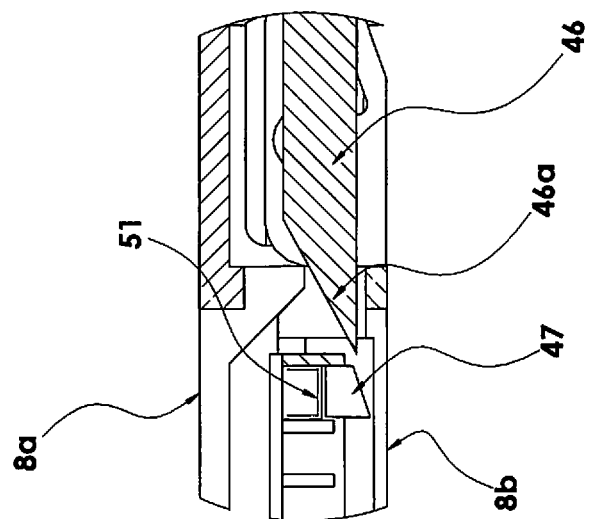
FIG. 7C is a close up view of the area of detail B of FIG. 7B showing the firing mechanism at the distal end for firing staples.
Figure 7B:
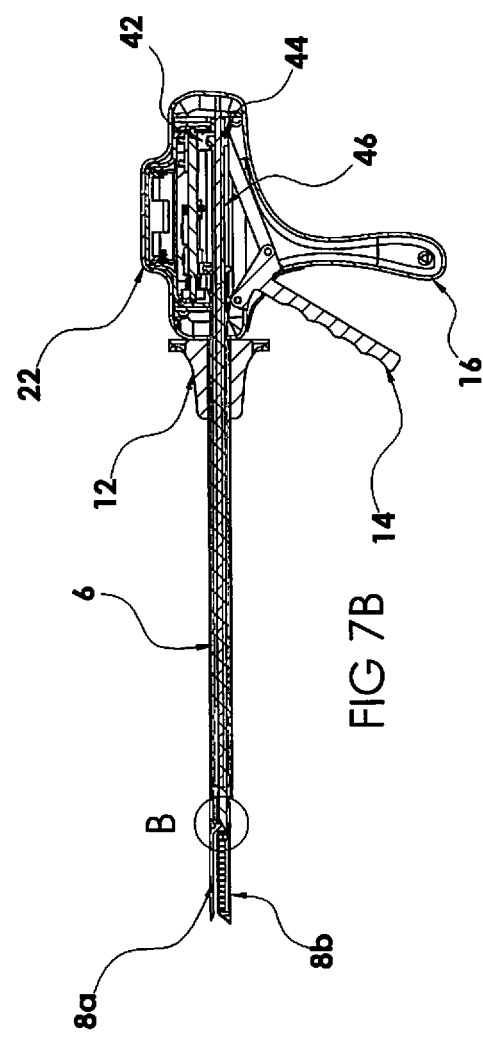
FIG. 7B is a cross-sectional view taken along line A-A of FIG. 7A.

The surgical stapler, also referred to herein as the or surgical fastener applying instrument or surgical fastener applier, is designated generally by reference numeral 1 and includes a proximal portion 1a, a distal portion 1b and an elongated or endoscopic portion 6 (also referred to as an elongated tubular portion or shaft) extending between the proximal portion 1a and the distal portion 1b. A handle assembly 2 with a housing 4 (also referred to herein as a handle housing) is positioned at the proximal portion 1a and is configured to house and protect internal mechanisms of the stapler including the removable power pack when loaded (mounted) therein. At the distal portion 1b are opposing members, i.e., jaws, 8a, 8b, configured to clamp and constrain tissue during operation of the surgical stapler. At least one of the jaws is movable with respect to the other jaw from an open position to receive tissue between the jaws and a closed position to clamp tissue between the jaws. Thus, one of the jaws can be stationary and the other jaw movable with respect to the stationary jaw or alternatively both jaws can move, e.g., pivot, toward each other. In the embodiment of FIG. 1, jaw 8b, which contains at least one row of surgical fasteners (staples) is movable with respect to non-pivoting (stationary) jaw 8a which contains an anvil with staple forming pockets. Jaws 8a, 8b are collectively referred to herein as jaws 8. The fasteners are fired (advanced) from jaw 8b by linear movement of a firing mechanism which engages staple drivers within the jaw 8b which move transverse to the longitudinal axis, i.e., transverse to the direction of movement of the firing mechanism, to sequentially advance (from proximal to distal) the staples in the linear rows of staples from the jaw 8b and through tissue to engage the anvil pockets on jaws 8a for formation of the staples. Such firing of the staples is illustrated in FIG. 7C and discussed below.

The elongated tubular member 6 extends distally from the housing 4 and is configured to fit through a surgical port (trocar) used for laparoscopic surgery. The endoscopic portion 6 can be of varying dimensions and in some embodiments is configured to fit through a 10 mm trocar, although other dimensions for fitting through other size trocars are also contemplated such as trocars ranging from 5 mm to 15 mm. It is advantageous to minimize the diameter of the endoscopic portion to minimize the size of the patient's incision. With the jaws 8 in the clamped position, the outer diameter of the elongated member 6 is maintained as the cross-sectional dimension of the closed jaws 8 preferably does not exceed the cross-sectional dimension (i.e., diameter) of the tubular member 6.

The surgical stapler 1 can in some embodiments include a joint 10 that provides for the articulation of the opposing members 8, i.e., pivoting of the jaw assembly (jaws 8) to angular positions with respect to the longitudinal axis of elongated member 6. Articulation can be achieved by linear motion of elongated members extending through the endoscopic portion 6 which are slidable to angle the jaw assembly. A rotational member or knob 12 is configured to rotate, with respect to the handle assembly, the elongated member 6 and connected jaws 8 about the axis of the elongated member 6 to change the position of the jaws 8. Articulation is effected by manual manipulation of a lever adjacent the handle 2. A handle lever 14, linked to an axially movable clamping bar, is pivotable from a first position to a second position closer to stationary handle 16 to effect movement of the jaw 8b toward the jaw 8a from an open (unclamped) position to a clamping position, also referred to as a closed position of the jaws 8. Release of handle lever 14 returns the jaw 8b to its open position. Stationary handle 16 for grasping by the user is ergonomically designed for comfort of use. In summary, the surgical stapler operates by manual pivoting of the lever 14 toward stationary handle 16 to clamp the tissue between jaws 8, followed by powered firing of the staples from jaw 8b, through the clamped tissue and into contact with the staple forming pockets of the anvil of jaw 8b. Prior to firing, the jaws 8 can be rotated to a desired orientation by rotation of endoscopic portion 6 via knob 12 and/or articulated about joint 10, via movement of the elongated articulation members, to a desired angled position with respect to the longitudinal axis of endoscopic portion 6. In the embodiment of FIG. 1, articulation is performed by manual manipulation of a lever (not shown) which is operatively connected to an internal elongated member within tubular member 6 which extends to joint 10. A force applied to the internal elongated member pivots/articulates the jaws 8 about the joint 10. In later described embodiments (FIG. 14A), powered articulation is provided.

Figure 3D:
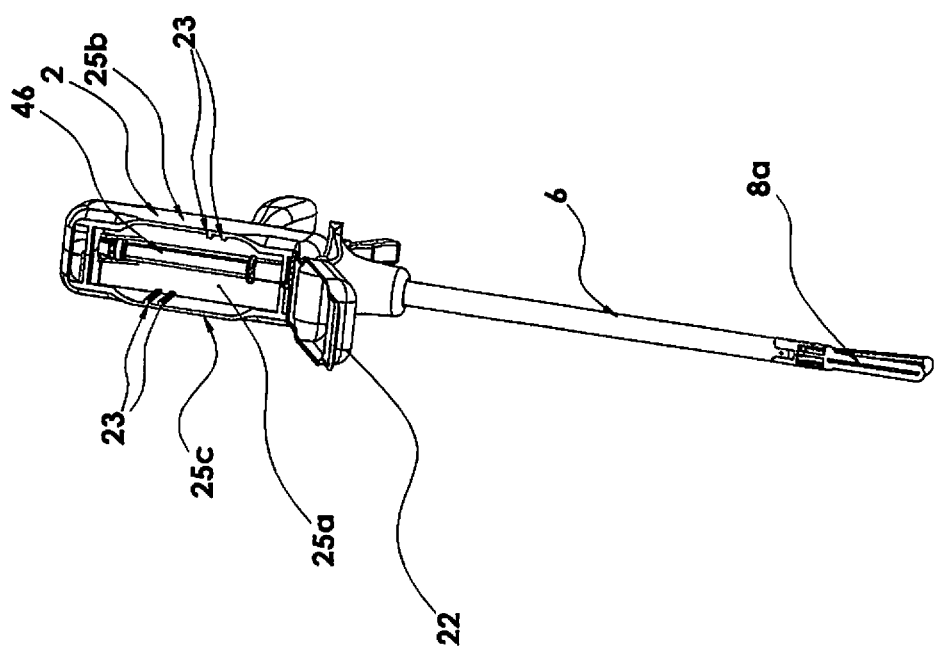
FIG. 3D is a top perspective view of the surgical staple of FIG. 3A showing the compartment for receiving the power pack.

The housing 4 of the handle assembly 2 of the surgical stapler is configured to receive the loadable/removable power pack 18 in a receptacle (compartment) 20 as shown in FIGS. 3A and 3D. The receptacle includes a base 25a and side walls 25b and 25c having one or more guides 23 that cooperate with corresponding guiding structures 28 on the outer wall of the housing 19 of power pack 18 for proper alignment of the power pack 18 in the handle assembly 2 during insertion into the receptacle 20. In the embodiment of FIG. 3A, the guides 28 on power pack housing 19 are in the form of a pair of ribs or projections 28 extending transversely to a longitudinal axis of the power pack 18 for receipt within grooves formed between guides, e.g., ribs or projections, 23 of the compartment 20, also extending transversely with respect to a longitudinal axis of the stapler 1. In the illustrated embodiment, the ribs 23 are on opposing sides of the power pack 18 and are axially offset from each other, although in alternate embodiments they can be axially aligned. Additionally, a different number of ribs (axially or non-axially aligned) can be provided (with corresponding receiving structure in the compartment 20). It should be appreciated that alternatively, the grooves could be provided on the power pack 18 and the ribs provided in the compartment 20 to provide the guiding structure for the power pack 18. The guiding structure also helps to retain power pack 18 in position within the compartment 20. The power pack 18 has front and rear concave regions 19a, 19b to reduce its overall size.

The handle assembly 2 includes a cover 22 for opening and closing the receptacle 20. The compartment cover 22 is shown as being hingedly attached to the housing 4, but may alternatively be fully removable or attached in some other manner such as a slidable connection or the like. The cover 22 is shown pivotable mounted to a top portion of the housing 4 (in the orientation of FIG. 2A) for top loading of the power pack, although alternatively, side or bottom loading can be provided. The cover 22 is shown pivotable from a closed position of FIG. 2A to an open position of FIG. 3A to enable loading of power pack into the compartment 20 of the housing 4. In some embodiments, the cover 20 is spring loaded to an open position so it remains open for loading of the power pack 18. Once loaded, the cover 22 is pivoted about hinge 22a to its closed position. A latch can be provided to latch the cover 22 to the housing 4 in the closed position. When the cover 22 is in an open position, e.g., as shown in FIG. 3A, the power pack 18 may be removed from the receptacle 20 or inserted into the receptacle 20.

When the cover 22 is in a closed position, the seal of the cover 22 is in contact with the rim of the housing 2 such that the receptacle 20, and the power pack 18 if inserted into the receptacle 20, is sealed from the environment exterior to the surgical stapler. The top seal 24 can be attached to the cover 22 and in some embodiments can be in the form of an elastomer that is compressed by the housing, e.g., tightly fits slightly within the housing or is pressed on the rim of the housing 2. In other embodiments, the elastomer seal 24 can be on the housing 2, i.e., extending around the perimeter of the rim of the compartment 20, and is compressed by the cover 22 to seal between the cover 22 and housing 4. Other seals can also be provided within the surgical stapler to seal/protect the power pack 18 from contaminants, e.g., body fluids. These seals are discussed in more detail below.

Turning now to the power pack of the present disclosure, and with reference to FIGS. 4A-4I, the power pack 18 includes a motor assembly, battery and electronics contained within housing 19. More specifically, as shown in FIGS. 4A-4E, the power pack 18 includes a powering assembly including a motor 32 connected to a planetary gear box 34 configured to gear down the output of the motor 32 for proper drive speeds for firing staples from jaw 8b through the tissue into contact with the anvil of jaw 8a. The planetary gear box 34 drives a lead screw 36 through one or more gears operatively connected to the motor shaft. More specifically, upon rotation of the motor shaft by motor 32 in a first direction, gear 38 is rotated in the same first direction, causing rotation of the gear 30 in a second opposite direction due to the intermeshed teeth of gears 30 and 38. Lead screw 36 is operatively connected to gear 30 so that rotation of gear 30 causes rotation of lead screw 30 in the same direction. The power pack 18 includes a battery 33 which can be rechargeable outside the stapler when the power pack 18 is removed. The power pack 18 in some embodiments can include a power switch which is activated, i.e., turned on, by the clinician to start the motor and effect staple firing. In other embodiments, the motor can automatically turn on when the power pack is fully loaded or upon actuation of another control on the stapler housing 4. In some embodiments, the motor can automatically turn off when the power pack is removed from the stapler housing.

Connected to the end of lead screw 36 (the end opposite the connection to the gear 30) is a drive mechanism 40. The drive mechanism 40 is configured to move in a linear motion (in an axial direction) along the lead screw 36 in response to rotation of the lead screw 36. For example, the drive mechanism 40 may include internal threads that engage external threads of the lead screw 36 and may include slides engaged in a track that prevent the drive mechanism 40 from rotating and therefore cause the drive mechanism 40 to move linearly (axially) in response to rotation of the lead screw 36. As depicted in FIGS. 4A-4G, the power pack 18 has a compact configuration as the lead screw 36 extends alongside, slightly spaced from, the motor 32 and gear box 34, i.e., both the motor 32/gear box 34 and lead screw 36 extending longitudinally with the lead screw 36 parallel to the motor 32. The drive mechanism 40 is connected to a proximal end of lead screw 36 and extends proximally of the proximal end of the motor 32 in the illustrated embodiment.

The power pack 18 can have features/structure to constrain the motor 32. In the embodiment of FIG. 4F, such feature is in the form of proximal rails 27a and distal rails 27b spaced apart axially within the housing 19. Motor 32 is seated within proximal rails 27a and gear box 34 is seated within rails 27b, the rails 27a, 27b retaining the motor and preventing axial and rotational movement within the housing 19. Bearing or bushings 27c and 27d can also be provided to constrain the lead screw 36 at opposing ends, while allowing rotation thereof, thereby also constraining the motor. Other features can additionally or alternatively be provided to restrain the motor from axial movement while allowing rotation of the lead screw.

The drive mechanism 40 includes a first output flag or yoke 42, which is discussed in more detail below, configured to engage a staple firing mechanism, e.g., firing rod 46, extending longitudinally within the handle 4. The staple firing rod 46 is operatively connected to a firing rod in the endoscopic portion 6 which is operatively engageable with a series of staple drivers in jaw 8b to advance the fasteners (staples) from the fastener jaw 8b. Alternatively, the firing rod 46 can extend through the endoscopic portion 6 and itself engage the stapler drivers as shown in FIG. 7C. Thus, as the motor 32 generates rotational motion of the lead screw 36 through the planetary gear box 34 and the gears 38, 30, the drive mechanism 40 moves in linear motion along the lead screw 36. Such linear motion effects linear movement of the firing rod 46 (due to the engagement by the flag 42) which advances the staple driving mechanism to advance (fire) the staples out from jaw 8b through tissue and into contact with the anvil in jaw 8a. As noted above, the firing rod 46 can be a single element extending through the endoscopic portion 6 (see e.g., FIG. 7C) and terminating adjacent jaws 8 or alternatively can be attached to one or more components intermediate the firing rod 46 and jaws 8. In FIG. 7C, camming surface 46a of firing rod 46 engages staple drivers 47 to sequentially fire staples 51 as the firing rod 46 is advanced.

The power pack 18 can also include in some embodiments one or more sensors to indicate the position of the firing rod 46 to indicate to the clinician the status of staple firing. The embodiment of FIG. 4F illustrates an example of such sensors if they are provided. The power pack 18 has within the housing a proximal sensor 39a and a distal sensor 39b to sense the position of yoke 42 of the drive mechanism 40. Thus, sensor 39a senses the initial position of the yoke 42 (and thus the initial position of the firing rod 46) and at the end of the firing stroke, sensor 39b would indicate the end (final) position of the yoke 42 (and thus the final positon of the firing rod 46) which would indicate completed firing of the fasteners. The power pack 18 could also include an audible or visual indicator (viewable though the power pack housing 19 and instrument handle housing 4) actuated by the sensor to indicate to the clinician the position of the flag 42 and thus the completion or status of the firing stroke to fire the fasteners. The power pack 19 can also include sensors to detect the position of the articulation flag in the embodiments discussed below which have powered articulation. The sensor can include a potentiometer to determine the location during the firing stroke. It can also include an encoder to detect the position along the stroke. Alternatively, the stroke can also be identified by motor count. The power pack 18 in all other respects is identical to power pack 18 of FIG. 3A.

It is also contemplated that in alternate embodiments, the sensor(s) can be carried by the handle housing rather than (or in addition to) the power pack and utilized to detect the positioning of the flag 42 and/or firing rod 46 and/or detect the position of the articulation flag and/or articulation rod in the embodiments discussed below which have powered articulation.

It is also contemplated that a sensor(s) can be provided to detect the position of the clamping rod for clamping the jaws. The sensor can be provided in (or supported by) the power pack or alternatively the sensor(s) can be carried by the handle housing rather than (or in addition to) the power pack and utilized to detect the positioning of the jaws by detecting the position of the flag engaging the jaw clamping rod and/or detecting the position of the jaw clamping rod in the embodiments which have powered clamping.

Note the sensor can be provided in some embodiments; in other embodiments, no sensor is provided.

Figure 6D:
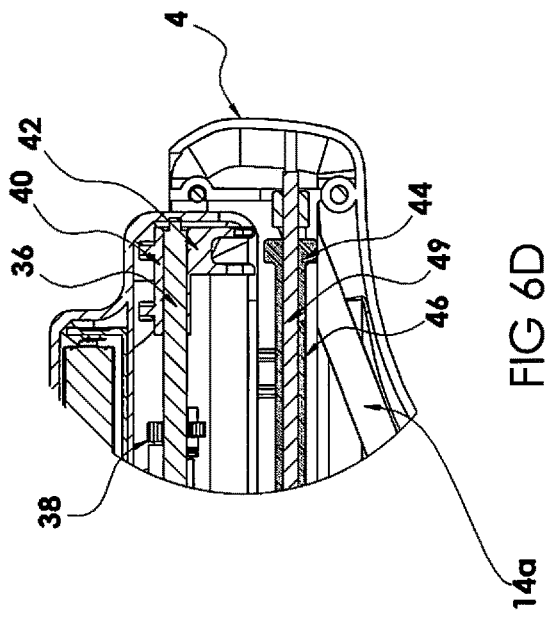
FIG. 6D is a close up view of the area of detail AR of FIG. 6C.
Figure 6A:
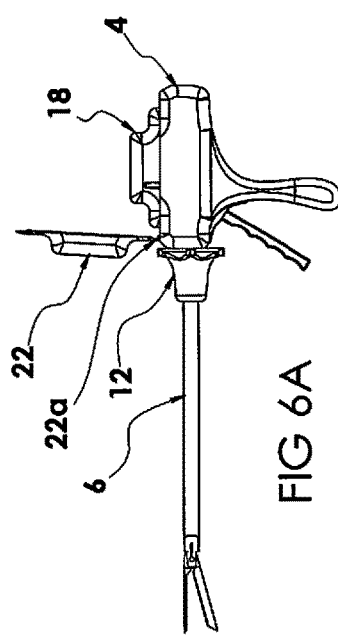
FIG. 6A is a side view of the surgical stapler of FIG. 1 showing the handle compartment cover in the open position and further showing the power pack in the process of being inserted in the compartment of the handle.
Figure 6B:
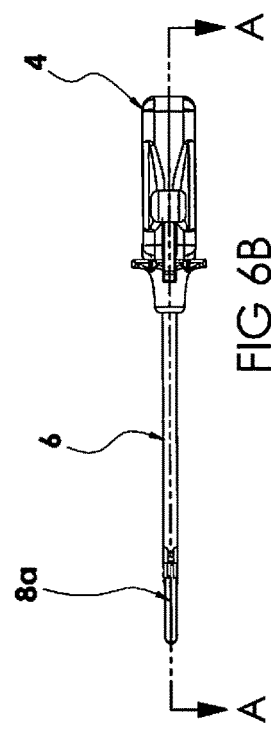
FIG. 6B is a bottom view of the surgical stapler of FIG. 6A.
Figure 6C:
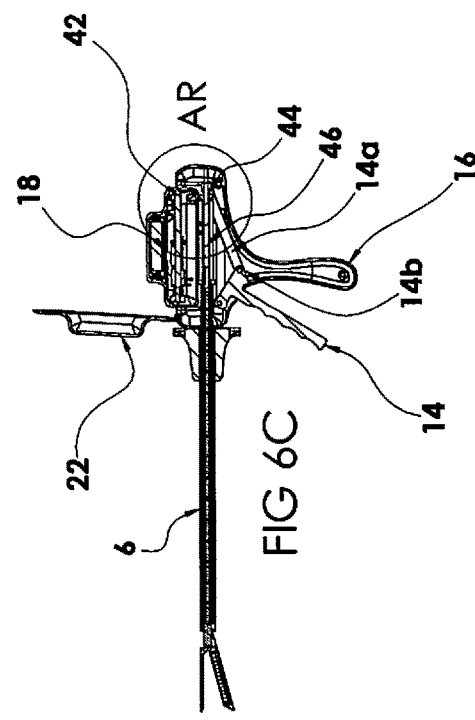
FIG. 6C is a cross-sectional view taken along line A-A of FIG. 6B.

Turning now to the loading of the power pack 18 into the surgical stapler 1, as seen in FIGS. 6A-6D, the power pack 18 is in the process of being inserted into the receptacle 20 of housing 4. As shown, handle compartment cover 22 is open to provide access to compartment 20. The output flag 42 of the power pack 18 as noted above is driven by the motor assembly and is configured to engage and interact with structure within the handle assembly 2, e.g., firing rod 46, to control operation of the surgical stapler 1 when the power pack 18 is fully inserted into the receptacle 20. As can be appreciated in FIG. 6D, the output flag 42 is not fully engaged with the flange 44 of the firing rod 46. Also shown in FIG. 6D is the clamp bar 49 which is positioned within and concentric with firing rod 46. The clamp bar 49 is operatively connected to the pivotable handle 14 of stapler 1 via linkage 14a (pin 14b connects one end of handle 14 to the distal end of clamp bar 49). In this manner, movement of pivotable handle 14 toward stationary handle 16 causes the operatively connected jaw clamping mechanism, e.g., clamp rod 49, to be advanced distally to pivot jaw 8*b* toward jaw 8*a* to clamp tissue between the two jaws 8. Note that for clamping, clamp bar 49 slides linearly within a lumen of firing rod 46; for staple firing, firing rod 46 moves linearly over clamp bar 49.

The output flag 42 of power pack 18 is configured to engage a bossed end 44 of the firing rod 46 when the power pack 18 is fully inserted into the receptacle 20 of the handle assembly 2. As shown, the output flag (yoke) 42 has a receiving or mounting feature or member (also referred to as the engagement feature (member) or firing rod engagement feature (member) in the form of two arms 43*a* and a slot 43*b* therebetween, configured to frictionally (and releasably) engage the bossed end 44, the feature aligning with the bossed end 44 during insertion. (The aforedescribed guiding structure on the power pack 18 and internal wall of the compartment 20 aid such alignment).

FIGS. 8A, 8B and 10 show the power pack 18 fully inserted into the compartment 20 of stapler 1. In this position, the output flag 42 is engaged with the bossed end 44 of the firing rod 46. Note the firing rod 46 is able to rotate when the first output flag 42 of the power pack 18 is engaged with the bossed end 44. When the power pack 18 is secured to the firing rod 46 by the first output flag 42, linear motion generated at the first output flag 42 by the motor actuated drive assembly is transferred to the firing rod 46, which moves linearly to actuate the staple firing mechanism. That is, rotation of the gear 30 effects axial (linear) movement of the drive screw 36 which effects axial (linear) movement of the connected drive mechanism 40 to effect axial (linear) movement of the associated drive mechanism (rod) engaging member (i.e., flag 42). It should be appreciated that flag 42 provides one example of the releasable attachment (engagement member) of the motor assembly to the firing rod 46, it being understood that other mounting (engagement) members or features are also contemplated to engage the firing rod to advance it axially. In use, the cover 22 of stapler 1 is opened and the power pack 18 is inserted into receptacle 20 of sterile handle assembly 2 (of sterile stapler 1), with the output flag 42 of the power pack 18 engaging a corresponding feature, e.g., boss 44 of elongated drive rod 46, in the handle assembly 2 as discussed above. Then, the cover 22 is closed to seal the power pack 18 within the receptacle 20 from the external environment and the surgical stapler 1 may be actuated, i.e., manually clamped, articulated and/or rotated if desired, and the motor actuated to effect staple firing. After applications of fasteners and release (unclamping of the jaws from tissue), the cover 22 can be opened and the power pack 18 removed and charged while the stapler and handle assembly are resterilized if the stapler is a reusable instrument or the stapler and handle assembly are disposed of if the stapler is a single use disposable instrument. The power pack 18, due to its sealed configuration discussed above, can be reused without requiring sterilization by insertion into the receptacle 20 of a resterilized handle assembly or a sterile handle assembly of an unused disposable handle assembly. Thus, as can be appreciated, the removable power pack 18 does not need to be subjected to the sterilization process and, therefore, contact between the harsh temperatures and/or chemicals of the sterilization process is advantageously avoided. Also, by being able to reuse the power pack without sterilization, significant cost savings are achieved compared to if the power pack is not resterilizable, is disposed of along with the disposable stapler.

Note that in the embodiment of FIGS. 1-12 (and FIGS. 14-23B discussed below), rotational motion caused by the motor is translated into linear motion. This is shown schematically in FIG. 5A wherein the drive rod in the handle housing is engaged by the motor driven drive assembly of the power pack 18 (or power pack 90 which is discussed below) moves linearly (axially) to effect linear (axial) movement of the drive member in the stapler, e.g., extending through the endoscopic portion, which effects staple firing. Alternatively, or in addition, a drive assembly of the power pack engages a drive rod in the housing which moves linearly to effect linear movement of a drive rod to effect clamping of the jaws and/or a drive assembly of the power pack engages a drive rod in the housing which moves linearly to effect linear movement of a drive member to effect articulation of the jaw assembly. Alternatively, the intermediate drive member could be omitted and the drive rods directly effect respective clamping and articulation.

Figure 5A:
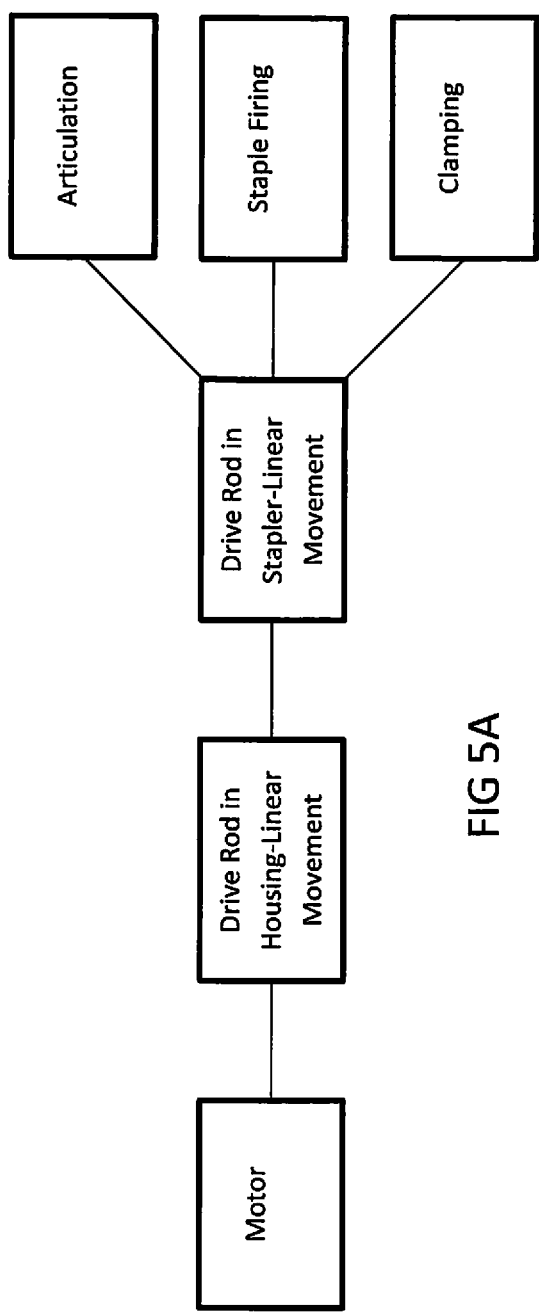
FIG. 5A is a schematic view illustrating transition from rotational movement to linear movement to effect a function of the surgical stapler.
Figure 5B:
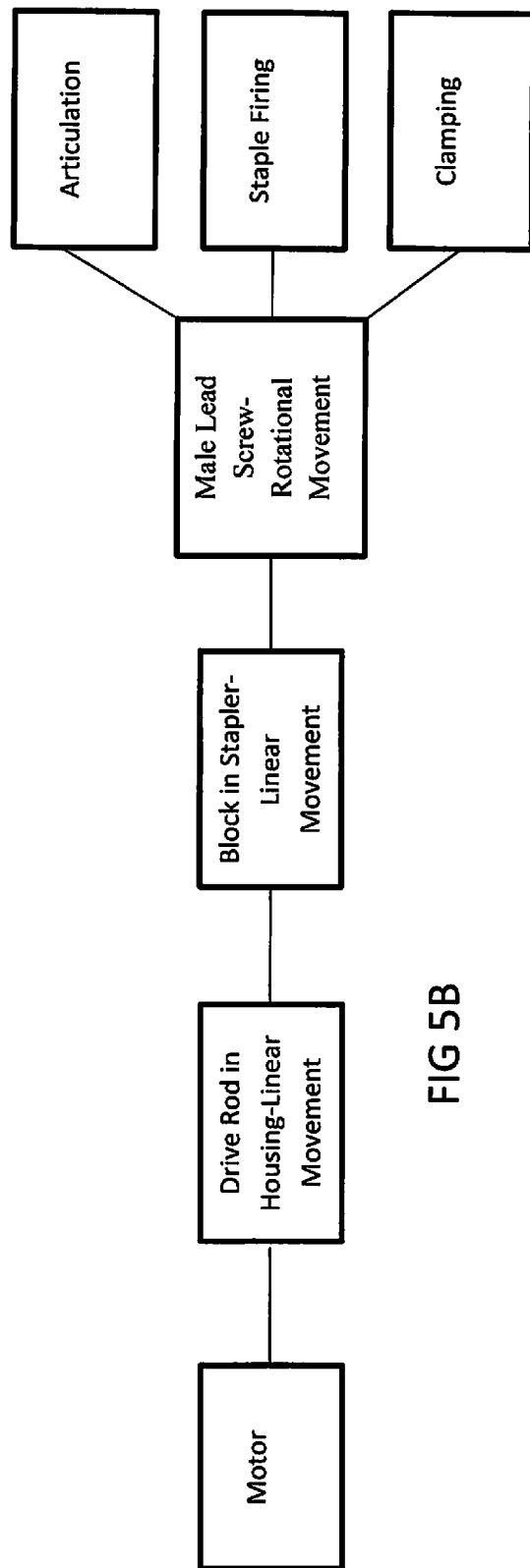
FIG. 5B is a schematic view of an alternate embodiment illustrating transition from rotational movement to linear movement to rotational movement to effect a function of the surgical stapler.

In an alternate embodiment, shown schematically in FIG. 5B, linear motion is converted back to rotational movement. That is, the handle housing has a receptacle (compartment) to receive power pack 18 (or power pack 90) which has one or more engagement features to engage or couple to a firing rod for firing staples, a clamping rod for clamping the jaws about tissue and/or an articulation rod to articulate the jaws to angular positions with respect to the longitudinal axis. The drive rod is connected at its distal end to a block in the stapler having a female thread or a slotted guide engagement to prevent rotation of the block and enable linear movement. (The drive rod could alternatively be attached to other structure). The block is connected to a male lead screw which is engaged at its proximal end via threaded engagement to the distal end of the block. The lead screw is connected at its distal end to a component that requires rotation to effect operation of the stapler, such as effecting staple firing, clamping and/or articulation. A bearing can be provided to keep the lead screw on center and control axial motion. In use, actuation of the motor advances the drive assembly of the power pack linearly which is engaged with and advances the drive rod in the handle housing linearly (axially). Linear movement of the drive rod causes linear movement of the block positioned in the endoscopic portion (or alternatively positioned in the handle housing.) Linear movement of the block causes rotation of the male lead screw to engage a staple firing component(s) to effect staple firing. Alternatively, or in addition, the drive assembly, or a separate drive assembly (assemblies), engages a drive rod in the housing which moves linearly to effect linear movement of a block to cause rotation of the lead screw to move a jaw clamping component(s) to effect clamping of the jaws and/or engages a drive rod in the housing which moves linearly to effect linear movement of a block to cause rotation of the lead screw to move an articulation component(s) to effect articulation of the jaws.

In the embodiment of FIGS. 1-12, the power pack 18 actuates the firing rod 46 to fire the staples while other steps are performed manually. In summary, in this embodiment, in use, the jaws 8*a*, 8*b* are moved to the closed (clamped) position manually by a hand actuated lever or control. Also, in this embodiment, the jaws 8 are articulated with respect to the longitudinal axis of the endoscopic portion manually by a hand actuated lever or control. Thus, the clinician would manually clamp the jaws, manually rotate the endoscopic portion and attached jaws 8, and manually articulate the jaws by manipulation of controls at the proximal end of the stapler 1, e.g., at the handle 4.

FIGS. 1-12 show one embodiment of an endoscopic linear stapler that can be used with the power pack 19 of the present disclosure. However, the power pack 18 is not limited to such endoscopic staplers. For example, FIGS. 13A and 13B illustrate another endoscopic linear stapler, designated by reference numeral 100, that can be powered by power pack 18. Stapler 100 has a handle 102 manually pivotable towards stationary handle 103 for clamping of the jaws 108a, 108b, an endoscopic portion 106 extending from the handle housing 101, a jaw assembly 104 containing jaws 108a, 108b and connector 107a extending proximally from shaft or tube 107 for attachment to the endoscopic portion 106 so that the jaw assembly 104 can be replaced multiple times in a single surgical procedure to provide additional rows of staples to tissue. The stapler 100 also includes a rotation knob 109 for rotation of the endoscopic portion 106, with respect to the handle housing, to rotate the attached jaws 108a, 108b. The stapler 100 can also include an articulation knob to articulate the jaws. Power pack 18 is shown in FIG. 13A prior to loading within the handle housing 101 and shown in FIG. 13B fully loaded (inserted) within the handle housing 101. A cover (not shown) can be provided to seal the power pack 18 from the external environment. As in the embodiment of FIGS. 1-12, the flag 42 extending from lead screw 36 engages a firing rod within the handle housing 101 to effect movement of a firing rod to fire the staples when the motor of the power pack 18 is actuated. Power pack 90 having articulation described below can also be utilized with stapler 100.

FIGS. 13C and 13D illustrate another endoscopic linear stapler that can receive the power pack 18. Endoscopic linear stapler 110 has a handle 112 manually pivotable toward stationary handle 113 for clamping of the jaws 118a, 118b, an endoscopic portion 116 extending from the handle housing 111, and a jaw assembly at the distal end of the endoscopic portion 116. The stapler 110 also includes a rotation knob 119 for rotation of the endoscopic portion 116 to rotate the jaws 118a, 118b. The stapler 110 can also include an articulation knob to articulate the jaws 118a, 118b. Power pack 18 is shown in FIG. 13C prior to loading within the handle housing 112 and shown in FIG. 13D fully loaded (inserted) within the handle housing 112. A cover (not shown) can be provided to seal the power pack 18 from the external environment. As in the embodiment of FIGS. 1-12, the flag 42 extending from lead screw 36 engages a firing rod within the handle housing 111 to effect movement of a firing rod to fire the staples when the motor of the power pack 18 is actuated. Power pack 90 having articulation described below can also be utilized with stapler 110.

FIGS. 30A-30D illustrate another type of endoscopic linear stapler that can receive and be powered by the power pack 18. Stapler 260 has a handle 266 manually pivotable towards stationary handle 264 for clamping of the jaws, an endoscopic portion 268 extending from the handle housing 267, and a jaw assembly containing jaws 272a, 272b. The endoscopic portion 268 is flexible which enables use in various endoscopic procedures. The stapler 260 also includes a rotation knob 270 for rotation of the endoscopic portion 268 to rotate the jaws 272a, 272b. Power pack 18 is shown fully loaded (inserted) within the handle housing 262 and cover 263 closed to seal the power pack 18 from the external environment. As in the embodiment of FIGS. 1-12, the flag 42 extending from lead screw 36 engages a firing rod within the handle housing 262 to effect movement of a flexible firing rod extending through flexible endoscopic portion 268 to fire the staples when the motor of the power pack 18 is actuated. Power pack 90 having articulation described below can also be utilized with stapler 260.

The power pack 18 is also not limited to use with endoscopic linear staplers, nor is it limited to use with staplers. FIGS. 28A-29D illustrate two examples of different staplers. As in the endoscopic linear staplers discussed herein, these staplers can also have a knife bar to cut tissue between the rows of staples applied to the tissue.

By way of example, the power pack 18 can be used with a circular stapler that applies circular arrays of staples such as shown in FIGS. 28A-28D. Surgical stapling instrument 220 can receive and be powered by the power pack 18 of the present disclosure. Stapler 220 has a handle 226 manually pivotable towards stationary handle 264 for clamping of the jaws, an elongated tubular portion 228 extending from the handle housing 222, and a jaw assembly having an anvil (jaw) 232 and a cartridge (jaw) 235 containing circular arrays of fasteners (staples). The anvil 232 has a proximal clamping surface 233 and is movable by anvil rod 234 toward the cartridge 235 to clamp tissue between the anvil clamping surface 233 and distal clamping surface 236 of cartridge 235 by manual movement of handle 226 toward stationary handle 224. The stapler 220 also includes a rotation knob 230 for rotation of the elongated portion (shaft) 228 to rotate the jaws 232, 235. Power pack 18 is shown fully loaded (inserted) within the handle housing 222 and cover 223 is shown closed to seal the power pack 18 from the external environment. As in the embodiment of FIGS. 1-12, the flag 42 extending from lead screw 36 engages a firing rod within the handle housing 222 to effect movement of a firing rod extending through elongated portion 228 to fire the circular arrays of staples when the motor of the power pack 18 is actuated. Power pack 90 having articulation described below can also be utilized with stapler 220.

By way of another example, the power pack can be used with a linear stapler that applies transverse rows of staples in a linear direction, i.e., parallel to the longitudinal axis of the stapler, such as shown in FIGS. 29A-29D. Surgical stapling instrument 240 can receive and be powered by the power pack 18 of the present disclosure. Stapler 240 has a handle 246 manually pivotable towards stationary handle 244 for clamping of the jaws, an elongated tubular portion 248 extending from the handle housing 242, and a jaw assembly containing an anvil (jaw) 252 and a cartridge (jaw) 255 containing linear rows of fasteners (staples) arranged perpendicular to the longitudinal axis of the stapler 240. The proximal anvil clamping surface 253 of anvil 252 and distal clamping surface 256 of cartridge 255 are brought into approximation by manual movement of handle 246 toward stationary handle 244 which advances cartridge 255 toward anvil 252. (Alternatively the anvil could be retracted toward the cartridge) The stapler 240 also includes a rotation knob 250 for rotation of the elongated portion (shaft) 248 to rotate the elongated portion 248 and jaws 252, 255. Power pack 18 is shown fully loaded (inserted) within the handle housing 242 and cover 243 is shown closed to seal the power pack 18 from the external environment. As in the embodiment of FIGS. 1-12, the flag 42 extending from lead screw 36 engages a firing rod within the handle housing 242 to effect movement of a firing rod extending through elongated portion 248 to fire the staples from cartridge 255 when the motor of the power pack 18 is actuated. Power pack 90 having articulation described below can also be utilized with stapler 240.

The power pack 18 can also be used with single firing instruments that fire a single staple, clip, tack, etc. into body tissue. Two examples of such instruments are illustrated in FIGS. 31A-31D and FIGS. 34A-34D. Turning first to the instrument 280 of FIGS. 31A-31D, by way of example, surgical clip applying instrument 280 can receive and be powered by the power pack 18 of the present disclosure. Stapler 280 has a handle 286 manually pivotable towards stationary handle 284 for loading a clip into the jaws, an elongated tubular portion 288 extending from the handle housing 282, and a pair of pivotable jaws 292 which support a clip therebetween. Closing of the jaws 292 crimps the clip about tissue. The clip applier 280 also includes a rotation knob 290 for rotation of the elongated portion (shaft) 288 to rotate the jaws 292. Power pack 18 is shown fully loaded (inserted) within the handle housing 282 and cover 283 is shown closed to seal the power pack 18 from the external environment. As in the embodiment of FIGS. 1-12, the flag 42 extending from lead screw 36 engages a rod within the handle housing 282 operably connected to a clip closing mechanism to effect movement of the clip closing mechanism to close the jaws to apply to tissue a surgical clip supported by the jaws 292. The power pack 18 can also have a motor powered drive assembly for advancing the clip into the jaws 292, the drive assembly engageable with a clip feed mechanism.

Another example of a single firing instrument is illustrated in FIGS. 34A-34D and designated generally by reference numeral 340. Instrument 340 can receive and be powered by the power pack 18 of the present disclosure. Instrument 340 has a handle 346 manually pivotable towards stationary handle 344 for angling the surgical tack and an elongated tubular portion 348 extending from the handle housing 342. Tacker support 345 is pivotable relative to the longitudinal axis by movement of handle 346 which is operably connected to an elongated member which pivots support 345. The instrument 340 also includes a rotation knob 350 for rotation of the elongated portion (shaft) 348. Power pack 18 is shown fully loaded (inserted) within the handle housing 342 and cover 343 is shown closed to seal the power pack 18 from the external environment. As in the embodiment of FIGS. 1-12, the flag 42 extending from lead screw 36 engages a rod within the handle housing 342 operably connected to a tack firing mechanism to effect advancement of the tack 347 into tissue. The power pack 18 can also be provided with a motor powered drive assembly to pivot support 345.

In the embodiments of FIGS. 1-12, a gear mechanism is driven by the motor to rotate the lead screw to advance the drive mechanism to effect firing of the staples. In the alternate embodiments of FIGS. 24A-27D, a belt drive mechanism is used to effect firing. The belt drive mechanism is contained in the power pack 18 in the same manner as the gear mechanism of the foregoing embodiments, and thus the power pack for the belt drive would include the housing 19 of the configuration of FIG. 1 and loaded in the stapler 1 in the same manner as power pack 18 described above. The belt drives of FIGS. 24A-27D are described below for use with stapler 1 of FIG. 1A but can be used in the other surgical staplers and instruments disclosed wherein which are designed to receive power pack 18 or power pack 90 for powered actuation.

Turning first to the embodiment of FIGS. 24A-24D, the belt drive assembly (mechanism) includes a motor 148 connected to a planetary gear box 150 configured to gear down the output of the motor 148 for proper drive speeds for firing staples from jaw 8a through the tissue into contact with the anvil of jaw 8b. The planetary gear box 150 drives a lead screw 144 via the drive belt operatively connected to the motor shaft. More specifically, upon rotation of the motor shaft by motor 148, first rotatable disc 152 (also referred to as the first wheel or pulley) is rotated in a first direction, causing movement of belt 156 and rotation of second rotatable disc 154 (also referred to as the second wheel or pulley). Note the two discs 152, 15 are spaced apart and not in contact. Lead screw 144 is operatively connected to disc 154 so that rotation of disc 154 causes rotation of lead screw 144 in the same direction. The power pack 18 includes a battery which can be rechargeable outside the stapler when the power pack 18 is removed. The motor 148 is actuated in the various ways described above with regard to power pack 18 of FIG. 3A. A tensioner can be provided such as tensioner 158, illustratively in the form of a tension disc or wheel, to apply a force against the belt 156. In the orientation of FIGS. 24C and 24D, the tensioner 158 is positioned underneath the drive belt 156 and applies an upward tensioning force against the belt 156 in a direction toward discs 152, 154. Other types of mechanisms to apply a tensioning force to the belt are also contemplated for use in the embodiments of FIGS. 24A-27D if such tensioning of the drive belt 156 is desired.

Connected to the end of lead screw 144 (the end opposite of the connection to the disc 154) is a drive mechanism 142. The drive mechanism 142, like drive mechanism 40 of FIG. 3A, is configured to move in a linear motion (in an axial direction) along the lead screw 144 in response to rotation of the lead screw 144. For example, as in the drive mechanism 40, drive mechanism 142 may include internal threads that engage external threads of the lead screw 144 and may include slides engaged in a track that prevent the drive mechanism 142 from rotating and therefore cause the drive mechanism 142 to move linearly in response to rotation of the lead screw 144. As shown, the lead screw 144 extends alongside, slightly spaced from, the motor 148 and gear box 150, i.e., both the motor 148/gear box 150 and lead screw 144 extending longitudinally with the lead screw 144 parallel to the motor 148. The drive mechanism 142 extends proximally of the proximal end of the motor 148 in the illustrated embodiment.

The drive mechanism 142, like drive mechanism 140 of FIG. 3A, includes a first output flag or yoke 146 with slot 143 configured to engage a staple firing rod 46 extending longitudinally within the handle 4. The flag 146 is the same as flag 42 of FIG. 4A and engages the staple firing rod 46 in the same manner as flag 42. Therefore, for brevity, further discussion of flag 146 and it engagement with firing rod 46 is not provided as the structure and function of flag 42, and alternative firing rod engagement features, are fully applicable to flag 146 of FIGS. 24A-24D. In brief, as the motor 148 generates rotational motion of the lead screw 144 through the drive belt, the drive mechanism 144 moves in linear motion along the lead screw 144 to effect linear movement of the firing rod 46 which advances the staple driving mechanism to advance (fire) the staples out from jaw 8b through tissue and into contact with the anvil in jaw 8a.

FIGS. 25A-25D illustrate an alternate embodiment of a belt drive mechanism. Belt drive mechanism (assembly) 160 is identical to belt drive 140 except for the different sized discs (wheels). That is, assembly 160 has a motor 168 connected to a planetary gear box 170 configured to gear down the output of the motor 168. The planetary gear box 170 drives a lead screw 164 through the belt drive operatively connected to the motor shaft. Upon rotation of the motor shaft by motor 168, first disc 172 is rotated in a first direction, causing movement of belt 176 and rotation of second disc 174 in the same direction. Lead screw 164 is operatively connected to disc 174 so that rotation of disc 174 causes rotation of lead screw 164 in the same direction. A tensioner 178 like tensioner 158 can be provided to apply tension to the belt 176. The drive mechanism 162, like drive mechanism 40 of FIG. 3A, includes a first output flag or yoke 166 with slot 163 configured to engage a staple firing rod 46 in the same manner as flag 42. Rotation of the motor shaft generates rotational motion of the lead screw 164 through the drive belt, causing the drive mechanism 162 to move in linear motion along the lead screw 164 to effect linear movement of the firing rod 46 which advances the staple driving mechanism to advance (fire) the staples out from jaw 8*b* through tissue and into contact with the anvil in jaw 8*a*.

The belt drive 160 differs from belt drive 140 of FIG. 24A in that second disc 174 which is operatively connected to lead screw 164 is larger in diameter than first disc 172. Consequently, instead of providing a one to one ratio of the discs as in discs 154 and 152 of FIG. 24A, a greater ratio of disc 174 to disc 172 is provided which varies the output of motor 168. That is, the rotational output of lead screw 164 is less than the rotational output of the motor shaft due to the differing degree of rotation of discs 174, 178 due to the varying sizes. In all other respects, mechanism 160 is identical to mechanism 140.

FIGS. 26A-26D illustrate an alternate embodiment of a belt drive mechanism. Belt drive mechanism (assembly) 180 is identical to belt drive 140 of FIG. 24A except for the configuration of the drive belt and discs. That is, assembly 180 has a motor 188 connected to a planetary gear box 190 configured to gear down the output of the motor 188. The planetary gear box 190 drives a lead screw 184 through the belt drive operatively connected to the motor shaft. Upon rotation of the motor shaft by motor 188, first disc (wheel or pulley) 192 is rotated in a first direction, causing movement of belt 196 and rotation of second disc (wheel or pulley) 194. Lead screw 184 is operatively connected to disc 194 so that rotation of disc 194 causes rotation of lead screw 184 in the same direction. A tensioner 198 like tensioner 158 can be provided to apply tension to the belt 196. The drive mechanism 182, like drive mechanism 140 of FIG. 3A, includes a first output flag or yoke 186 with slot 183 configured to engage a staple firing rod 46 in the same manner as flag 42. Rotation of the motor shaft generates rotational motion of the lead screw 184 through the drive belt, causing the drive mechanism 182 to move in linear motion along the lead screw 184 to effect linear movement of the firing rod 46 which advances the staple driving mechanism to advance (fire) the staples out from jaw 8*b* through tissue and into contact with the anvil in jaw 8*a*.

The belt drive 180 differs from belt drive 140 of FIG. 24A in that discs 192, 194 have teeth to engage ribs or treads on belt 196. As shown, the toothed discs 192, 194 are spaced apart so their teeth/projections do not intermesh—the teeth of disc 192 engage belt 196 and the teeth of disc 194 engage belt 196. Rotation of disc 192 moves drive belt 194 in the same direction due to its engagement with the teeth, which causes rotation of toothed disc 194 in the same direction due to engagement with its teeth to rotate lead screw 184. In all other respects, mechanism 180 is identical to mechanism 140.

FIGS. 27A-27E illustrate an alternate embodiment of a belt drive mechanism. Belt drive mechanism (assembly) 200 is identical to belt drive 180 except for the different sized discs. That is, assembly 200 has a motor 208 connected to a planetary gear box 210 configured to gear down the output of the motor 208. The planetary gear box 210 drives a lead screw 204 through the belt drive operatively connected to the motor shaft. Upon rotation of the motor shaft by motor 208, first disc (wheel or pulley) 212 is rotated in a first direction, causing movement of belt 216 and rotation of second disc (wheel or pulley) 214. Lead screw 204 is operatively connected to disc 214 so that rotation of disc 214 causes rotation of lead screw 204 in the same direction. A tensioner 218 like tensioner 198 can be provided to apply tension to the belt 216. The drive mechanism 202, like drive mechanism 140 of FIG. 3A, includes a first output flag or yoke 206 with slot 203 configured to engage a staple firing rod 46 in the same manner as flag 42. Rotation of the motor shaft generates rotational motion of the lead screw 204 through the drive belt, causing the drive mechanism 202 to move in linear motion along the lead screw 204 to effect linear movement of the firing rod 46 which advances the staple driving mechanism to advance (fire) the staples out from jaw 8*b* through tissue and into contact with the anvil in jaw 8*a*.

The belt drive 200 differs from belt drive 180 of FIG. 24A in that second toothed disc 214 which is operatively connected to lead screw 204 is larger in diameter than first toothed disc 172. Consequently, instead of providing a one to one ratio of the discs as in discs 194 and 192, a greater ratio of disc 214 to disc 212 is provided which varies the output of motor 208. That is, the rotational output of lead screw 204 is less than the rotational output of the motor shaft due to the differing degree of rotation of discs 214, 212 due to the varying sizes. In all other respects, mechanism 200 is identical to mechanism 180.

It should be appreciated that the foregoing belt drive mechanisms can be used as an alternative to the gear mechanism in power pack 18 as well as an alternative to one or both of the gear mechanisms of power pack 90 discussed below.

In the foregoing embodiments, the power pack 18 was described for powering staple firing. In an alternate embodiment, the power pack can include a drive mechanism for effecting articulation. This motor powered articulation can be in addition to the motor powered staple firing, or alternatively, the power pack can be used solely for powered articulation. The embodiment of FIGS. 14A-23B illustrate a surgical stapler and power pack which powers both staple firing and articulation. If only for articulation, the power pack described below (power pack 90) would not include the gear mechanism engageable with the firing rod 46 for staple firing.

With initial reference to FIGS. 14A-14C, surgical stapler 61 is identical to surgical stapler 1 of FIG. 1A except for the power pack mounted in the stapler 61 and the articulation rod in the stapler 61 which is engaged by the power pack. Thus, like stapler 1, stapler 61 has a handle assembly 63, an endoscopic portion 66 extending distally therefrom and a pair of jaws 68*a*, 68*b*, (collectively "jaws 68") with at least one of the jaws movable relative to the other jaw, e.g., jaw 68*b* containing the staples (fasteners) movable toward stationary jaw 68*a* containing the anvil pockets. Handle 72 like handle 14 of stapler 1 is pivotable toward stationary handle 70 to approximate jaws 68*a*, 68*b* to clamp tissue between the closed jaws 68*a*, 68*b*. Handle assembly 63 includes a housing 64 and cover 62 which is identical to cover 22 of stapler 1, i.e., pivotably mounted to the housing 64 to move from a closed to an open position for top loading (or alternatively other directional loading) a power pack into the compartment within the housing 64. The compartment, like compartment 25 described above, retains the power pack and can include guiding structure for alignment of the power pack similar to guiding structure 23 described above to receive guides 90a, 90b of power pack 90. Stapler 61 also includes a rotation knob 74 which functions in the same manner as rotation knob 12 of stapler 1 described above to rotate tubular portion (shaft) 66. The jaw assembly, i.e., jaws 68a, 68b, articulate about joint 69 to move the jaws 68a, 68b to angular positions with respect to the longitudinal axis of stapler 61.

The power pack in the embodiment of FIGS. 14A-23B is designated by reference numeral 90 and has a motor assembly and drive mechanism for firing staples which is identical to that of the power pack 18 of FIG. 3A. However, power pack 90 differs from power pack 18 in that it additionally has a motor assembly and drive mechanism for articulating the jaws. The addition of the articulation assembly can be appreciated by a comparison of the cross-sectional view of FIG. 4H, which only effects firing of the fasteners (staplers), and the cross-sectional view of FIG. 15F which effects firing of fasteners and articulation of the jaw assembly.

More specifically, with reference to FIGS. 15A-15F and 18B, the powered staple firing assembly like the firing assembly of power pack 18 of FIG. 4H, includes a motor 83 connected to a planetary gear box 85 configured to gear down the output of the motor in the same manner as motor 32 and gear box 34 of power pack 18. The planetary gear box 85 drives a lead screw 86 through one or more gears operatively connected to the motor shaft. More specifically, upon rotation of the motor shaft by the motor 83 in a first direction, gear 81 is rotated in the same first direction, causing rotation of the gear 84 in a second opposite direction due to the intermeshed teeth of gears 81 and 84. Lead screw 86 is operatively connected to gear 84 so that rotation of gear 84 causes rotation of lead screw 86 in the same direction. The power pack 18 includes a battery 33 which can be rechargeable outside the stapler when the power pack 18 is removed. The power pack 90 in some embodiments can include a power switch which is activated, i.e., turned on, by the clinician to start the motor and effect staple firing. In other embodiments, the motor can automatically turn on when fully loaded or upon actuation of another control on the stapler housing 4.

Connected to the end of lead screw 86 (the end opposite the connection to the gear 84) is a drive mechanism 80 which is configured to move in a linear motion (in an axial direction) along the lead screw 86 in response to rotation of the lead screw 86. Drive mechanism 80 includes a flag or yoke 82 identical to yoke 42 of power pack 18 discussed above, which engages flange or boss 76 of firing rod 75 within housing 64 of stapler 61. The connection of the flag 82 to the firing rod 76, the motor and gear mechanism, and the drive mechanism 80 of power pack 90 are the same as the power pack 18 and therefore the aforedescribed functions and features/components of power pack 18 for staple firing are fully applicable to the function and features/components of power pack 90 for staple firing so for brevity are not fully repeated herein. It should also be appreciated that the alternative mechanisms for motor powered stapled firing, such as the various belt drive mechanisms discussed above and/or illustrated in the Figures, can also be used in the power pack 90 to effect staple firing. Additionally, the various sensors discussed above with regard to sensing the firing stroke can also be provided in power pack 90 for the same uses.

Power pack 90 also has an articulation assembly, shown in detail in FIGS. 22A-22D. The articulation assembly includes a powering assembly including a motor 96 connected to a planetary gear box 93 configured to gear down the output of the motor 96. The planetary gear box 93 drives a lead screw 98 through gears 91, 92 operatively connected to the motor shaft. More specifically, upon rotation of the motor shaft by motor 96 in a first direction, gear 91 is rotated in the same first direction, causing rotation of the gear 92 in a second opposite direction due to the intermeshed teeth of gears 92 and 91. Lead screw 98 is operatively connected to gear 92 so that rotation of gear 92 causes rotation of lead screw 98 in the same direction. The power pack 90 in some embodiments can include a power switch which is activated, i.e., turned on, by the clinician to start the motor and effect articulation.

Connected to the end of lead screw 98 (the end opposite the connection to the gear 92) is a drive mechanism 95 configured to move in a linear motion (in an axial direction) along the lead screw 98 in response to rotation of the lead screw 98. For example, the drive mechanism 95, like drive mechanisms 40 and 80 described above, may include internal threads that engage external threads of the lead screw 98 and may include slides engaged in a track that prevent the drive mechanism 95 from rotating and therefore cause the drive mechanism 95 to move linearly (axially) in response to rotation of the lead screw 98. As depicted, the power pack 90 has a compact configuration as the lead screw 98 extends alongside, slightly spaced from, the motor 96 and gear box 93, i.e., both the motor 96/gear box 93 and lead screw 98 extending longitudinally with the lead screw 98 parallel to the motor 96. The drive mechanism 95 is connected to a proximal end of lead screw 98. The drive mechanism 95 has an articulation rod engagement feature in the form of a flange or yoke 94 extending therefrom having legs 99a and a recess 99b to engage an articulation rod 79 within the housing 63. In the illustrated embodiment (see e.g., FIGS. 15B and 22C), the articulation rod 79 includes a flange 78 which is engageable by the flag 94. The output flag 94 can engage the bossed end 78 of the articulation tube 79 in substantially the same manner as the output flag 42 engages the bossed end 44 of the firing rod 46 as discussed above.

The articulation assembly of the power pack 90 is oriented in the opposite direction from the staple firing assembly to minimize the space required in the power pack 90, thereby providing the power pack with a compact configuration. As can be appreciated by reference to FIGS. 15A and 15F, the drive assembly 80 and associated flag 82 are at a proximal end of the assembly for firing staples with the lead screw 86 extending distally toward the gears 81, 84. The driving assembly 95 with associated flag 94 of the assembly for articulation are at a distal end with the lead screw 98 extending proximally toward gears 91, 92. Also as can be appreciated by reference to the orientation of FIGS. 15A and 15F, the articulation assembly is above (closer to the cover 22) than the firing assembly, and the articulation assembly in the illustrated embodiment is positioned axially proximal of gears 81, 84 and axially distal of drive mechanism 80, radially spaced from lead screw 86.

Figure 15C:
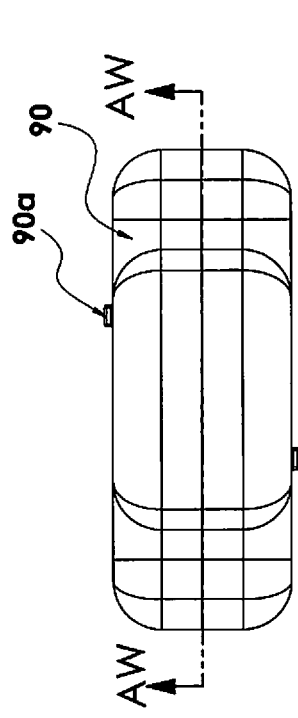
FIG. 15C is a top view of the power pack of FIG. 14A for effecting both firing and articulation of the surgical stapler.
Figure 15D:
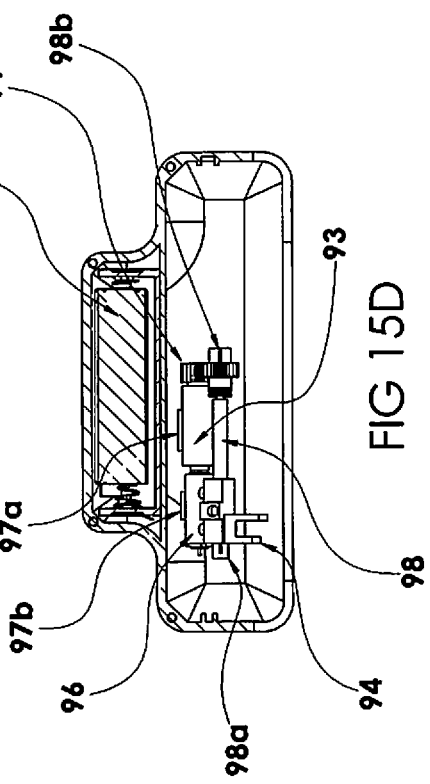
FIG. 15D is a cross-sectional view taken along line AW-AW of FIG. 15C.
Figure 15E:
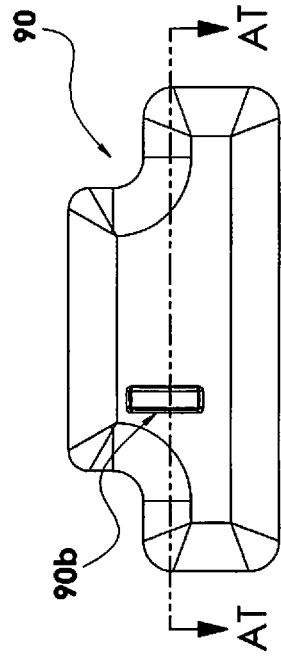
FIG. 15E is a side view of the power pack of FIG. 14A.
Figure 15F:
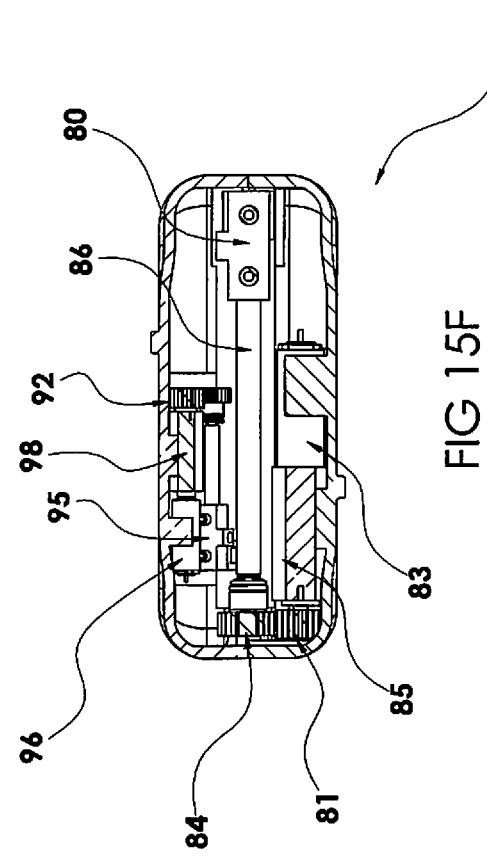
FIG. 15F is a cross-sectional view taken along line AT-AT of FIG. 15E.
Figure 16D:
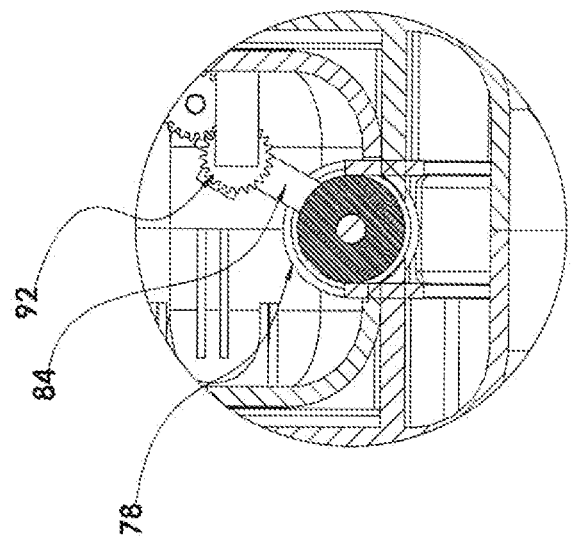
FIG. 16D is a close up view of the area of detail H of FIG. 1C.
Figure 16C:
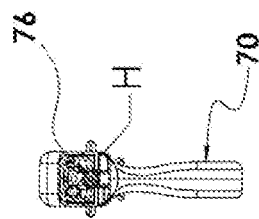
FIG. 16C is a cross-sectional view taken along line F-F of FIG. 15C.
Figure 16A:
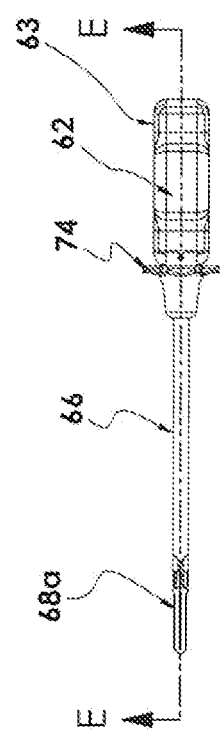
FIG. 16A is a top view of the surgical stapler of FIG. 14A, the view being the same as FIG. 14B but having section line E-E.
Figure 16B:
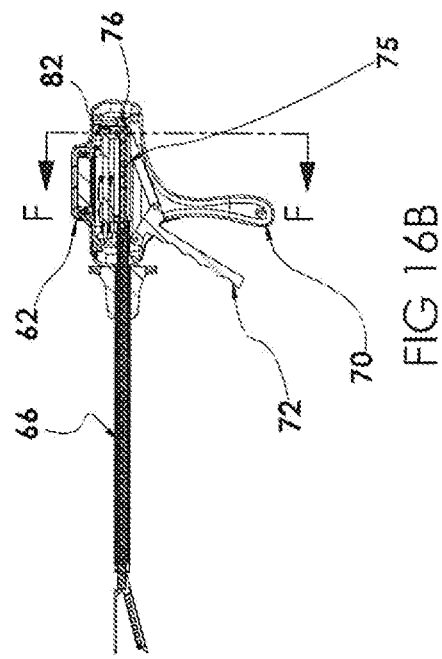
FIG. 16B is a side view of the surgical stapler of FIG. 14A, the view being the same as FIG. 14C but having section line F-F and identified area of detail G.
Figure 18B:
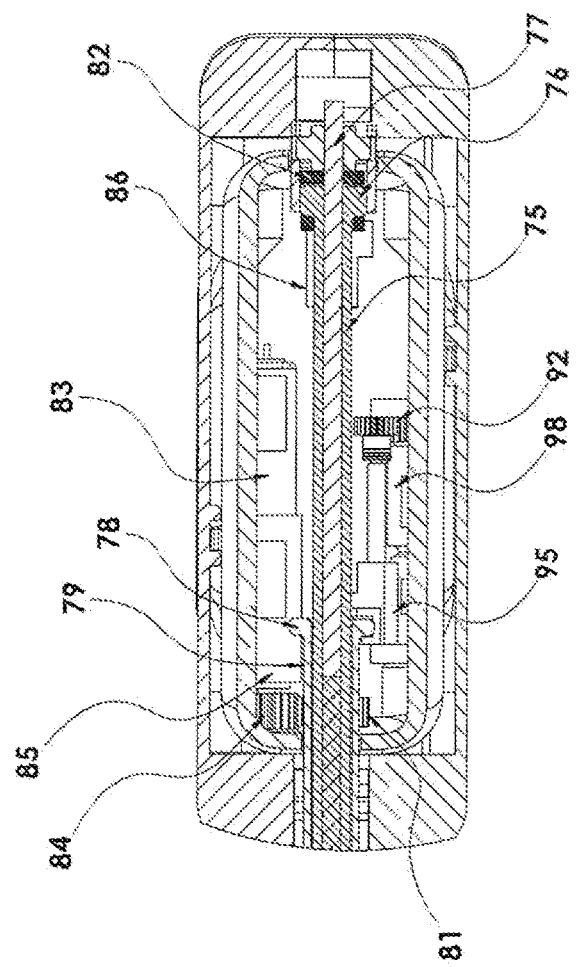
FIG. 18B is a close up view of the area of detail BA of FIG. 18A.
Figure 17:
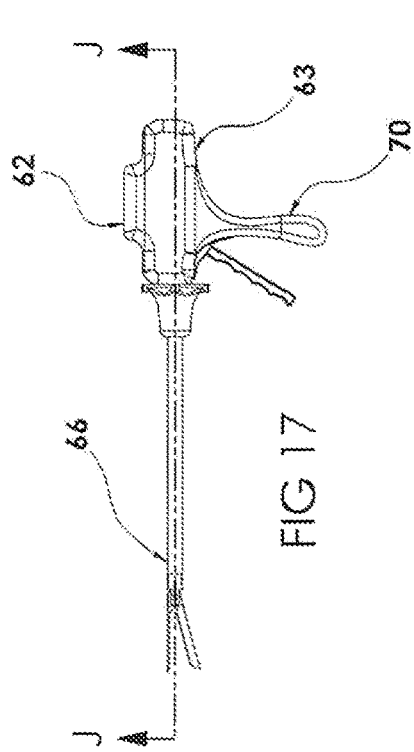
FIG. 17 is a side view of the surgical stapler of FIG. 14A, the view being the same as FIG. 14A but having section line J-J.
Figure 18A:
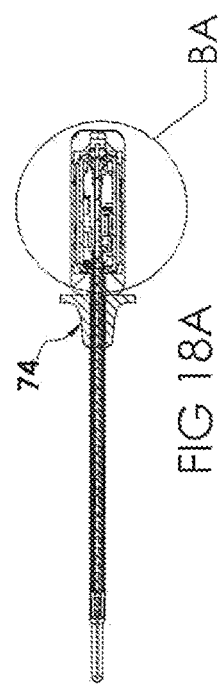
FIG. 18A is a cross-sectional view taken along line J-J of FIG. 17.
Figure 19C:
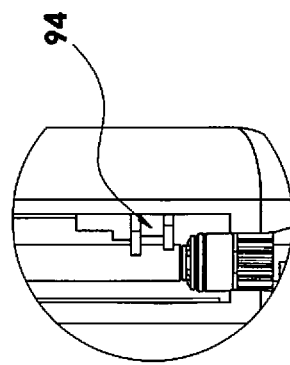
FIG. 19C is an enlarged view of the area of detail AL of FIG. 19A.
Figure 19B:
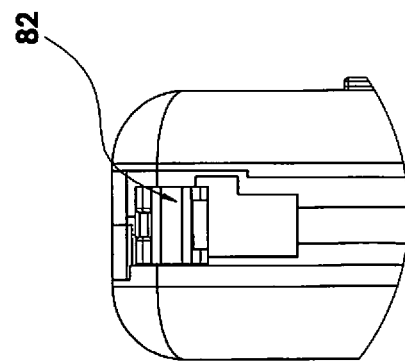
FIG. 19B is an enlarged view of the area of detail AK of FIG. 19A.
Figure 19A:
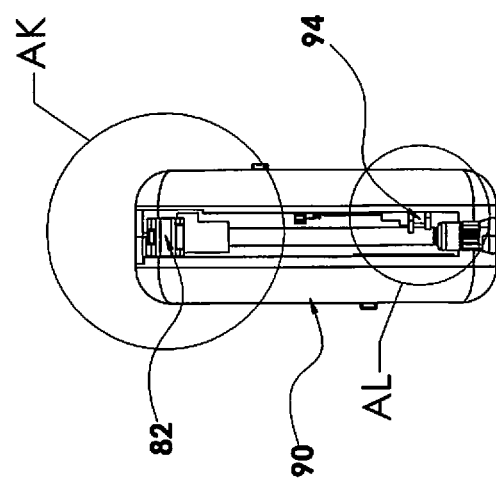
FIG. 19A is a top cutaway view of the power pack of FIG. 14A.
Figure 23B:
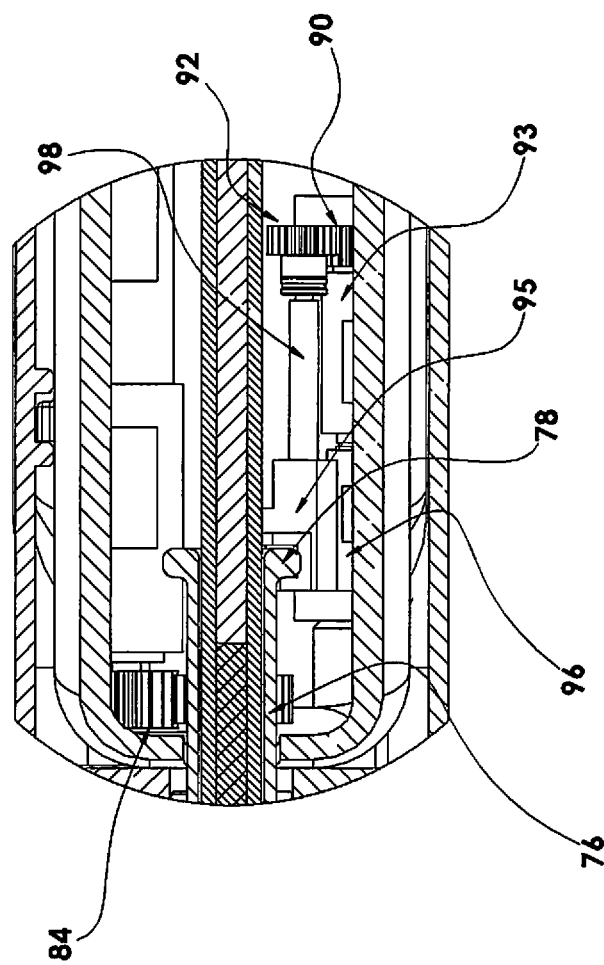
FIG. 23B is an enlarged view of the area of detail AU of FIG. 23A.
Figure 23A:
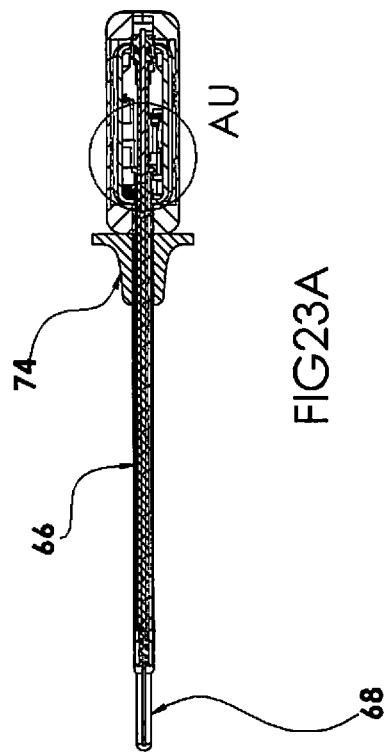
FIG. 23A is a cross-sectional side view of the surgical stapler of FIG. 14A, the view being the same as FIG. 18A but having and identified area of detail AU.
Figure 29C:
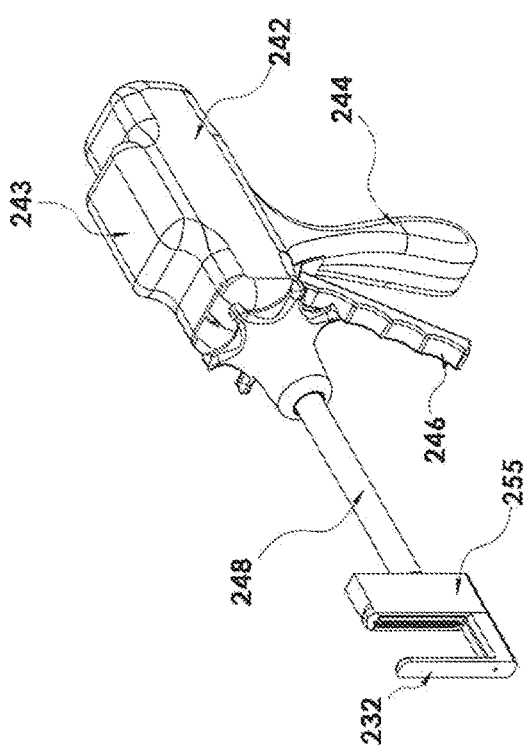
FIG. 29C is a perspective view of the linear stapler of FIG. 29A.
Figure 29D:
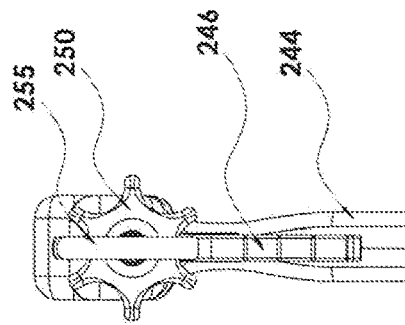
FIG. 29D is a front view of the linear stapler of FIG. 29A.
Figure 29A:
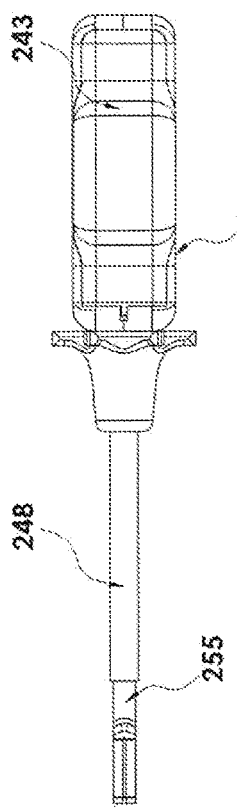
FIG. 29A is a top view of an alternate embodiment of the surgical instrument containing the power pack of FIG. 3A within the handle compartment, the surgical instrument being an open surgery linear stapler.
Figure 29B:
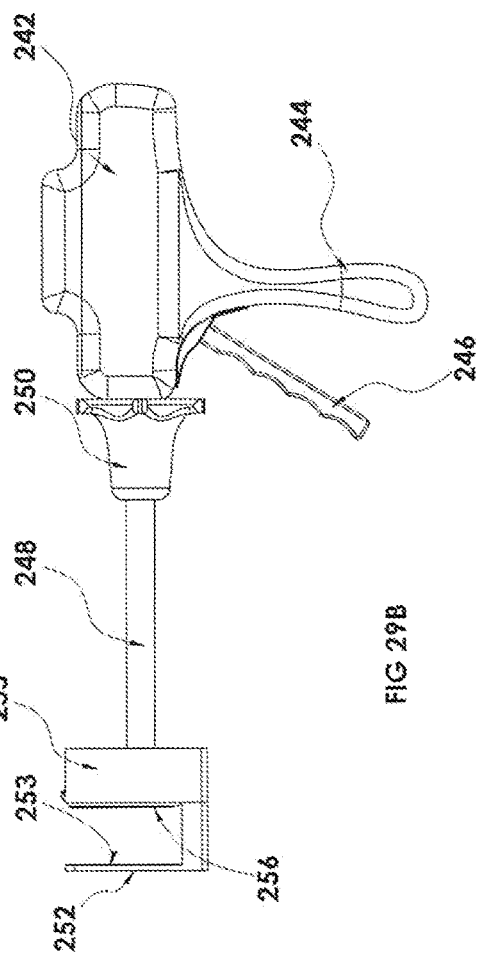
FIG. 29B is a side view of the linear stapler of FIG. 29A.

The power pack 90, like power pack 18 can have features/structure to constrain the motors 84 and 96. In the embodiment of FIG. 15D, such feature is in the form of proximal rails 97a and distal rails 97b spaced apart axially within the housing of the power pack 90. Gear box 93 is seated within proximal rails 97a and motor 96 is seated within distal rails 97b, the rails 97a, 97b retaining the motor and preventing axial and rotational movement within the housing of power pack 90. Bearing or bushings 98a, 98b can also be provided to constrain the lead screw 98 at opposing ends, while allowing rotation thereof, thereby also constraining the motor. Other features can additionally or alternatively be provided to restrain the motor from axial movement while allowing rotation of the lead screw.

The power pack 90 can include guides, e.g., projections 90a, 90b, either axially aligned or axially offset, similar to guides 28 of power pack 18 for alignment with guiding structure in the compartment of stapler 61.

In use, with the cover 62 of stapler 61 in the open position, power pack 90 is loaded into the compartment of the handle housing 63. The cover 62 is closed to seal the power pack 90 from contaminants in same manner as cover 22 of stapler 1. Upon loading of the power pack 90, flag 82 of the drive mechanism 80 of the staple firing assembly engages flange 76 of firing rod 75 and flag 94 of drive mechanism 95 of the articulation assembly engages flange or bossed end 78 of articulation rod 79. Actuation of the motor 96 effects linear motion of the flag 94 which moves the articulation rod 79 linearly (axially). The articulation rod 79 is either directly coupled to the joint 69, or coupled to another member or multiple members which are coupled to the joint 69. When moved linearly, the articulation rod 79 effects movement of the jaws 68A, 68b of the stapler 61 to angular positions with respect to the longitudinal axis of the stapler 61. Note the articulation drive assembly operates in a similar manner as the firing drive assembly of power pack 18 in that when the power pack 90 is secured to the tube 79 by the second output flag 94, linear motion generated at the second output flag 94 is transferred to linear motion of the tube 79. Actuation of the motor 83 effects linear motion of the flag 82 which moves the firing rod 75 linearly (axially). The firing rod 75 either extends through the elongated portion 66 for engagement of the firing mechanism in the jaw 68b or is coupled to another elongated component(s) extending through the endoscopic portion 66 to engage the firing mechanism in the jaw 68b. Note that the articulation rod or tube 79 can be configured to receive the firing rod 75 so that the firing rod 75 can move within the tube 79 to effect firing and the articulation rod 79 can slide linearly over the firing rod to effect articulation.

After use, the cover 62 can be opened and the power pack 90 removed and charged while the handle assembly 63 (and stapler 61) is sterilized or disposed of if the stapler is a disposable instrument. The power pack 90, like power pack 18 described above, may be reused without requiring sterilization by being inserted into the receptacle of the now-sterilized handle assembly 63 or a different sterile handle assembly. Thus, the removable power pack 90, like power pack 18, does not need to be subjected to the sterilization process and, therefore, contact between the harsh temperatures and/or chemicals of the sterilization process is advantageously avoided.

One or more seals are utilized for sealing power pack 18 and power pack 90 within the handle assembly 2 or 63 so that the power pack remains sterile and is not exposed to bodily fluids during surgical procedures. For example, as discussed above, in the stapler 1 of FIG. 1, the top seal 24 is positioned at the interface between the cover 22 and the housing 4 of the handle assembly 2 where the cover 22 closes for sealing the opening into the receptacle 20 and, therefore, power pack 18 from the environment when positioned therein. Similarly, in the stapler 61 of FIG. 14A, the top seal is positioned at the interface between the cover 62 and the housing 64 of the handle assembly 63 wherein the cover 62 closes for sealing the opening into the receptacle and, therefore, power pack 90 from the environment when positioned therein. As shown in FIGS. 21A-21C, further seals can be provided to further seal the receptacle and thus the power pack. An O-ring 56 is placed around the articulation rod 79 to seal the space around the rod 79. A flexible trigger seal 58 surrounds the lever 72 for sealing the internal components of the handle assembly 63 throughout the range of positions of the movable lever 72. Thus, all of the openings into the receptacle of the handle assembly 63 are sealed from the external environment. The O-ring seal 56 and trigger seal 58 can also be used in stapler 1 so the openings into the receptacle 20 of handle assembly 2 are sealed from the external environment. Elastomeric seal 59a seals cover 62 from U-channel 59 within the handle which supports the power pack 90. Additional seals can be provided to prevent flow of body fluid through the endoscopic portion 66 (and endoscopic portion 6). Other types of seals and seals in different locations are also contemplated.

As noted above, the power pack 90 can be used with the other staplers disclosed herein, e.g. circular staplers, linear staplers, as well as other instruments wherein two powered functions are desired. The first motor assembly can effect linear motion of a first elongated member to effect a first function of the stapler, e.g., clamping, articulation, firing, and the second motor assembly can effect linear motion of a second elongated member to effect a second different function of the stapler, e.g., clamping, articulation, firing. In the embodiment of FIG. 14A, one function is articulation and another function is staple firing. Note the power pack 90 can also be used with surgical instruments other than surgical staplers such as those illustrated in FIGS. 33A and 34A.

In the foregoing embodiments, use of the power pack of the present disclosure to fire staples such as in endoscopic linear staplers, open surgery linear staplers, circular staplers, as well as firing single clips or tacks were disclosed as examples. It should be appreciated that the power packs of the present disclosure can also be used to power functions of other surgical instruments. FIGS. 33A-34D illustrate two examples of such instruments.

In FIGS. 32A-32D an endoscopic scissors, designated generally by reference numeral 300, can receive and be powered by the power pack 18 (or power pack 90) of the present disclosure. Scissors 300 has a handle 306 manually pivotable towards stationary handle 304 to effect closing of the jaws, an elongated tubular portion 308 extending from the handle housing 302, and a pair of pivotable jaws 312 with cutting edges. Closing of the jaws 312 severs tissue between the jaws. The scissors 300 include a rotation knob 310 for rotation of the elongated portion (shaft) 308 to rotate the jaws 312. Power pack 18 is shown fully loaded (inserted) within the handle housing 302 and cover 303 is shown closed to seal the power pack 18 from the external environment. As in the embodiment of FIGS. 1-12, the flag 42 extending from lead screw 36 engages a rod within the handle housing 302 operably connected to a jaw closing mechanism to effect movement of jaws 312 toward each other to sever tissue between the jaws 312. Either one or both jaws 312 can be movable.

In FIGS. 33A-33D an endoscopic grasper, designated generally by reference numeral 320, can receive and be powered by the power pack 18 (or power pack 90) of the present disclosure. Grasper 320 has a handle 326 manually pivotable towards stationary handle 324 to effect closing of the jaws 332, an elongated tubular portion 328 extending from the handle housing 322, and a pair of pivotable jaws 332 with grasping surfaces that can include teeth, roughened surfaces, ribs, etc. . . . Closing of the jaws 332 grasps tissue between the grasping surfaces of jaws 332. Either one of the jaws can be movable, i.e., pivotable, or both jaws can be movable (pivotable) toward and away from each other, for movement between closed and open positions. The graspers 320 includes a rotation knob 330 for rotation of the elongated portion (shaft) 328 to rotate the jaws 332. Power pack 18 is shown fully loaded (inserted) within the handle housing 322 and cover 323 is shown closed to seal the power pack 18 from the external environment. As in the embodiment of FIGS. 1-12, the flag 42 extending from lead screw 36 engages a rod within the handle housing 322 operably connected to a jaw closing mechanism to effect movement of jaws 332 to close the jaws to grasp tissue between the jaws 332. It should be appreciated that the aforedescribed variations of the power packs can also be used with the surgical instruments of FIGS. 32A and 33A.

The power packs 18 and 90 disclosed herein can be used in surgery where the clinician manually clamps the jaws and actuates the motor or motors to provide powered staple firing and/or powered jaw articulation. It is also contemplated that the power packs 18 and 90 can be used with robotic driven surgical staplers wherein clamping, motor actuation and any other functions of the instrument are performed robotically, including remote robotic control.

Although the apparatus and methods of the subject disclosure have been described with respect to preferred embodiments, those skilled in the art will readily appreciate that changes and modifications may be made thereto without departing from the spirit and scope of the present disclosure as defined by the appended claims.

What is claimed is:

1. A surgical instrument comprising:
a housing containing a compartment therein;
a cover movable from a closed position to an open position to access the compartment;
an elongated member having a longitudinal axis extending distally from the housing;
a jaw assembly including a first jaw and a second jaw at a distal portion of the elongated member, at least the first jaw movable with respect to the second jaw;
a jaw clamping mechanism movable between a first position and a second position to move at least the first jaw toward the second jaw to clamp tissue between the first and second jaws;
an articulation mechanism positioned within the compartment and movable within the compartment between a first position and a second position to articulate the jaw assembly from a linear position to a second position angled with respect to a longitudinal axis of the elongated member; and
a power pack loadable into the compartment by a clinician, the power pack having a first motor and a first engagement member mechanically engageable with the articulation mechanism within the compartment to effect movement of the articulation mechanism from the first position to the second position, wherein the power pack mechanically engages the articulation mechanism in the compartment prior to movement of the cover to the closed position, the cover openable to access the power pack during a surgical procedure.

2. The surgical instrument of claim 1, further comprising a handle manually movable to move the jaw clamping mechanism to clamp tissue between the first and second jaws such that clamping is non-powered.

3. The surgical instrument of claim 1, further comprising a first seal on the housing or the cover to seal about the cover in a closed position of the cover to protect the power pack positioned within the compartment of the housing, the first seal compressible by closure of the cover.

4. The surgical instrument of claim 3, further comprising a second seal to block passage of body fluids from the elongated member into the compartment.

5. The surgical instrument of claim 3, wherein the first seal extends around a perimeter for compression between the cover and the housing.

6. The surgical instrument of claim 1, wherein the cover is hingedly attached at a distal portion and is pivotable away from the housing in a direction away from the longitudinal axis of the surgical instrument to open the cover.

7. The surgical instrument of claim 1, wherein the first engagement member includes a yoke having a slot to receive the articulation mechanism.

8. The surgical instrument of claim 1, wherein the power pack is contained in the compartment out of contact with body fluids of a patient, and the power pack is reusable.

9. The surgical instrument of claim 1, wherein the power pack includes a sensor detecting a linear position of the first engagement member to indicate a position of articulation of the jaw assembly with respect to the longitudinal axis of the elongated member.

10. The surgical instrument of claim 1, wherein the power pack is removably loadable into the housing with the elongated member attached to the housing.

11. The surgical instrument of claim 1, wherein the power pack is out of contact with a handle when loaded in the compartment.

12. The surgical instrument of claim 1, wherein pivoting of the cover with the power pack loaded therein and the elongated member extending distally from the housing does not affect a position of the elongated member.

13. A surgical instrument comprising:
a housing containing a compartment therein;
an elongated member having a longitudinal axis extending distally from the housing;
a jaw assembly including a first jaw and a second jaw at a distal portion of the elongated member, at least the first jaw movable with respect to the second jaw;
a jaw clamping mechanism movable between a first position and a second position to move at least the first jaw toward the second jaw to clamp tissue between the first and second jaws;
an articulation mechanism positioned within the housing and movable between a first position and a second position to articulate the jaw assembly from a linear position to a second position angled with respect to a longitudinal axis of the elongated member;
a power pack loadable into the compartment by a clinician, the power pack having a motor and an engagement member mechanically engageable with the articulation mechanism within the compartment to effect movement of the articulation mechanism within the compartment from the first position to the second position, wherein engagement member of the power pack engages the articulation mechanism upon loading of the power pack into the compartment; and
a cover movable to a closed position subsequent to the engagement member of the power pack engaging the articulation mechanism, the cover openable to access the power pack during a surgical procedure.

14. The surgical instrument of claim 13, wherein the elongated member is attached to the housing and extends therefrom when the power pack is loaded into the compartment.

15. The surgical instrument of claim 13, wherein the power pack is top loaded into the compartment in a direction transverse to the longitudinal axis of the instrument to radially engage the articulation mechanism.

16. The surgical instrument of claim 13, wherein movement of the cover to open the cover with the power pack loaded therein and the elongated member extending distally from the housing does not affect a position of the elongated member.

17. The surgical instrument of claim 13, further comprising a first seal on the housing or the cover to seal about the cover in a closed position of the cover to protect the power pack positioned within the compartment of the housing, the seal compressible by closure of the cover.

18. The surgical instrument of claim 13, wherein the power pack has a length along a longitudinal axis parallel to the longitudinal axis of the elongated member, and a width transverse to the length, wherein the length extends the width.

19. The surgical instrument of claim 13, wherein the engagement member radially engages the articulation mechanism upon loading of the power pack into the compartment.

* * * * *